(12) United States Patent
Cooley et al.

(10) Patent No.: US 12,150,235 B2
(45) Date of Patent: Nov. 19, 2024

(54) TREATMENT PLANNING

(71) Applicant: Mevion Medical Systems, Inc., Littleton, MA (US)

(72) Inventors: James Cooley, Andover, MA (US); Gerrit Townsend Zwart, Durham, NH (US); Stanley J. Rosenthal, Wayland, MA (US); Mark R. Jones, Reading, MA (US); Lionel G. Bouchet, Framingham, MA (US); Robert Cessac, Littleton, MA (US); Joseph Jachinowski, Littleton, MA (US)

(73) Assignee: Mevion Medical Systems, Inc., Littleton, CO (US)

( * ) Notice: Subject to any disclaimer, the term of this patent is extended or adjusted under 35 U.S.C. 154(b) by 0 days.

(21) Appl. No.: 17/174,986

(22) Filed: Feb. 12, 2021

(65) Prior Publication Data

US 2021/0274635 A1    Sep. 2, 2021

Related U.S. Application Data

(63) Continuation of application No. 15/643,865, filed on Jul. 7, 2017, now Pat. No. 10,925,147.

(Continued)

(51) Int. Cl.
*A61N 5/10* (2006.01)
*A61B 5/00* (2006.01)
(Continued)

(52) U.S. Cl.
CPC .......... *H05H 13/02* (2013.01); *A61B 5/0036* (2018.08); *A61N 5/103* (2013.01); *A61N 5/1036* (2013.01);
(Continued)

(58) Field of Classification Search
None
See application file for complete search history.

(56) References Cited

U.S. PATENT DOCUMENTS

| 463,291 | A | 11/1891 | Dodson |
| 773,508 | A | 10/1904 | Leblanc |

(Continued)

FOREIGN PATENT DOCUMENTS

| CA | 2629333 A1 | 5/2007 |
| CN | 1377521 A | 10/2002 |

(Continued)

OTHER PUBLICATIONS

Morel P, et. al. "Spot weight adaptation for moving target in spot scanning proton therapy" 2015; Front. Oncol. 5:119. doi: 10.3389/fonc.2015.00119. (Year: 2015).*

(Continued)

*Primary Examiner* — Laura Yesildag
(74) *Attorney, Agent, or Firm* — ArentFox Schiff LLP

(57) ABSTRACT

An example method includes: receiving, from a treatment planning process, information that is based on a dose distribution for an irradiation target; and performing at least one of the following operations: moving structures to trim spots of a particle beam so that the spots of the particle beam approximate pre-trimmed spots for which characteristics are obtained based on the information received; moving structures to produce a trimming curve for a layer of an irradiation target based on a specification of a trimming curve for the layer included in the information received; moving structures to produce a single trimming curve for all radiation fields of an irradiation target based on specifications of the single trimming curve included in the information received; or moving structures based on configuration information for the structures in the information received.

30 Claims, 37 Drawing Sheets

Related U.S. Application Data

(60) Provisional application No. 62/360,227, filed on Jul. 8, 2016.

(51) Int. Cl.
   *H05H 7/00*     (2006.01)
   *H05H 7/04*     (2006.01)
   *H05H 13/02*    (2006.01)

(52) U.S. Cl.
   CPC ......... *A61N 5/1037* (2013.01); *A61N 5/1045* (2013.01); *A61N 5/1065* (2013.01); *A61N 5/1077* (2013.01); *H05H 7/04* (2013.01); *A61N 2005/1087* (2013.01); *A61N 2005/1094* (2013.01); *A61N 2005/1095* (2013.01); *H05H 2007/002* (2013.01); *H05H 2007/007* (2013.01); *H05H 2007/043* (2013.01); *H05H 2007/045* (2013.01); *H05H 2277/10* (2013.01)

(56) References Cited

U.S. PATENT DOCUMENTS

| | | |
|---|---|---|
| 2,280,606 A | 4/1942 | Roberts |
| 2,492,324 A | 12/1949 | Salisbury |
| 2,615,129 A | 10/1952 | Mcmillan |
| 2,616,042 A | 10/1952 | Ray |
| 2,659,000 A | 11/1953 | Salisbury |
| 2,701,304 A | 2/1955 | Dickinson |
| 2,789,222 A | 4/1957 | Martin et al. |
| 2,958,327 A | 11/1960 | Geissmann |
| 3,024,379 A | 3/1962 | Verster |
| 3,175,131 A | 3/1965 | Burleigh et al. |
| 3,432,721 A | 3/1969 | Naydan et al. |
| 3,582,650 A | 6/1971 | Avery |
| 3,679,899 A | 7/1972 | Dimeff |
| 3,689,847 A | 9/1972 | Verster |
| 3,757,118 A | 9/1973 | Hodge et al. |
| 3,868,522 A | 2/1975 | Bigham et al. |
| 3,886,367 A | 5/1975 | Castle, Jr. |
| 3,925,676 A | 12/1975 | Bigham et al. |
| 3,955,089 A | 5/1976 | McIntyre et al. |
| 3,958,327 A | 5/1976 | Marancik et al. |
| 3,992,625 A | 11/1976 | Schmidt et al. |
| 4,038,622 A | 7/1977 | Purcell |
| 4,047,068 A | 9/1977 | Ress et al. |
| 4,112,306 A | 9/1978 | Nunan |
| 4,129,784 A | 12/1978 | Tschunt et al. |
| 4,139,777 A | 2/1979 | Rautenbach |
| 4,197,510 A | 4/1980 | Szu |
| 4,220,866 A | 9/1980 | Taumann et al. |
| 4,230,129 A | 10/1980 | LeVeen |
| 4,256,966 A | 3/1981 | Heinz |
| 4,293,772 A | 10/1981 | Stieber |
| 4,336,505 A | 6/1982 | Meyer |
| 4,342,060 A | 7/1982 | Gibson |
| 4,345,210 A | 8/1982 | Tran |
| 4,353,033 A | 10/1982 | Karasawa |
| 4,425,506 A | 1/1984 | Brown et al. |
| 4,490,616 A | 12/1984 | Cipollina et al. |
| 4,507,614 A | 3/1985 | Prono et al. |
| 4,507,616 A | 3/1985 | Blosser et al. |
| 4,589,126 A | 5/1986 | Augustsson et al. |
| 4,598,208 A | 7/1986 | Brunelli et al. |
| 4,628,523 A | 12/1986 | Heflin |
| 4,633,125 A | 12/1986 | Blosser et al. |
| 4,641,057 A | 2/1987 | Blosser et al. |
| 4,641,104 A | 2/1987 | Blosser et al. |
| 4,651,007 A | 3/1987 | Perusek et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,736,106 A | 4/1988 | Kashy et al. |
| 4,736,173 A | 4/1988 | Basil, Jr. et al. |
| 4,737,727 A | 4/1988 | Yamada et al. |
| 4,739,173 A | 4/1988 | Blosser et al. |
| 4,745,367 A | 5/1988 | Dustmann et al. |
| 4,754,147 A | 6/1988 | Maughan et al. |
| 4,763,483 A | 8/1988 | Olsen |
| 4,767,930 A | 8/1988 | Stieber et al. |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,845,371 A | 7/1989 | Stieber |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,894,541 A | 1/1990 | Ono |
| 4,896,206 A | 1/1990 | Denham |
| 4,902,993 A | 2/1990 | Krevet |
| 4,904,949 A | 2/1990 | Wilson |
| 4,905,267 A | 2/1990 | Miller et al. |
| 4,917,344 A | 4/1990 | Prechter et al. |
| 4,943,781 A | 7/1990 | Wilson et al. |
| 4,945,478 A | 7/1990 | Merickel et al. |
| 4,968,915 A | 11/1990 | Wilson et al. |
| 4,987,309 A | 1/1991 | Klasen et al. |
| 4,992,744 A | 2/1991 | Fujita et al. |
| 4,996,496 A | 2/1991 | Kitamura et al. |
| 5,006,759 A | 4/1991 | Krispel |
| 5,010,562 A | 4/1991 | Hemandez et al. |
| 5,012,111 A | 4/1991 | Ueda |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,046,078 A | 9/1991 | Hernandez et al. |
| 5,072,123 A | 12/1991 | Johnsen |
| 5,111,042 A | 5/1992 | Sullivan et al. |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,144,647 A | 9/1992 | Kikuchi |
| 5,148,032 A | 9/1992 | Hernandez |
| 5,166,531 A | 11/1992 | Huntzinger |
| 5,189,687 A | 2/1993 | Bova et al. |
| 5,191,706 A | 3/1993 | Cosden |
| 5,240,218 A | 8/1993 | Dye |
| 5,260,579 A | 11/1993 | Yasuda et al. |
| 5,260,581 A | 11/1993 | Lesyna et al. |
| 5,278,533 A | 1/1994 | Kawaguchi |
| 5,285,166 A | 2/1994 | Hiramoto et al. |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,401,973 A | 3/1995 | McKeown et al. |
| 5,405,235 A | 4/1995 | Lebre et al. |
| 5,434,420 A | 7/1995 | McKeown et al. |
| 5,440,133 A | 8/1995 | Moyers et al. |
| 5,451,794 A | 9/1995 | McKeown et al. |
| 5,461,773 A | 10/1995 | Kawaguchi |
| 5,463,291 A | 10/1995 | Carroll et al. |
| 5,464,411 A | 11/1995 | Schulte et al. |
| 5,492,922 A | 2/1996 | Palkowitz |
| 5,511,549 A | 4/1996 | Legg et al. |
| 5,521,469 A | 5/1996 | Laisne |
| 5,538,942 A | 7/1996 | Koyama et al. |
| 5,549,616 A | 8/1996 | Schulte et al. |
| 5,561,697 A | 10/1996 | Takafuji et al. |
| 5,585,642 A | 12/1996 | Britton et al. |
| 5,591,983 A * | 1/1997 | Yao .............. A61N 5/1045 378/152 |

(56) References Cited

U.S. PATENT DOCUMENTS

| | | |
|---|---|---|
| 5,633,747 A | 5/1997 | Nikoonahad |
| 5,635,721 A | 6/1997 | Bardi et al. |
| 5,668,371 A | 9/1997 | Deasy et al. |
| 5,672,878 A | 9/1997 | Yao |
| 5,691,679 A | 11/1997 | Ackermann et al. |
| 5,726,448 A | 3/1998 | Smith et al. |
| 5,727,554 A | 3/1998 | Kalend et al. |
| 5,730,745 A | 3/1998 | Schulte et al. |
| 5,748,703 A | 5/1998 | Cosman |
| 5,751,781 A | 5/1998 | Brown et al. |
| 5,764,723 A | 6/1998 | Weinberger et al. |
| 5,778,047 A | 7/1998 | Mansfield et al. |
| 5,783,914 A | 7/1998 | Hiramoto et al. |
| 5,784,431 A | 7/1998 | Kalend et al. |
| 5,797,924 A | 8/1998 | Schulte et al. |
| 5,811,944 A | 9/1998 | Sampayan et al. |
| 5,818,058 A | 10/1998 | Nakanishi et al. |
| 5,821,705 A | 10/1998 | Caporaso et al. |
| 5,825,845 A | 10/1998 | Blair et al. |
| 5,841,237 A | 11/1998 | Alton |
| 5,848,043 A | 12/1998 | Spath |
| 5,851,182 A | 12/1998 | Sahadevan |
| 5,866,912 A | 2/1999 | Slater et al. |
| 5,874,811 A | 2/1999 | Finlan et al. |
| 5,895,926 A | 4/1999 | Britton et al. |
| 5,920,601 A | 7/1999 | Nigg et al. |
| 5,929,458 A | 7/1999 | Nemezawa et al. |
| 5,963,615 A | 10/1999 | Egley et al. |
| 5,986,274 A | 11/1999 | Akiyama et al. |
| 5,993,373 A | 11/1999 | Nonaka et al. |
| 6,008,499 A | 12/1999 | Hiramoto et al. |
| 6,034,377 A | 3/2000 | Pu |
| 6,057,655 A | 5/2000 | Jongen |
| 6,061,426 A | 5/2000 | Linders et al. |
| 6,064,807 A | 5/2000 | Arai et al. |
| 6,066,851 A | 5/2000 | Madono et al. |
| 6,080,992 A | 6/2000 | Nonaka et al. |
| 6,087,670 A | 7/2000 | Hiramoto et al. |
| 6,087,672 A | 7/2000 | Matsuda et al. |
| 6,094,760 A | 8/2000 | Nonaka et al. |
| 6,118,848 A | 9/2000 | Reiffel |
| 6,140,021 A | 10/2000 | Nakasuji et al. |
| 6,144,875 A | 11/2000 | Schweikard et al. |
| 6,158,708 A | 12/2000 | Egley et al. |
| 6,207,952 B1 | 3/2001 | Kan et al. |
| 6,219,403 B1 | 4/2001 | Nishihara |
| 6,222,905 B1 | 4/2001 | Yoda et al. |
| 6,241,671 B1 | 6/2001 | Ritter et al. |
| 6,246,066 B1 | 6/2001 | Yuehu |
| 6,256,591 B1 | 7/2001 | Yoda et al. |
| 6,265,837 B1 | 7/2001 | Akiyama et al. |
| 6,268,610 B1 | 7/2001 | Pu |
| 6,278,239 B1 | 8/2001 | Caporaso et al. |
| 6,279,579 B1 | 8/2001 | Riazlat et al. |
| 6,307,914 B1 | 10/2001 | Kunleda et al. |
| 6,316,776 B1 | 11/2001 | Hiramoto et al. |
| 6,322,249 B1 * | 11/2001 | Wofford .............. A61N 5/1049 378/65 |
| 6,366,021 B1 | 4/2002 | Meddaugh et al. |
| 6,369,585 B2 | 4/2002 | Yao |
| 6,380,545 B1 | 4/2002 | Yan |
| 6,407,505 B1 | 6/2002 | Bertsche |
| 6,417,634 B1 | 7/2002 | Bergstrom |
| 6,433,336 B1 | 8/2002 | Jongen et al. |
| 6,433,349 B2 | 8/2002 | Akiyama et al. |
| 6,433,494 B1 | 8/2002 | Kulish et al. |
| 6,441,569 B1 | 8/2002 | Janzow |
| 6,443,349 B1 | 9/2002 | Van Der Burg |
| 6,459,769 B1 * | 10/2002 | Cosman .................. G21K 1/04 378/65 |
| 6,465,957 B1 | 10/2002 | Whitham et al. |
| 6,472,834 B2 | 10/2002 | Hiramoto et al. |
| 6,476,403 B1 | 11/2002 | Dolinskii et al. |
| 6,492,922 B1 | 12/2002 | New |
| 6,493,424 B2 | 12/2002 | Whitham |
| 6,498,444 B1 | 12/2002 | Hanna et al. |
| 6,501,981 B1 | 12/2002 | Schweikard et al. |
| 6,519,316 B1 | 2/2003 | Collins |
| 6,593,696 B2 | 7/2003 | Ding et al. |
| 6,594,336 B2 | 7/2003 | Nishizawa et al. |
| 6,600,164 B1 | 7/2003 | Badura et al. |
| 6,617,598 B1 | 9/2003 | Matsuda |
| 6,621,889 B1 | 9/2003 | Mostafavi |
| 6,630,675 B2 | 10/2003 | Ghelmansarai |
| 6,639,234 B1 | 10/2003 | Badura et al. |
| 6,646,383 B2 | 11/2003 | Bertsche et al. |
| 6,670,618 B1 | 12/2003 | Hartmann et al. |
| 6,683,162 B2 | 1/2004 | Scheinberg et al. |
| 6,683,318 B1 | 1/2004 | Haberer et al. |
| 6,683,426 B1 | 1/2004 | Kleeven |
| 6,693,283 B2 | 2/2004 | Eickhoff et al. |
| 6,710,362 B2 | 3/2004 | Kraft et al. |
| 6,713,773 B1 | 3/2004 | Lyons et al. |
| 6,713,976 B1 | 3/2004 | Zumoto et al. |
| 6,714,620 B2 | 3/2004 | Caflisch et al. |
| 6,717,162 B1 | 4/2004 | Jongen |
| 6,745,072 B1 | 6/2004 | Badura et al. |
| 6,757,355 B1 | 6/2004 | Siochi et al. |
| 6,769,806 B2 | 8/2004 | Moyers |
| 6,774,383 B2 | 8/2004 | Norimine et al. |
| 6,777,689 B2 | 8/2004 | Nelson |
| 6,777,700 B2 | 8/2004 | Yanagisawa et al. |
| 6,780,149 B1 | 8/2004 | Schulte |
| 6,792,078 B2 | 9/2004 | Kato et al. |
| 6,799,068 B1 | 9/2004 | Hartmann et al. |
| 6,800,866 B2 | 10/2004 | Amemiya et al. |
| 6,803,591 B2 | 10/2004 | Muramatsu et al. |
| 6,813,336 B1 | 11/2004 | Siochi |
| 6,814,694 B1 | 11/2004 | Pedroni |
| 6,819,743 B2 | 11/2004 | Kato et al. |
| 6,822,244 B2 | 11/2004 | Beloussov et al. |
| 6,823,045 B2 | 11/2004 | Kato et al. |
| 6,853,142 B2 | 2/2005 | Chistyakov |
| 6,853,703 B2 | 2/2005 | Svatos et al. |
| 6,864,770 B2 | 3/2005 | Nemoto et al. |
| 6,865,254 B2 | 3/2005 | Nafstadius |
| 6,873,123 B2 | 3/2005 | Marchand et al. |
| 6,878,951 B2 | 4/2005 | Ma |
| 6,891,177 B1 | 5/2005 | Kraft et al. |
| 6,891,924 B1 | 5/2005 | Yoda et al. |
| 6,894,300 B2 | 5/2005 | Reimoser et al. |
| 6,897,451 B2 | 5/2005 | Kaercher et al. |
| 6,907,105 B2 | 6/2005 | Otto et al. |
| 6,914,396 B1 | 7/2005 | Symons et al. |
| 6,931,100 B2 | 8/2005 | Kato et al. |
| 6,936,832 B2 | 8/2005 | Norimine et al. |
| 6,953,943 B2 | 10/2005 | Yanagisawa et al. |
| 6,965,116 B1 | 11/2005 | Wagner et al. |
| 6,969,194 B1 | 11/2005 | Nafstadius |
| 6,979,832 B2 | 12/2005 | Yanagisawa et al. |
| 6,984,835 B2 | 1/2006 | Harada |
| 6,992,312 B2 | 1/2006 | Yanagisawa et al. |
| 6,993,112 B2 | 1/2006 | Hesse |
| 6,998,604 B2 | 2/2006 | Nishizawa et al. |
| 7,008,105 B2 | 3/2006 | Amann et al. |
| 7,011,447 B2 | 3/2006 | Moyers |
| 7,012,267 B2 | 3/2006 | Moriyama et al. |
| 7,014,361 B1 | 3/2006 | Ein-Gal |
| 7,026,636 B2 | 4/2006 | Yanagisawa et al. |
| 7,038,403 B2 | 5/2006 | Mastrangeli et al. |
| 7,041,479 B2 | 5/2006 | Swartz et al. |
| 7,045,781 B2 | 5/2006 | Adamec et al. |
| 7,049,613 B2 | 5/2006 | Yanagisawa et al. |
| 7,053,389 B2 | 5/2006 | Yanagisawa et al. |
| 7,054,801 B2 | 5/2006 | Sakamoto et al. |
| 7,060,997 B2 | 6/2006 | Norimine et al. |
| 7,071,479 B2 | 7/2006 | Yanagisawa et al. |
| 7,073,508 B2 | 7/2006 | Moyers |
| 7,081,619 B2 | 7/2006 | Bashkirov et al. |
| 7,084,410 B2 | 8/2006 | Beloussov et al. |
| 7,091,478 B2 | 8/2006 | Haberer |
| 7,095,823 B2 | 8/2006 | Topolnjak et al. |
| 7,102,144 B2 | 9/2006 | Matsuda et al. |
| 7,122,811 B2 | 10/2006 | Matsuda et al. |

(56) References Cited

U.S. PATENT DOCUMENTS

| | | |
|---|---|---|
| 7,122,966 B2 | 10/2006 | Norling et al. |
| 7,122,978 B2 | 10/2006 | Nakanishi et al. |
| 7,135,678 B2 | 11/2006 | Wang et al. |
| 7,138,771 B2 | 11/2006 | Bechthold et al. |
| 7,154,107 B2 | 12/2006 | Yanagisawa et al. |
| 7,154,108 B2 | 12/2006 | Tadokoro et al. |
| 7,154,991 B2 | 12/2006 | Earnst et al. |
| 7,162,005 B2 | 1/2007 | Bjorkholm |
| 7,173,264 B2 | 2/2007 | Moriyama et al. |
| 7,173,265 B2 | 2/2007 | Miller et al. |
| 7,173,385 B2 | 2/2007 | Caporaso et al. |
| 7,186,991 B2 | 3/2007 | Kato et al. |
| 7,193,227 B2 | 3/2007 | Hiramoto et al. |
| 7,199,382 B2 | 4/2007 | Rigney et al. |
| 7,208,748 B2 | 4/2007 | Sliski et al. |
| 7,212,608 B2 | 5/2007 | Nagamine et al. |
| 7,212,609 B2 | 5/2007 | Nagamine et al. |
| 7,221,733 B1 | 5/2007 | Takai et al. |
| 7,227,161 B2 | 6/2007 | Matsuda et al. |
| 7,247,869 B2 | 7/2007 | Tadokoro et al. |
| 7,257,191 B2 | 8/2007 | Sommer |
| 7,259,529 B2 | 8/2007 | Tanaka |
| 7,262,424 B2 | 8/2007 | Moriyama et al. |
| 7,262,565 B2 | 8/2007 | Fujisawa |
| 7,268,358 B2 | 9/2007 | Ma et al. |
| 7,274,018 B2 | 9/2007 | Adamec et al. |
| 7,280,633 B2 | 10/2007 | Cheng et al. |
| 7,295,849 B2 | 11/2007 | Johnsen |
| 7,297,967 B2 | 11/2007 | Yanagisawa et al. |
| 7,301,162 B2 | 11/2007 | Matsuda et al. |
| 7,307,264 B2 | 12/2007 | Brusasco et al. |
| 7,317,192 B2 | 1/2008 | Ma |
| 7,318,805 B2 | 1/2008 | Schweikard et al. |
| 7,319,231 B2 | 1/2008 | Moriyama et al. |
| 7,319,336 B2 | 1/2008 | Baur et al. |
| 7,331,713 B2 | 2/2008 | Moyers |
| 7,332,880 B2 | 2/2008 | Ina et al. |
| 7,345,291 B2 | 3/2008 | Kats |
| 7,345,292 B2 | 3/2008 | Moriyama et al. |
| 7,348,557 B2 | 3/2008 | Armit |
| 7,348,579 B2 | 3/2008 | Pedroni |
| 7,351,988 B2 | 4/2008 | Naumann et al. |
| 7,355,189 B2 | 4/2008 | Yanagisawa et al. |
| 7,368,740 B2 | 5/2008 | Beloussov et al. |
| 7,372,053 B2 | 5/2008 | Yamashita et al. |
| 7,378,672 B2 | 5/2008 | Harada |
| 7,381,979 B2 | 6/2008 | Yamashita et al. |
| 7,386,099 B1 | 6/2008 | Kasper et al. |
| 7,397,054 B2 | 7/2008 | Natori et al. |
| 7,397,901 B1 | 7/2008 | Johnsen |
| 7,398,309 B2 | 7/2008 | Baumann et al. |
| 7,402,822 B2 | 7/2008 | Guertin et al. |
| 7,402,823 B2 | 7/2008 | Guertin et al. |
| 7,402,824 B2 | 7/2008 | Guertin et al. |
| 7,402,963 B2 | 7/2008 | Sliski et al. |
| 7,405,407 B2 | 7/2008 | Hiramoto et al. |
| 7,425,717 B2 | 9/2008 | Matsuda et al. |
| 7,432,516 B2 | 10/2008 | Peggs et al. |
| 7,439,528 B2 | 10/2008 | Nishiuchi et al. |
| 7,446,328 B2 | 11/2008 | Rigney et al. |
| 7,446,490 B2 | 11/2008 | Jongen et al. |
| 7,449,701 B2 | 11/2008 | Fujimaki et al. |
| 7,453,076 B2 | 11/2008 | Welch et al. |
| 7,465,944 B2 | 12/2008 | Ueno et al. |
| 7,466,085 B2 | 12/2008 | Nuti |
| 7,468,506 B2 | 12/2008 | Rogers et al. |
| 7,473,913 B2 | 1/2009 | Hermann et al. |
| 7,476,867 B2 | 1/2009 | Fritsch et al. |
| 7,476,883 B2 | 1/2009 | Nutt |
| 7,482,606 B2 | 1/2009 | Groezinger et al. |
| 7,492,556 B2 | 2/2009 | Atkins et al. |
| 7,507,975 B2 | 3/2009 | Mohr |
| 7,525,104 B2 | 4/2009 | Harada |
| 7,531,818 B2 | 5/2009 | Brahme |
| 7,541,905 B2 | 6/2009 | Antaya |
| 7,547,901 B2 | 6/2009 | Guertin et al. |
| 7,554,096 B2 | 6/2009 | Ward et al. |
| 7,554,097 B2 | 6/2009 | Ward et al. |
| 7,554,275 B2 | 6/2009 | Amaldi |
| 7,555,103 B2 | 6/2009 | Johnsen |
| 7,557,358 B2 | 7/2009 | Ward et al. |
| 7,557,359 B2 | 7/2009 | Ward et al. |
| 7,557,360 B2 | 7/2009 | Ward et al. |
| 7,557,361 B2 | 7/2009 | Ward et al. |
| 7,560,698 B2 | 7/2009 | Rietzel |
| 7,560,715 B2 | 7/2009 | Pedroni |
| 7,560,717 B2 | 7/2009 | Matsuda et al. |
| 7,567,694 B2 | 7/2009 | Lu et al. |
| 7,574,251 B2 | 8/2009 | Lu et al. |
| 7,576,499 B2 | 8/2009 | Caporaso et al. |
| 7,579,603 B2 | 8/2009 | Birgy et al. |
| 7,579,610 B2 | 8/2009 | Grozinger et al. |
| 7,582,866 B2 | 9/2009 | Furuhashi et al. |
| 7,582,885 B2 | 9/2009 | Katagiri et al. |
| 7,582,886 B2 | 9/2009 | Trbojevic |
| 7,586,112 B2 | 9/2009 | Chiba et al. |
| 7,598,497 B2 | 10/2009 | Yamamoto et al. |
| 7,609,009 B2 | 10/2009 | Tanaka et al. |
| 7,609,809 B2 | 10/2009 | Kapatoes et al. |
| 7,609,811 B1 | 10/2009 | Siljamaki et al. |
| 7,615,942 B2 | 11/2009 | Sanders et al. |
| 7,626,347 B2 | 12/2009 | Sliski et al. |
| 7,629,598 B2 | 12/2009 | Harada |
| 7,629,599 B2 | 12/2009 | Hashimoto |
| 7,639,853 B2 | 12/2009 | Olivera et al. |
| 7,639,854 B2 | 12/2009 | Schnarr et al. |
| 7,643,661 B2 | 1/2010 | Ruchala et al. |
| 7,656,258 B1 | 2/2010 | Antaya et al. |
| 7,659,521 B2 | 2/2010 | Pedroni |
| 7,659,528 B2 | 2/2010 | Uematsu |
| 7,668,291 B2 | 2/2010 | Nord et al. |
| 7,672,429 B2 | 3/2010 | Urano et al. |
| 7,679,049 B2 | 3/2010 | Rietzel |
| 7,679,073 B2 | 3/2010 | Urano et al. |
| 7,682,078 B2 | 3/2010 | Rietzel |
| 7,692,166 B2 | 4/2010 | Muraki et al. |
| 7,692,168 B2 | 4/2010 | Moriyama et al. |
| 7,696,499 B2 | 4/2010 | Miller et al. |
| 7,696,847 B2 | 4/2010 | Antaya |
| 7,701,677 B2 | 4/2010 | Schultz et al. |
| 7,709,818 B2 | 5/2010 | Matsuda et al. |
| 7,710,051 B2 | 5/2010 | Caporaso et al. |
| 7,718,982 B2 | 5/2010 | Sliski et al. |
| 7,723,036 B2 | 5/2010 | Racila et al. |
| 7,728,311 B2 | 6/2010 | Gall |
| 7,746,978 B2 | 6/2010 | Cheng et al. |
| 7,755,068 B2 | 7/2010 | Ma et al. |
| 7,755,305 B2 | 7/2010 | Umezawa et al. |
| 7,759,642 B2 | 7/2010 | Nir |
| 7,763,867 B2 | 7/2010 | Birgy et al. |
| 7,763,873 B2 | 7/2010 | Flynn et al. |
| 7,767,988 B2 | 8/2010 | Kaiser et al. |
| 7,770,231 B2 | 8/2010 | Prater et al. |
| 7,772,577 B2 | 8/2010 | Saito et al. |
| 7,773,723 B2 | 8/2010 | Nord et al. |
| 7,773,788 B2 | 8/2010 | Lu et al. |
| 7,778,488 B2 | 8/2010 | Nord et al. |
| 7,783,010 B2 | 8/2010 | Clayton |
| 7,784,124 B2 | 8/2010 | Long et al. |
| 7,784,127 B2 | 8/2010 | Kuro et al. |
| 7,786,433 B2 | 8/2010 | Gunzert-Marx et al. |
| 7,786,451 B2 | 8/2010 | Ward et al. |
| 7,786,452 B2 | 8/2010 | Ward et al. |
| 7,789,560 B2 | 9/2010 | Moyers |
| 7,791,051 B2 | 9/2010 | Beloussov et al. |
| 7,796,731 B2 | 9/2010 | Nord et al. |
| 7,801,269 B2 | 9/2010 | Cravens et al. |
| 7,801,270 B2 | 9/2010 | Nord et al. |
| 7,801,988 B2 | 9/2010 | Baumann et al. |
| 7,807,982 B2 | 10/2010 | Nishiuchi et al. |
| 7,809,107 B2 | 10/2010 | Nord et al. |
| 7,812,319 B2 | 10/2010 | Diehl et al. |
| 7,812,326 B2 | 10/2010 | Grozinger et al. |
| 7,816,657 B2 | 10/2010 | Hansmann et al. |

(56) References Cited

U.S. PATENT DOCUMENTS

| | | |
|---|---|---|
| 7,817,778 B2 | 10/2010 | Nord et al. |
| 7,817,836 B2 | 10/2010 | Chao et al. |
| 7,818,045 B2 | 10/2010 | Rietzel |
| 7,825,388 B2 | 11/2010 | Nihongi et al. |
| 7,826,593 B2 | 11/2010 | Svensson et al. |
| 7,834,334 B2 | 11/2010 | Grozinger et al. |
| 7,834,336 B2 | 11/2010 | Boeh et al. |
| 7,835,494 B2 | 11/2010 | Nord et al. |
| 7,835,502 B2 | 11/2010 | Spence et al. |
| 7,839,972 B2 | 11/2010 | Ruchala et al. |
| 7,839,973 B2 | 11/2010 | Nord et al. |
| 7,848,488 B2 | 12/2010 | Mansfield |
| 7,857,756 B2 | 12/2010 | Warren et al. |
| 7,858,592 B2 | 12/2010 | Shames et al. |
| 7,860,216 B2 | 12/2010 | Jongen et al. |
| 7,860,550 B2 | 12/2010 | Saracen et al. |
| 7,868,301 B2 | 1/2011 | Diehl |
| 7,875,846 B2 | 1/2011 | Gunzert-Marx et al. |
| 7,875,861 B2 | 1/2011 | Huttenberger et al. |
| 7,875,868 B2 | 1/2011 | Moriyama et al. |
| 7,881,431 B2 | 2/2011 | Aoi et al. |
| 7,894,574 B1 | 2/2011 | Nord et al. |
| 7,903,781 B2 | 3/2011 | Foland et al. |
| 7,906,769 B2 | 3/2011 | Blasche et al. |
| 7,907,987 B2 | 3/2011 | Dempsey |
| 7,914,734 B2 | 3/2011 | Livingston |
| 7,919,765 B2 | 4/2011 | Timmer |
| 7,920,040 B2 | 4/2011 | Antaya et al. |
| 7,920,675 B2 | 4/2011 | Lomax et al. |
| 7,928,415 B2 | 4/2011 | Bert et al. |
| 7,934,869 B2 | 5/2011 | Ivanov et al. |
| 7,939,809 B2 | 5/2011 | Balakin |
| 7,940,881 B2 | 5/2011 | Jongen et al. |
| 7,940,894 B2 | 5/2011 | Balakin |
| 7,943,913 B2 | 5/2011 | Balakin |
| 7,947,969 B2 | 5/2011 | Pu |
| 7,949,096 B2 | 5/2011 | Cheng et al. |
| 7,950,587 B2 | 5/2011 | Henson et al. |
| 7,953,205 B2 | 5/2011 | Balakin |
| 7,957,508 B2 | 6/2011 | Brooks et al. |
| 7,960,710 B2 | 6/2011 | Kruip et al. |
| 7,961,844 B2 | 6/2011 | Takeda et al. |
| 7,977,648 B2 | 7/2011 | Westerly et al. |
| 7,977,656 B2 | 7/2011 | Fujimaki et al. |
| 7,977,657 B2 | 7/2011 | Flynn et al. |
| 7,982,198 B2 | 7/2011 | Nishiuchi et al. |
| 7,982,416 B2 | 7/2011 | Tanaka et al. |
| 7,984,715 B2 | 7/2011 | Moyers |
| 7,986,768 B2 | 7/2011 | Nord et al. |
| 7,987,053 B2 | 7/2011 | Schaffner |
| 7,989,785 B2 | 8/2011 | Emhofer et al. |
| 7,990,524 B2 | 8/2011 | Jureller et al. |
| 7,997,553 B2 | 8/2011 | Sloan et al. |
| 8,002,466 B2 | 8/2011 | Von Neubeck et al. |
| 8,003,964 B2 | 8/2011 | Stark et al. |
| 8,009,803 B2 | 8/2011 | Nord et al. |
| 8,009,804 B2 | 8/2011 | Siljamaki et al. |
| 8,016,336 B2 | 9/2011 | Messinger et al. |
| 8,039,822 B2 | 10/2011 | Rietzel |
| 8,041,006 B2 | 10/2011 | Boyden et al. |
| 8,044,364 B2 | 10/2011 | Yamamoto |
| 8,045,679 B2 | 10/2011 | Balakin |
| 8,049,187 B2 | 11/2011 | Tachikawa |
| 8,053,508 B2 | 11/2011 | Korkut et al. |
| 8,053,739 B2 | 11/2011 | Rietzel |
| 8,053,745 B2 | 11/2011 | Moore |
| 8,053,746 B2 | 11/2011 | Timmer et al. |
| 8,063,381 B2 | 11/2011 | Tsoupas et al. |
| 8,067,748 B2 | 11/2011 | Balakin |
| 8,069,875 B2 | 12/2011 | Radovinsky et al. |
| 8,071,966 B2 | 12/2011 | Kaiser et al. |
| 8,080,801 B2 | 12/2011 | Safai |
| 8,085,899 B2 | 12/2011 | Nord et al. |
| 8,089,054 B2 | 1/2012 | Balakin |
| 8,090,074 B2 | 1/2012 | Filiberti et al. |
| 8,093,564 B2 | 1/2012 | Balakin |
| 8,093,568 B2 | 1/2012 | Mackie et al. |
| 8,111,125 B2 | 2/2012 | Antaya et al. |
| 8,129,694 B2 | 3/2012 | Balakin |
| 8,129,699 B2 | 3/2012 | Balakin |
| 8,144,832 B2 | 3/2012 | Balakin |
| 8,153,989 B2 | 4/2012 | Tachikawa et al. |
| 8,154,001 B2 | 4/2012 | Flynn et al. |
| 8,163,709 B2 | 4/2012 | Kodym et al. |
| 8,173,981 B2 | 5/2012 | Trbojevic |
| 8,178,859 B2 | 5/2012 | Balakin |
| 8,183,541 B2 | 5/2012 | Wilkens et al. |
| 8,188,688 B2 | 5/2012 | Balakin |
| 8,189,889 B2 | 5/2012 | Pearlstein et al. |
| 8,190,233 B2 | 5/2012 | Dempsey |
| 8,198,607 B2 | 6/2012 | Balakin |
| 8,207,656 B2 | 6/2012 | Baumgartner et al. |
| 8,222,613 B2 | 7/2012 | Tajiri et al. |
| 8,227,768 B2 | 7/2012 | Smick et al. |
| 8,229,072 B2 | 7/2012 | Balakin |
| 8,232,536 B2 | 7/2012 | Harada |
| 8,238,513 B2 | 8/2012 | Ma |
| 8,253,121 B2 | 8/2012 | Gnutzmann et al. |
| 8,254,521 B2 | 8/2012 | Brooks et al. |
| 8,263,954 B2 | 9/2012 | Iwata |
| 8,283,645 B2 | 10/2012 | Guneysel |
| 8,288,742 B2 | 10/2012 | Balakin |
| 8,291,717 B2 | 10/2012 | Radovinsky et al. |
| 8,294,127 B2 | 10/2012 | Tachibana |
| 8,304,725 B2 | 11/2012 | Komuro et al. |
| 8,304,750 B2 | 11/2012 | Preikszas et al. |
| 8,309,941 B2 | 11/2012 | Balakin |
| 8,330,132 B2 | 12/2012 | Guertin et al. |
| 8,334,520 B2 | 12/2012 | Otaka et al. |
| 8,335,397 B2 | 12/2012 | Takane et al. |
| 8,344,340 B2 | 1/2013 | Gall et al. |
| 8,350,214 B2 | 1/2013 | Otaki et al. |
| 8,351,571 B2 | 1/2013 | Brinks et al. |
| 8,354,656 B2 | 1/2013 | Beloussov et al. |
| 8,368,038 B2 | 2/2013 | Balakin |
| 8,368,043 B2 | 2/2013 | Havelange et al. |
| 8,373,143 B2 | 2/2013 | Balakin |
| 8,373,145 B2 | 2/2013 | Balakin |
| 8,373,146 B2 | 2/2013 | Balakin |
| 8,374,314 B2 | 2/2013 | Balakin |
| 8,378,299 B2 | 2/2013 | Frosien |
| 8,378,311 B2 | 2/2013 | Balakin |
| 8,378,312 B1 | 2/2013 | Gordon et al. |
| 8,378,321 B2 | 2/2013 | Balakin |
| 8,382,943 B2 | 2/2013 | Clark |
| 8,384,053 B2 | 2/2013 | Balakin |
| 8,389,949 B2 | 3/2013 | Harada et al. |
| 8,399,866 B2 | 3/2013 | Balakin |
| 8,405,042 B2 | 3/2013 | Honda et al. |
| 8,405,056 B2 | 3/2013 | Amaldi et al. |
| 8,415,643 B2 | 4/2013 | Balakin |
| 8,416,918 B2 | 4/2013 | Nord et al. |
| 8,421,041 B2 | 4/2013 | Balakin |
| 8,426,833 B2 | 4/2013 | Trbojevic |
| 8,436,323 B2 | 5/2013 | Iseki et al. |
| 8,436,325 B2 | 5/2013 | Noda et al. |
| 8,436,327 B2 | 5/2013 | Balakin |
| 8,440,987 B2 | 5/2013 | Stephani et al. |
| 8,445,872 B2 | 5/2013 | Behrens et al. |
| 8,459,714 B2 | 6/2013 | Pomper et al. |
| 8,461,559 B2 | 6/2013 | Lomax |
| 8,466,441 B2 | 6/2013 | Iwata et al. |
| 8,472,583 B2 | 6/2013 | Star-Lack et al. |
| 8,481,951 B2 | 7/2013 | Jongen et al. |
| 8,483,357 B2 | 7/2013 | Siljamaki et al. |
| 8,487,278 B2 | 7/2013 | Balakin |
| 8,487,282 B2 | 7/2013 | Iseki et al. |
| 8,507,195 B2 | 8/2013 | Richer et al. |
| 8,519,365 B2 | 8/2013 | Balakin |
| 8,525,419 B2 | 9/2013 | Smith et al. |
| 8,525,447 B2 | 9/2013 | Antaya |
| 8,525,448 B2 | 9/2013 | Tanaka et al. |
| 8,536,548 B2 | 9/2013 | Otani et al. |
| 8,541,762 B2 | 9/2013 | Claereboudt et al. |

(56) References Cited

U.S. PATENT DOCUMENTS

| | | |
|---|---|---|
| 8,546,769 B2 | 10/2013 | Uno |
| 8,552,406 B2 | 10/2013 | Phaneuf et al. |
| 8,552,408 B2 | 10/2013 | Hanawa et al. |
| 8,558,461 B2 | 10/2013 | Poehlmann-Martins et al. |
| 8,558,485 B2 | 10/2013 | Antaya |
| 8,565,377 B2 | 10/2013 | Robar et al. |
| 8,569,717 B2 | 10/2013 | Balakin |
| 8,575,563 B2 | 11/2013 | Cameron et al. |
| 8,575,564 B2 | 11/2013 | Iwala |
| 8,575,579 B2 | 11/2013 | Moskvin et al. |
| 8,581,215 B2 | 11/2013 | Balakin |
| 8,581,218 B2 | 11/2013 | Fujimoto et al. |
| 8,581,523 B2 | 11/2013 | Gall et al. |
| 8,581,525 B2 | 11/2013 | Antaya et al. |
| 8,586,948 B2 | 11/2013 | Pu et al. |
| 8,598,543 B2 | 12/2013 | Balakin |
| 8,601,116 B2 | 12/2013 | Baumann et al. |
| 8,604,454 B2 | 12/2013 | Guertin et al. |
| 8,613,694 B2 | 12/2013 | Walsh |
| 8,614,554 B2 | 12/2013 | Balakin |
| 8,614,612 B2 | 12/2013 | Antaya et al. |
| 8,618,519 B2 | 12/2013 | Ueda |
| 8,618,521 B2 | 12/2013 | Loo et al. |
| 8,619,242 B2 | 12/2013 | Suzuki |
| 8,625,739 B2 | 1/2014 | Balakin |
| 8,627,822 B2 | 1/2014 | Balakin |
| 8,632,448 B1 | 1/2014 | Schulte et al. |
| 8,633,160 B2 | 1/2014 | Belmares et al. |
| 8,637,818 B2 | 1/2014 | Balakin |
| 8,637,839 B2 | 1/2014 | Brauer |
| 8,824,528 B2 | 1/2014 | Balakin |
| 8,642,978 B2 | 2/2014 | Balakin |
| 8,643,314 B2 | 2/2014 | Touchi |
| 8,644,571 B1 | 2/2014 | Schulte et al. |
| 8,653,314 B2 | 2/2014 | Pelati et al. |
| 8,653,473 B2 | 2/2014 | Yajima |
| 8,657,354 B2 | 2/2014 | Pomper et al. |
| 8,657,743 B2 | 2/2014 | Rietzel et al. |
| 8,688,197 B2 | 4/2014 | Balakin |
| 8,702,578 B2 | 4/2014 | Fahrig et al. |
| 8,710,462 B2 | 4/2014 | Balakin |
| 8,712,011 B2 | 4/2014 | Robar et al. |
| 8,716,663 B2 | 5/2014 | Brusasco et al. |
| 8,718,231 B2 | 5/2014 | Balakin |
| 8,735,848 B2 | 5/2014 | Asaba |
| 8,748,852 B2 | 6/2014 | Jongen |
| 8,750,453 B2 | 6/2014 | Cheng et al. |
| 8,754,386 B2 | 6/2014 | Iwata |
| 8,766,217 B2 | 7/2014 | Balakin |
| 8,766,218 B2 | 7/2014 | Jongen |
| 8,771,754 B2 | 7/2014 | Hallahan |
| 8,791,435 B2 | 7/2014 | Balakin |
| 8,791,656 B1 | 7/2014 | Zwart et al. |
| 8,796,648 B2 | 8/2014 | Fujimoto et al. |
| 8,822,965 B2 | 9/2014 | Asaba |
| 8,835,885 B2 | 9/2014 | Ogasawara |
| 8,847,179 B2 | 9/2014 | Fujitaka et al. |
| 8,859,264 B2 | 10/2014 | Bert et al. |
| 8,866,109 B2 | 10/2014 | Sasai |
| 8,890,097 B2 | 11/2014 | Iwata |
| 8,896,239 B2 | 11/2014 | Balakin |
| 8,897,857 B2 | 11/2014 | Tome et al. |
| 8,901,509 B2 | 12/2014 | Balakin |
| 8,901,520 B2 | 12/2014 | Tachibana et al. |
| 8,907,309 B2 | 12/2014 | Spotts |
| 8,907,311 B2 | 12/2014 | Gall et al. |
| 8,907,594 B2 | 12/2014 | Begg et al. |
| 8,916,838 B2 | 12/2014 | Claereboudt et al. |
| 8,916,841 B2 | 12/2014 | Totake et al. |
| 8,916,843 B2 | 12/2014 | Gall et al. |
| 8,927,946 B2 | 1/2015 | Behrens et al. |
| 8,927,950 B2 | 1/2015 | Gall et al. |
| 8,933,650 B2 | 1/2015 | O'Neal, III et al. |
| 8,941,083 B2 | 1/2015 | Stark et al. |
| 8,941,084 B2 | 1/2015 | Balakin |
| 8,941,086 B2 | 1/2015 | Yajima |
| 8,947,021 B2 | 2/2015 | Tsutsul |
| 8,948,341 B2 | 2/2015 | Beckman |
| 8,952,343 B2 | 2/2015 | Stephani et al. |
| 8,952,634 B2 | 2/2015 | Sliski et al. |
| 8,957,396 B2 | 2/2015 | Balakin |
| 8,963,111 B2 | 2/2015 | Claereboudt et al. |
| 8,963,112 B1 | 2/2015 | Balakin |
| 8,964,936 B2 | 2/2015 | Brooks et al. |
| 8,969,834 B2 | 3/2015 | Balakin |
| 8,970,137 B2 | 3/2015 | Gall et al. |
| 8,971,363 B2 | 3/2015 | Levecq et al. |
| 8,975,600 B2 | 3/2015 | Balakin |
| 8,975,602 B2 | 3/2015 | Huber et al. |
| 8,975,836 B2 | 3/2015 | Bromberg et al. |
| 8,986,186 B2 | 3/2015 | Zhang et al. |
| 8,993,522 B2 | 3/2015 | Vidyasagar et al. |
| 9,006,693 B2 | 4/2015 | Sasai |
| 9,007,740 B2 | 4/2015 | Touchi |
| 9,012,832 B2 | 4/2015 | Bert et al. |
| 9,012,866 B2 | 4/2015 | Benna et al. |
| 9,012,873 B2 | 4/2015 | Fujimoto et al. |
| 9,018,601 B2 | 4/2015 | Balakin |
| 9,018,603 B2 | 4/2015 | Loo et al. |
| 9,024,256 B2 | 5/2015 | Ruan et al. |
| 9,029,760 B2 | 5/2015 | Beddar et al. |
| 9,044,600 B2 | 6/2015 | Balakin |
| 9,056,199 B2 | 6/2015 | Balakin |
| 9,058,910 B2 | 6/2015 | Balakin |
| 9,060,998 B2 | 6/2015 | Stockfleth |
| 9,061,142 B2 | 6/2015 | Vilsmeier |
| 9,061,143 B2 | 6/2015 | Sasai et al. |
| 9,084,887 B2 | 7/2015 | Schulte et al. |
| 9,084,890 B2 | 7/2015 | Iwata |
| 9,089,696 B2 | 7/2015 | Verhaegen et al. |
| 9,093,209 B2 | 7/2015 | Jongen |
| 9,095,040 B2 | 7/2015 | Balakin |
| 9,108,050 B2 | 8/2015 | Bula et al. |
| 9,114,253 B2 | 8/2015 | Dempsey |
| 9,142,385 B1 | 9/2015 | Iwanaga |
| 9,155,186 B2 | 10/2015 | Zwart et al. |
| 9,155,908 B2 | 10/2015 | Meltsner et al. |
| 9,185,789 B2 | 11/2015 | Zwart et al. |
| 9,186,525 B2 | 11/2015 | Prieels et al. |
| 9,188,685 B2 | 11/2015 | Takayanagi et al. |
| 9,196,082 B2 | 11/2015 | Pearlstein et al. |
| 9,220,920 B2 | 12/2015 | Schulte et al. |
| 9,220,923 B2 | 12/2015 | Yajima et al. |
| 9,237,640 B2 | 1/2016 | Abs et al. |
| 9,237,642 B2 | 1/2016 | Kleeven |
| 9,245,336 B2 | 1/2016 | Mallya et al. |
| 9,254,396 B2 | 2/2016 | Mihaylov |
| 9,259,155 B2 | 2/2016 | Bharat et al. |
| 9,271,385 B2 | 2/2016 | Verbruggen et al. |
| 9,283,406 B2 | 3/2016 | Prieels |
| 9,283,407 B2 | 3/2016 | Benna et al. |
| 9,289,140 B2 | 3/2016 | Ross et al. |
| 9,289,624 B2 | 3/2016 | Jongen |
| 9,297,912 B2 | 3/2016 | Campbell et al. |
| 9,301,384 B2 | 3/2016 | Zwart et al. |
| 9,302,121 B2 | 4/2016 | Totake et al. |
| 9,305,742 B2 | 4/2016 | Aptaker et al. |
| 9,324,468 B2 | 4/2016 | Mansfield et al. |
| 9,355,784 B2 | 5/2016 | Abs |
| 9,364,688 B2 | 6/2016 | Pausch et al. |
| 9,370,089 B2 | 6/2016 | Ungaro et al. |
| 9,381,379 B2 | 7/2016 | Beckman |
| 9,393,443 B2 | 7/2016 | Fujimoto et al. |
| 9,417,302 B2 | 8/2016 | Kuhn |
| 9,451,688 B2 | 9/2016 | Jongen |
| 9,451,689 B2 | 9/2016 | Tsutsui |
| 9,452,300 B2 | 9/2016 | Anferov |
| 9,452,301 B2 | 9/2016 | Gall et al. |
| 9,468,608 B2 | 10/2016 | Lin et al. |
| 9,492,684 B2 | 11/2016 | Takayanagi et al. |
| 9,723,705 B2 | 8/2017 | Gall et al. |
| 9,776,017 B2 | 10/2017 | Flynn et al. |
| 9,962,560 B2 | 5/2018 | Zwart et al. |
| 9,999,787 B1 * | 6/2018 | Ruohonen ............ A61N 5/1045 |

(56) References Cited

U.S. PATENT DOCUMENTS

| | | | |
|---|---|---|---|
| 10,258,810 B2 | 4/2019 | Zwart et al. |
| 2001/0022502 A1 | 9/2001 | Akiyama et al. |
| 2002/0058007 A1 | 5/2002 | Scheinberg et al. |
| 2002/0101959 A1 | 8/2002 | Kato et al. |
| 2002/0172317 A1 | 11/2002 | Maksimchuk et al. |
| 2003/0048080 A1 | 3/2003 | Amemiya et al. |
| 2003/0125622 A1 | 7/2003 | Schweikard et al. |
| 2003/0136924 A1 | 7/2003 | Kraft et al. |
| 2003/0152197 A1 | 8/2003 | Moyers |
| 2003/0163015 A1 | 8/2003 | Yanagisawa et al. |
| 2003/0183779 A1 | 10/2003 | Norimine et al. |
| 2003/0234369 A1 | 12/2003 | Glukhoy |
| 2004/0000650 A1 | 1/2004 | Yanagisawa et al. |
| 2004/0017888 A1 | 1/2004 | Seppi et al. |
| 2004/0056212 A1 | 3/2004 | Yanagisawa et al. |
| 2004/0061077 A1 | 4/2004 | Muramatsu et al. |
| 2004/0061078 A1 | 4/2004 | Muramatsu et al. |
| 2004/0085023 A1 | 5/2004 | Chistyakov |
| 2004/0098445 A1 | 5/2004 | Baumann et al. |
| 2004/0111134 A1 | 6/2004 | Muramatsu et al. |
| 2004/0118081 A1 | 6/2004 | Reimoser et al. |
| 2004/0149934 A1 | 8/2004 | Yanagisawa et al. |
| 2004/0155206 A1 | 8/2004 | Marchand et al. |
| 2004/0159795 A1 | 8/2004 | Kaercher et al. |
| 2004/0164254 A1 | 8/2004 | Beloussov et al. |
| 2004/0173763 A1 | 9/2004 | Moriyama et al. |
| 2004/0174958 A1 | 9/2004 | Moriyama et al. |
| 2004/0183033 A1 | 9/2004 | Moriyama et al. |
| 2004/0183035 A1 | 9/2004 | Yanagisawa et al. |
| 2004/0190880 A1 | 9/2004 | Chang |
| 2004/0200982 A1 | 10/2004 | Moriyama et al. |
| 2004/0200983 A1 | 10/2004 | Fujimaki et al. |
| 2004/0213381 A1 | 10/2004 | Harada |
| 2004/0227104 A1 | 11/2004 | Matsuda et al. |
| 2004/0232356 A1 | 11/2004 | Norimine et al. |
| 2004/0240626 A1 | 12/2004 | Moyers |
| 2005/0008123 A1 | 1/2005 | Topolnjak et al. |
| 2005/0029472 A1 | 2/2005 | Ueno et al. |
| 2005/0051740 A1 | 3/2005 | Yanagisawa et al. |
| 2005/0058245 A1 | 3/2005 | Ein-Gal |
| 2005/0072940 A1 | 4/2005 | Beloussov et al. |
| 2005/0079235 A1 | 4/2005 | Stockfleth |
| 2005/0087700 A1 | 4/2005 | Tadokoro et al. |
| 2005/0089141 A1 | 4/2005 | Brown |
| 2005/0099145 A1 | 5/2005 | Nishiuchi et al. |
| 2005/0113327 A1 | 5/2005 | Roiz et al. |
| 2005/0127306 A1 | 6/2005 | Yanagisawa et al. |
| 2005/0139787 A1 | 6/2005 | Chiba et al. |
| 2005/0161618 A1 | 7/2005 | Pedroni |
| 2005/0167616 A1 | 8/2005 | Yanagisawa et al. |
| 2005/0184686 A1 | 8/2005 | Caporaso et al. |
| 2005/0186179 A1 | 8/2005 | Harats et al. |
| 2005/0205806 A1 | 9/2005 | Tadokoro et al. |
| 2005/0228255 A1 | 10/2005 | Saracen et al. |
| 2005/0231138 A1 | 10/2005 | Nakanishi et al. |
| 2005/0234327 A1 | 10/2005 | Saracen et al. |
| 2005/0247890 A1 | 11/2005 | Norimine et al. |
| 2005/0259779 A1 | 11/2005 | Abraham-Fuchs et al. |
| 2006/0017015 A1 | 1/2006 | Sliski et al. |
| 2006/0033042 A1 | 2/2006 | Groezinger et al. |
| 2006/0067468 A1 | 3/2006 | Rietzel |
| 2006/0067480 A1* | 3/2006 | Juschka ............... G21K 1/046 378/150 |
| 2006/0126792 A1 | 6/2006 | Li |
| 2006/0127879 A1 | 6/2006 | Fuccione |
| 2006/0145088 A1 | 7/2006 | Ma |
| 2006/0175991 A1 | 8/2006 | Fujisawa |
| 2006/0192146 A1 | 8/2006 | Yanagisawa et al. |
| 2006/0204478 A1 | 9/2006 | Harats et al. |
| 2006/0219948 A1 | 10/2006 | Ueno et al. |
| 2006/0284562 A1 | 12/2006 | Hruby et al. |
| 2007/0001128 A1 | 1/2007 | Sliski et al. |
| 2007/0013273 A1 | 1/2007 | Albert et al. |
| 2007/0014654 A1 | 1/2007 | Haverfield et al. |
| 2007/0018120 A1 | 1/2007 | Beloussov et al. |
| 2007/0023699 A1 | 2/2007 | Yamashita et al. |
| 2007/0029510 A1 | 2/2007 | Hermann et al. |
| 2007/0031337 A1 | 2/2007 | Schulte |
| 2007/0034812 A1 | 2/2007 | Ma et al. |
| 2007/0051904 A1 | 3/2007 | Kaiser et al. |
| 2007/0053484 A1 | 3/2007 | Chiba et al. |
| 2007/0059387 A1 | 3/2007 | Stockfleth |
| 2007/0075273 A1 | 4/2007 | Birgy et al. |
| 2007/0083101 A1 | 4/2007 | Rietzel |
| 2007/0092812 A1 | 4/2007 | Caporaso et al. |
| 2007/0108922 A1 | 5/2007 | Amaldi |
| 2007/0114464 A1 | 5/2007 | Birgy et al. |
| 2007/0114471 A1 | 5/2007 | Birgy et al. |
| 2007/0114945 A1 | 5/2007 | Mattaboni et al. |
| 2007/0145916 A1 | 6/2007 | Caporaso et al. |
| 2007/0171015 A1 | 7/2007 | Antaya |
| 2007/0181519 A1 | 8/2007 | Khoshnevis |
| 2007/0217575 A1 | 9/2007 | Kaiser et al. |
| 2007/0262269 A1 | 11/2007 | Trbojevic |
| 2007/0284548 A1 | 12/2007 | Kaiser et al. |
| 2008/0023644 A1 | 1/2008 | Pedroni |
| 2008/0029706 A1 | 2/2008 | Kaiser et al. |
| 2008/0031414 A1 | 2/2008 | Coppens |
| 2008/0049896 A1* | 2/2008 | Kuduvalli ............ A61N 5/1049 378/65 |
| 2008/0049897 A1* | 2/2008 | Molloy ................. A61N 5/1042 378/65 |
| 2008/0061241 A1 | 3/2008 | Rietzel |
| 2008/0063147 A1 | 3/2008 | Juschka et al. |
| 2008/0073591 A1 | 3/2008 | Mohr |
| 2008/0078942 A1 | 4/2008 | Rietzel |
| 2008/0093567 A1 | 4/2008 | Gall |
| 2008/0123816 A1 | 5/2008 | Mori et al. |
| 2008/0131419 A1 | 6/2008 | Roiz et al. |
| 2008/0159478 A1 | 7/2008 | Keall et al. |
| 2008/0179544 A1 | 7/2008 | Kaiser et al. |
| 2008/0191142 A1 | 8/2008 | Pedroni |
| 2008/0191152 A1 | 8/2008 | Grozinger et al. |
| 2008/0205599 A1 | 8/2008 | Hashimoto |
| 2008/0218102 A1 | 9/2008 | Sliski et al. |
| 2008/0219407 A1 | 9/2008 | Kaiser et al. |
| 2008/0219410 A1 | 9/2008 | Gunzert-Marx et al. |
| 2008/0219411 A1 | 9/2008 | Gunzert-Marx et al. |
| 2008/0237494 A1 | 10/2008 | Beloussov et al. |
| 2008/0237495 A1 | 10/2008 | Grozinger et al. |
| 2008/0267349 A1 | 10/2008 | Rietzel |
| 2008/0270517 A1 | 10/2008 | Baumann et al. |
| 2008/0272284 A1 | 11/2008 | Rietzel |
| 2008/0290299 A1 | 11/2008 | Hansmann et al. |
| 2008/0298550 A1 | 12/2008 | Otto |
| 2008/0301872 A1 | 12/2008 | Fahrig et al. |
| 2008/0315111 A1 | 12/2008 | Sommer |
| 2009/0008575 A1 | 1/2009 | Okazaki et al. |
| 2009/0032742 A1 | 2/2009 | Kaiser et al. |
| 2009/0050819 A1 | 2/2009 | Ma et al. |
| 2009/0060130 A1 | 3/2009 | Wilkens et al. |
| 2009/0065717 A1 | 3/2009 | Kaiser et al. |
| 2009/0069640 A1 | 3/2009 | Rietzel et al. |
| 2009/0077209 A1 | 3/2009 | Schneider |
| 2009/0096179 A1 | 4/2009 | Stark et al. |
| 2009/0098145 A1 | 4/2009 | Mata et al. |
| 2009/0101833 A1 | 4/2009 | Emhofer et al. |
| 2009/0114847 A1 | 5/2009 | Grozinger et al. |
| 2009/0140671 A1 | 6/2009 | O'Neal, III et al. |
| 2009/0140672 A1 | 6/2009 | Gall et al. |
| 2009/0175414 A1 | 7/2009 | Messinger et al. |
| 2009/0189095 A1 | 7/2009 | Flynn et al. |
| 2009/0200483 A1 | 8/2009 | Gall et al. |
| 2009/0230327 A1 | 9/2009 | Rietzel |
| 2009/0234237 A1 | 9/2009 | Ross et al. |
| 2009/0242789 A1 | 10/2009 | Tachikawa |
| 2009/0261275 A1 | 10/2009 | Rietzel |
| 2009/0274269 A1 | 11/2009 | Foland et al. |
| 2009/0298885 A1 | 12/2009 | Boeh et al. |
| 2009/0309046 A1 | 12/2009 | Balakin |
| 2009/0309047 A1 | 12/2009 | Gunzert-Marx et al. |
| 2009/0309520 A1 | 12/2009 | Balakin |
| 2009/0314960 A1 | 12/2009 | Balakin |
| 2009/0314961 A1 | 12/2009 | Balakin |

(56) References Cited

U.S. PATENT DOCUMENTS

| | | |
|---|---|---|
| 2009/0321656 A1 | 12/2009 | Rietzel et al. |
| 2010/0006106 A1 | 1/2010 | Balakin |
| 2010/0006770 A1 | 1/2010 | Balakin |
| 2010/0008466 A1 | 1/2010 | Balakin |
| 2010/0014639 A1 | 1/2010 | Balakin |
| 2010/0014640 A1 | 1/2010 | Balakin |
| 2010/0020932 A1 | 1/2010 | Yi et al. |
| 2010/0027745 A1 | 2/2010 | Balakin |
| 2010/0034357 A1* | 2/2010 | Svesson .............. G21K 1/04 378/152 |
| 2010/0038552 A1 | 2/2010 | Trbojevic |
| 2010/0045213 A1 | 2/2010 | Sliski et al. |
| 2010/0046697 A1 | 2/2010 | Balakin |
| 2010/0046713 A1 | 2/2010 | Nord et al. |
| 2010/0060209 A1 | 3/2010 | Balakin |
| 2010/0090122 A1 | 4/2010 | Balakin |
| 2010/0091948 A1 | 4/2010 | Balakin |
| 2010/0126964 A1 | 5/2010 | Smith et al. |
| 2010/0127184 A1 | 5/2010 | Balakin |
| 2010/0128846 A1 | 5/2010 | Balakin |
| 2010/0133444 A1 | 6/2010 | Balakin |
| 2010/0133446 A1 | 6/2010 | Balakin |
| 2010/0141183 A1 | 6/2010 | Balakin |
| 2010/0166150 A1 | 7/2010 | Perkins et al. |
| 2010/0171045 A1 | 7/2010 | Guneysel |
| 2010/0171447 A1 | 7/2010 | Balakin |
| 2010/0176309 A1 | 7/2010 | Mackie et al. |
| 2010/0207552 A1 | 8/2010 | Balakin |
| 2010/0230617 A1 | 9/2010 | Gall |
| 2010/0230620 A1 | 9/2010 | Tsoupas et al. |
| 2010/0243911 A1 | 9/2010 | Fujii et al. |
| 2010/0252754 A1 | 10/2010 | Brown et al. |
| 2010/0264327 A1 | 10/2010 | Bonig et al. |
| 2010/0266100 A1 | 10/2010 | Balakin |
| 2010/0288945 A1 | 11/2010 | Gnutzmann et al. |
| 2010/0296534 A1 | 11/2010 | Levecq et al. |
| 2010/0301235 A1 | 12/2010 | Bert et al. |
| 2010/0308235 A1 | 12/2010 | Sliski et al. |
| 2010/0320404 A1 | 12/2010 | Tanke |
| 2010/0327187 A1 | 12/2010 | Beloussov et al. |
| 2011/0006214 A1 | 1/2011 | Bonig |
| 2011/0009736 A1 | 1/2011 | Maltz et al. |
| 2011/0011729 A1 | 1/2011 | Poehlmann-Martins et al. |
| 2011/0027853 A1 | 2/2011 | Bert et al. |
| 2011/0047469 A1 | 2/2011 | Baumann et al. |
| 2011/0049396 A1 | 3/2011 | Furth et al. |
| 2011/0051891 A1 | 3/2011 | O'Connor et al. |
| 2011/0051893 A1* | 3/2011 | McNutt .............. A61N 5/1031 600/407 |
| 2011/0101236 A1 | 5/2011 | Cameron et al. |
| 2011/0118529 A1 | 5/2011 | Balakin |
| 2011/0118531 A1 | 5/2011 | Balakin |
| 2011/0124976 A1 | 5/2011 | Sabczynski et al. |
| 2011/0127443 A1 | 6/2011 | Comer et al. |
| 2011/0147608 A1 | 6/2011 | Balakin |
| 2011/0150180 A1 | 6/2011 | Balakin |
| 2011/0166219 A1 | 7/2011 | Stockfleth |
| 2011/0180720 A1 | 7/2011 | Balakin |
| 2011/0180731 A1 | 7/2011 | Welsh |
| 2011/0182410 A1 | 7/2011 | Balakin |
| 2011/0186720 A1 | 8/2011 | Jongen et al. |
| 2011/0196223 A1 | 8/2011 | Balakin |
| 2011/0200170 A1* | 8/2011 | Nord .............. A61N 5/1036 378/65 |
| 2011/0204262 A1 | 8/2011 | Pu et al. |
| 2011/0214588 A1 | 9/2011 | Grubling et al. |
| 2011/0218430 A1 | 9/2011 | Balakin |
| 2011/0220794 A1 | 9/2011 | Censor et al. |
| 2011/0220798 A1 | 9/2011 | Baurichter et al. |
| 2011/0231147 A1 | 9/2011 | Takayanagi et al. |
| 2011/0233423 A1* | 9/2011 | Balakin .............. G21K 1/087 250/492.1 |
| 2011/0238440 A1 | 9/2011 | Leuschner |
| 2011/0248188 A1 | 10/2011 | Brusasco et al. |
| 2011/0278477 A1 | 11/2011 | Balakin |
| 2011/0284757 A1 | 11/2011 | Butuceanu et al. |
| 2011/0284760 A1 | 11/2011 | Balakin |
| 2011/0285327 A1 | 11/2011 | Begg et al. |
| 2011/0297850 A1 | 12/2011 | Claereboudt et al. |
| 2011/0299657 A1 | 12/2011 | Havelange et al. |
| 2011/0299919 A1 | 12/2011 | Stark et al. |
| 2011/0303858 A1 | 12/2011 | Bert et al. |
| 2011/0306870 A1 | 12/2011 | Kuhn |
| 2011/0313232 A1 | 12/2011 | Balakin |
| 2012/0001085 A1 | 1/2012 | Fujimoto et al. |
| 2012/0043481 A1 | 2/2012 | Mansfield et al. |
| 2012/0043482 A1 | 2/2012 | Prince et al. |
| 2012/0056109 A1 | 3/2012 | Lomax |
| 2012/0058099 A1 | 3/2012 | Behrens et al. |
| 2012/0069961 A1 | 3/2012 | Pomper et al. |
| 2012/0077748 A1 | 3/2012 | Vidyasagar et al. |
| 2012/0099704 A1 | 4/2012 | Ruan et al. |
| 2012/0112092 A1 | 5/2012 | Pomper et al. |
| 2012/0119114 A1 | 5/2012 | Brauer |
| 2012/0136194 A1 | 5/2012 | Zhang et al. |
| 2012/0143051 A1 | 6/2012 | Balakin |
| 2012/0165652 A1 | 6/2012 | Dempsey |
| 2012/0205551 A1 | 8/2012 | Balakin |
| 2012/0207276 A1 | 8/2012 | Pomper et al. |
| 2012/0209109 A1 | 8/2012 | Balakin |
| 2012/0223246 A1 | 9/2012 | Stephani et al. |
| 2012/0224667 A1 | 9/2012 | Cheng et al. |
| 2012/0242257 A1 | 9/2012 | Balakin |
| 2012/0248325 A1 | 10/2012 | Balakin |
| 2012/0256103 A1* | 10/2012 | Luzzara .............. G21K 1/046 250/492.1 |
| 2012/0264998 A1 | 10/2012 | Fujitaka et al. |
| 2012/0267543 A1 | 10/2012 | Noda et al. |
| 2012/0267544 A1 | 10/2012 | Ueda |
| 2012/0273665 A1 | 11/2012 | Schulte et al. |
| 2012/0273666 A1 | 11/2012 | Bert et al. |
| 2012/0280150 A1 | 11/2012 | Jongen |
| 2012/0303384 A1 | 11/2012 | Stepaniak et al. |
| 2012/0305796 A1 | 12/2012 | Iseki et al. |
| 2012/0313003 A1 | 12/2012 | Trbojevic |
| 2012/0326722 A1 | 12/2012 | Weinberg et al. |
| 2013/0001432 A1 | 1/2013 | Jongen |
| 2013/0043403 A1 | 2/2013 | Gordon et al. |
| 2013/0053616 A1 | 2/2013 | Gall et al. |
| 2013/0053617 A1 | 2/2013 | Pu et al. |
| 2013/0068938 A1 | 3/2013 | Heese |
| 2013/0072743 A1 | 3/2013 | Fieres et al. |
| 2013/0072744 A1 | 3/2013 | Moskvin et al. |
| 2013/0086500 A1 | 4/2013 | Kane et al. |
| 2013/0090549 A1 | 4/2013 | Meltsner et al. |
| 2013/0108014 A1 | 5/2013 | Tome et al. |
| 2013/0127375 A1 | 5/2013 | Sliski et al. |
| 2013/0131424 A1 | 5/2013 | Siski et al. |
| 2013/0131433 A1 | 5/2013 | Katscher et al. |
| 2013/0150647 A1 | 6/2013 | Chen et al. |
| 2013/0163723 A1 | 6/2013 | Tacke |
| 2013/0187060 A1 | 7/2013 | Jongen |
| 2013/0208867 A1 | 8/2013 | Beckman |
| 2013/0209450 A1 | 8/2013 | Cohen et al. |
| 2013/0211482 A1 | 8/2013 | Plipponen |
| 2013/0217946 A1 | 8/2013 | Balakin |
| 2013/0217948 A1 | 8/2013 | Mihaylov |
| 2013/0217950 A1 | 8/2013 | Partanen et al. |
| 2013/0218009 A1 | 8/2013 | Balakin |
| 2013/0221213 A1 | 8/2013 | Takayanagi et al. |
| 2013/0237425 A1 | 9/2013 | Leigh et al. |
| 2013/0237822 A1 | 9/2013 | Gross et al. |
| 2013/0243722 A1 | 9/2013 | Basile et al. |
| 2013/0245113 A1 | 9/2013 | Stockfleth |
| 2013/0259335 A1 | 10/2013 | Mallya et al. |
| 2013/0261430 A1 | 10/2013 | Uhlemann |
| 2013/0267756 A1 | 10/2013 | Totake et al. |
| 2013/0277569 A1 | 10/2013 | Behrens et al. |
| 2013/0299721 A1 | 11/2013 | Sasai |
| 2013/0303824 A1 | 11/2013 | Stephani et al. |
| 2013/0324479 A1 | 12/2013 | Zhang et al. |
| 2013/0345489 A1 | 12/2013 | Beloussov et al. |
| 2014/0005463 A1 | 1/2014 | Jongen |
| 2014/0005464 A1 | 1/2014 | Bharat et al. |

(56) References Cited

U.S. PATENT DOCUMENTS

| | | |
|---|---|---|
| 2014/0014851 A1 | 1/2014 | Asaba |
| 2014/0028220 A1 | 1/2014 | Bromberg et al. |
| 2014/0042934 A1 | 2/2014 | Tsutsui |
| 2014/0046113 A1 | 2/2014 | Fujimoto et al. |
| 2014/0061493 A1 | 3/2014 | Prieels et al. |
| 2014/0066755 A1 | 3/2014 | Matteo et al. |
| 2014/0077699 A1 | 3/2014 | Boswell et al. |
| 2014/0091238 A1 | 4/2014 | Miyashita et al. |
| 2014/0091734 A1 | 4/2014 | Gall et al. |
| 2014/0094371 A1 | 4/2014 | Zwart et al. |
| 2014/0094637 A1 | 4/2014 | Zwart et al. |
| 2014/0094639 A1 | 4/2014 | Zwart et al. |
| 2014/0094640 A1 | 4/2014 | Gall et al. |
| 2014/0094641 A1 | 4/2014 | Gall et al. |
| 2014/0094643 A1 | 4/2014 | Gall et al. |
| 2014/0094838 A1 | 4/2014 | Gall et al. |
| 2014/0097920 A1 | 4/2014 | Goldie et al. |
| 2014/0107390 A1 | 4/2014 | Brown et al. |
| 2014/0112453 A1 | 4/2014 | Prince et al. |
| 2014/0113388 A1 | 4/2014 | Bitter et al. |
| 2014/0121441 A1 | 5/2014 | Huber et al. |
| 2014/0128719 A1 | 5/2014 | Longfield |
| 2014/0145090 A9 | 5/2014 | Jongen |
| 2014/0193058 A1 | 7/2014 | Bharat et al. |
| 2014/0200448 A1 | 7/2014 | Schulte et al. |
| 2014/0203186 A1 | 7/2014 | Iwamoto et al. |
| 2014/0221816 A1 | 8/2014 | Franke et al. |
| 2014/0257011 A1 | 9/2014 | Spotts |
| 2014/0257099 A1 | 9/2014 | Balakin |
| 2014/0275699 A1 | 9/2014 | Benna et al. |
| 2014/0275704 A1 | 9/2014 | Zhang et al. |
| 2014/0308202 A1 | 10/2014 | Matusik et al. |
| 2014/0316184 A1 | 10/2014 | Fujimoto et al. |
| 2014/0330063 A1 | 11/2014 | Balakin |
| 2014/0332691 A1 | 11/2014 | Campbell et al. |
| 2014/0336438 A1 | 11/2014 | Bharat et al. |
| 2014/0350322 A1 | 11/2014 | Schulte et al. |
| 2014/0369958 A1 | 12/2014 | Basile |
| 2014/0371076 A1 | 12/2014 | Jongen |
| 2014/0371511 A1 | 12/2014 | Zwart et al. |
| 2015/0015167 A1 | 1/2015 | Ungaro et al. |
| 2015/0030223 A1 | 1/2015 | Pearlstein et al. |
| 2015/0031933 A1 | 1/2015 | Yamamoto et al. |
| 2015/0041665 A1 | 2/2015 | Hollebeek et al. |
| 2015/0076370 A1 | 3/2015 | Totake et al. |
| 2015/0080633 A1 | 3/2015 | Anferov |
| 2015/0080634 A1 | 3/2015 | Huber et al. |
| 2015/0087883 A1 | 3/2015 | Boudreau et al. |
| 2015/0087885 A1 | 3/2015 | Boisseau et al. |
| 2015/0087887 A1 | 3/2015 | Iwata |
| 2015/0087960 A1 | 3/2015 | Treffert |
| 2015/0090894 A1 | 4/2015 | Zwart et al. |
| 2015/0099917 A1 | 4/2015 | Bula et al. |
| 2015/0099918 A1 | 4/2015 | Takayanagi et al. |
| 2015/0126797 A1 | 5/2015 | Aptaker et al. |
| 2015/0146856 A1 | 5/2015 | Beckman |
| 2015/0148584 A1 | 5/2015 | Gall et al. |
| 2015/0174429 A1* | 6/2015 | Zwart ................ A61N 5/1083 |
| | | 250/396 R |
| 2015/0196534 A1 | 7/2015 | Vidyasagar et al. |
| 2015/0196779 A1 | 7/2015 | Tonner |
| 2015/0209601 A1 | 7/2015 | Benna et al. |
| 2015/0217138 A1 | 8/2015 | Fujimoto et al. |
| 2015/0217140 A1 | 8/2015 | Balakin |
| 2015/0231411 A1* | 8/2015 | O'Neal, III ............. H05H 7/04 |
| | | 600/1 |
| 2015/0273239 A1 | 10/2015 | Hsu et al. |
| 2015/0321025 A1 | 11/2015 | Freud et al. |
| 2015/0328483 A1 | 11/2015 | Odawara et al. |
| 2015/0335463 A1 | 11/2015 | De Gruytere |
| 2015/0335919 A1 | 11/2015 | Behar et al. |
| 2015/0337393 A1 | 11/2015 | Keller et al. |
| 2015/0343238 A1 | 12/2015 | Balakin |
| 2015/0352372 A1 | 12/2015 | Takayanagi et al. |
| 2015/0352374 A1 | 12/2015 | Gattikar et al. |
| 2015/0352376 A1* | 12/2015 | Wiggers ................ A61B 6/06 |
| | | 378/207 |
| 2015/0374324 A1 | 12/2015 | Nishimura et al. |
| 2016/0000387 A1 | 1/2016 | Buchsbaum et al. |
| 2016/0008631 A1 | 1/2016 | Harada et al. |
| 2016/0016010 A1 | 1/2016 | Schulte et al. |
| 2016/0048981 A1 | 2/2016 | Pearlstein et al. |
| 2016/0059039 A1 | 3/2016 | Liu |
| 2016/0067316 A1 | 3/2016 | Sunavala-Dossabhoy |
| 2016/0071623 A1 | 3/2016 | Schewiola et al. |
| 2016/0074675 A1 | 3/2016 | Moskvin et al. |
| 2016/0113884 A1 | 4/2016 | Lin et al. |
| 2016/0136457 A1 | 5/2016 | Jung et al. |
| 2016/0144201 A1 | 5/2016 | Schulte |
| 2016/0172066 A1 | 6/2016 | Claereboudt |
| 2016/0172067 A1 | 6/2016 | Claereboudt et al. |
| 2016/0175052 A1 | 6/2016 | Kumar et al. |
| 2016/0175617 A1 | 6/2016 | Spatola et al. |
| 2016/0199667 A1* | 7/2016 | Flynn ..................... G21K 1/04 |
| | | 600/1 |
| 2016/0199670 A1 | 7/2016 | Michaud et al. |
| 2016/0199671 A1 | 7/2016 | Jongen |
| 2016/0220847 A1 | 8/2016 | Benna et al. |
| 2016/0243232 A1 | 8/2016 | Pickett |
| 2016/0250501 A1 | 9/2016 | Balakin |
| 2016/0250503 A1 | 9/2016 | Balakin et al. |
| 2016/0256712 A1 | 9/2016 | Vahala et al. |
| 2016/0263404 A1 | 9/2016 | Mougenot |
| 2016/0270203 A1 | 9/2016 | Ungaro et al. |
| 2016/0271424 A1 | 9/2016 | Lee et al. |
| 2016/0287899 A1 | 10/2016 | Park et al. |
| 2016/0296766 A1 | 10/2016 | El Fakhri et al. |
| 2016/0303399 A1 | 10/2016 | Balakin |
| 2016/0331999 A1 | 11/2016 | Hartman et al. |
| 2017/0128746 A1 | 5/2017 | Zwart et al. |
| 2017/0157422 A1 | 6/2017 | Zwart et al. |
| 2017/0157424 A1 | 6/2017 | Zwart et al. |
| 2017/0157425 A1 | 6/2017 | Zwart et al. |
| 2017/0182338 A1 | 6/2017 | Zwart et al. |
| 2018/0220846 A1 | 8/2018 | Wangler et al. |

FOREIGN PATENT DOCUMENTS

| | | |
|---|---|---|
| CN | 1537657 | 10/2004 |
| CN | 1816243 A | 8/2006 |
| CN | 101061759 A | 10/2007 |
| CN | 101145409 A | 3/2008 |
| CN | 101361156 A | 2/2009 |
| CN | 101932361 A | 12/2010 |
| CN | 101933405 A | 12/2010 |
| CN | 101933406 A | 12/2010 |
| CN | 102905761 A | 1/2013 |
| DE | 2753397 A1 | 6/1978 |
| DE | 3148100 A1 | 6/1983 |
| DE | 3530446 A1 | 3/1986 |
| DE | 3711245 A1 | 10/1988 |
| DE | 4101094 C1 | 5/1992 |
| DE | 4411171 A1 | 10/1995 |
| DE | 19907098 A1 | 8/2000 |
| DE | 102011089235 A1 | 8/2012 |
| EP | 0194728 A1 | 9/1986 |
| EP | 0208163 A1 | 1/1987 |
| EP | 0221987 A1 | 5/1987 |
| EP | 0222786 A1 | 5/1987 |
| EP | 0277521 A2 | 8/1988 |
| EP | 0306966 A2 | 3/1989 |
| EP | 0388123 A2 | 9/1990 |
| EP | 0465597 A1 | 1/1992 |
| EP | 0499253 A1 | 8/1992 |
| EP | 0751532 A1 | 1/1997 |
| EP | 0776595 A1 | 6/1997 |
| EP | 0864337 A2 | 9/1998 |
| EP | 0911064 A2 | 4/1999 |
| EP | 1069809 A1 | 1/2001 |
| EP | 1153398 A1 | 11/2001 |
| EP | 1294445 A2 | 3/2003 |
| EP | 1348465 A1 | 10/2003 |
| EP | 1358908 A1 | 11/2003 |
| EP | 1371390 A1 | 12/2003 |

(56) References Cited

FOREIGN PATENT DOCUMENTS

| | | |
|---|---|---|
| EP | 1402923 A1 | 3/2004 |
| EP | 1430932 A1 | 8/2004 |
| EP | 1454653 A1 | 9/2004 |
| EP | 1454654 A2 | 9/2004 |
| EP | 1454655 A2 | 9/2004 |
| EP | 1454656 A2 | 9/2004 |
| EP | 1454657 A2 | 9/2004 |
| EP | 1477206 A1 | 11/2004 |
| EP | 1605742 A1 | 12/2005 |
| EP | 1738798 A2 | 1/2007 |
| EP | 1826778 A2 | 8/2007 |
| EP | 1949404 A2 | 7/2008 |
| EP | 2114529 B1 | 11/2009 |
| EP | 2183753 A1 | 5/2010 |
| EP | 2227295 A1 | 9/2010 |
| EP | 2232961 A1 | 9/2010 |
| EP | 2232962 A2 | 9/2010 |
| EP | 2363170 A1 | 9/2011 |
| EP | 2363171 A1 | 9/2011 |
| EP | 2394498 A2 | 12/2011 |
| EP | 2514482 A1 | 10/2012 |
| EP | 2524718 A1 | 11/2012 |
| EP | 3035776 A1 | 6/2016 |
| EP | 3088048 A1 | 11/2016 |
| FR | 2560421 A1 | 8/1985 |
| FR | 2911843 A1 | 8/2008 |
| GB | 0957342 A | 5/1964 |
| GB | 2015821 A | 9/1979 |
| GB | 2361523 A | 10/2001 |
| JP | S47-028762 U | 12/1972 |
| JP | S48-108098 U | 12/1973 |
| JP | S57-162527 A | 10/1982 |
| JP | 58-141000 | 8/1983 |
| JP | 61-225798 | 10/1986 |
| JP | 62-150804 | 7/1987 |
| JP | 62-186500 | 8/1987 |
| JP | 63-149344 | 6/1988 |
| JP | 63-218200 | 9/1988 |
| JP | 63-226899 | 9/1988 |
| JP | 64-89621 | 4/1989 |
| JP | 01-276797 | 11/1989 |
| JP | 01-302700 | 12/1989 |
| JP | 4-94198 | 3/1992 |
| JP | 06-105922 A | 4/1994 |
| JP | 06-036893 | 8/1994 |
| JP | 08-233831 | 8/1994 |
| JP | 07-260939 | 10/1995 |
| JP | 07-263196 | 10/1995 |
| JP | 08-173890 | 7/1996 |
| JP | 08-264298 | 10/1996 |
| JP | 09-162585 | 6/1997 |
| JP | 10-071213 | 3/1998 |
| JP | 11-028252 A | 2/1999 |
| JP | 11-47287 | 2/1999 |
| JP | 2011-28252 A | 2/1999 |
| JP | H1128252 A | 2/1999 |
| JP | 11-102800 | 4/1999 |
| JP | 11-243295 | 9/1999 |
| JP | 2000-243309 A | 9/2000 |
| JP | 2000-294399 A | 10/2000 |
| JP | 2001-6900 | 1/2001 |
| JP | 2001-009050 A | 1/2001 |
| JP | 2001-129103 A | 5/2001 |
| JP | 2001-212253 A | 8/2001 |
| JP | 2001-276238 A | 10/2001 |
| JP | 2001-346893 A | 12/2001 |
| JP | 2002-164686 A | 6/2002 |
| JP | 2003-504628 A | 2/2003 |
| JP | 2004-067875 A | 3/2003 |
| JP | 2003-517755 A | 5/2003 |
| JP | 2004-031115 A | 1/2004 |
| JP | 2005-526578 A | 9/2005 |
| JP | 2006-032282 A | 2/2006 |
| JP | 2006341010 A | 12/2006 |
| JP | 2007-307223 A | 11/2007 |
| JP | 2008-068092 A | 3/2008 |
| JP | 2008-507826 A | 3/2008 |
| JP | 04-128717 B2 | 7/2008 |
| JP | 04-129768 B2 | 8/2008 |
| JP | 2008-229324 A | 10/2008 |
| JP | 61-80800 | 1/2009 |
| JP | 2009-015397 A | 1/2009 |
| JP | 2009-515671 A | 4/2009 |
| JP | 2009-516905 A | 4/2009 |
| JP | 04-273409 B2 | 6/2009 |
| JP | 04-337300 B2 | 9/2009 |
| JP | 43-23267 B2 | 9/2009 |
| JP | 2010-29594 A | 2/2010 |
| JP | 2010-536130 A | 11/2010 |
| JP | 2011-505191 A | 2/2011 |
| JP | 2011-505670 A | 2/2011 |
| JP | 2011-507151 A | 3/2011 |
| JP | 05-046928 B2 | 10/2012 |
| JP | 2012-223259 A | 11/2012 |
| JP | 2013-106981 A | 6/2013 |
| JP | 05-341352 B2 | 11/2013 |
| JP | 2014-020800 A | 2/2014 |
| JP | 2015-150184 A | 8/2015 |
| JP | 2015-154933 A | 8/2015 |
| JP | 2010029594 A | 2/2020 |
| SU | 300137 | 6/1969 |
| SU | 569635 A1 | 8/1977 |
| TW | 200930160 A | 7/2009 |
| TW | 200934682 A | 8/2009 |
| TW | 200939908 A | 9/2009 |
| TW | 200940120 A | 10/2009 |
| WO | WO-86/07229 A1 | 12/1886 |
| WO | WO-90/12413 A1 | 10/1990 |
| WO | WO-92/03028 A1 | 2/1992 |
| WO | WO-93/02536 A1 | 2/1993 |
| WO | WO-98/17342 A2 | 4/1998 |
| WO | WO-1999/39385 A1 | 8/1999 |
| WO | WO-2000/40084 A2 | 7/2000 |
| WO | WO-2000/49624 A1 | 8/2000 |
| WO | WO-01/126569 | 4/2001 |
| WO | WO-2001/026230 A1 | 4/2001 |
| WO | WO-02/07817 | 1/2002 |
| WO | WO-2003/039212 A1 | 5/2003 |
| WO | WO-2003/092812 A1 | 11/2003 |
| WO | WO-2004/026401 A1 | 4/2004 |
| WO | WO-2004/101070 A1 | 11/2004 |
| WO | WO-2006-012467 A2 | 2/2006 |
| WO | WO-2007/081937 A2 | 5/2007 |
| WO | WO-2007/084701 A1 | 7/2007 |
| WO | WO-2007/130164 A2 | 11/2007 |
| WO | WO-2007/145906 A2 | 12/2007 |
| WO | WO-2008/030911 A2 | 3/2008 |
| WO | WO-2008/081480 A1 | 7/2008 |
| WO | WO-2009/048745 A2 | 4/2009 |
| WO | WO-2009/070173 A1 | 6/2009 |
| WO | WO-2009/070588 A1 | 6/2009 |
| WO | WO-2009/073480 A2 | 6/2009 |
| WO | 2012008274 A1 | 1/2012 |
| WO | 2012023176 A1 | 2/2012 |
| WO | WO-2014/018706 A1 | 1/2014 |
| WO | WO-2014/018876 A1 | 1/2014 |
| WO | 2015003111 A1 | 1/2015 |
| WO | WO-2015/095678 A2 | 6/2015 |
| WO | 2015107660 A1 | 7/2015 |
| WO | WO-2017/082984 A1 | 5/2017 |
| WO | WO2018/009779 | 1/2018 |
| WO | WO-2018/128822 A1 | 7/2018 |

OTHER PUBLICATIONS

M. R. Witten and O. C. Clancey, "A mimetic algorithm for simultaneous multileaf collimator aperture shape and dosimetric optimization in CyberKnife robotic radiosurgery," 2015 IEEE Congress on Evolutionary Computation (CEC), 2015, pp. 1589-1595, doi: 10.1109/CEC.2015.7257077. (Year: 2015).*

Galvin, James M. "The multileaf collimator: a complete guide." Proc. AAPM annual meeting. 1999. (Year: 1999).*

(56) References Cited

OTHER PUBLICATIONS

Boyer, Arthur, and Biggs, Peter, et al. "Basic Application of Multileaf Collimators" American Association of Physicists in Medicine, Report No. 072 (2001). ISBN: 978-1-888340-30-3 https://doi.org/10.37206/71 (Year: 2001).*
J. M. Schippers, "Developments in Accelerators Used for Particle Therapy," in IEEE Transactions on Nuclear Science, vol. 63, No. 2, pp. 939-948, Apr. 2016, doi: 10.1109/TNS.2015.2470104. (Year: 2016).*
T. Aso et al., "Verification of the dose distributions with GEANT4 simulation for proton therapy," IEEE Symposium Conference Record Nuclear Science 2004., Rome, Italy, 2004, pp. 2138-2142 vol. 4, doi: 10.1109/NSSMIC.2004. 1462685. (Year: 2004).*
European Search Report dated Sep. 29, 2021, European Application No. 21169478 filed Apr. 20, 2021 (7 pages).
Third Office Action for Japanese Patent Application No. 2019-500488, 9 pages, issued Feb. 17, 2021, (with English Translation).
Communication pursuant to Article 94(3) EPC in European Application No. 21169478.1 dated Dec. 6, 2023, 4 pages.
Machine Translation of Japanese Patent Publication No. JP2010029594 (Feb. 12, 2010), Saotome et al., 5 pages.
Final Office Action for Japanese Patent Application No. 2019-500488, issued Sep. 27, 2021, with English Translation, (5 pages).
First Office Action for Chinese Patent Application No. 201780055007.5, 24 pages, issued Jun. 29, 2020, (with English Translation).
Second Offica Action for Japanese Patent Application No. 2019-500488, 7 pages, issued Aug. 3, 2020, (with English Translation).
First Office Action for Japanese Patent Application No. 2018-544022, 13 pages, issued Aug. 17, 2020, (with English Translation).
EPO Communication Pursuant to Article 94(3) EPC for EP 17740595.8, 4 pages (Feb. 20, 2020).
Notice of Reasons for Rejection for JP 2019-500488, 9 pages, mailed Jan. 27, 2020, (with English translation).
File History of U.S. Appl. No. 61/883,631, filed Sep. 27, 2013.
Final Office Action for U.S. Appl. No. 15/438,544, 47 pages (Apr. 29, 2019).
Final Office Action for U.S. Appl. No. 15/438,854, 32 pages (Sep. 17, 2019).
Non-Final Office Action for U.S. Appl. No. 15/438,854, 31 pages (May 8. 2019).
File History of U.S. Appl. No. 14/937,048, filed Nov. 10, 2015.
File History of U.S. Appl. No. 15/438,544, filed Feb. 21, 2017.
File History of U.S. Appl. No. 15/438,863, filed Feb. 22. 2017.
Final Office Action for U.S. Appl. No. 15/438,863, 25 pages (Sep. 17, 2019).
Final Office Action for U.S. Appl. No. 14/937,048, 86 pages (May 9, 2019).
Gustafsson et al., "Simultaneous optimization of dynamic multileaf collimation and scanning patterns or compensation filters using a generalized pencil beam algorithm", Medical physics (Year: 1995).
Hyer, "A dynamic collimation system for penumbra reduction in spot scanning proton therapy: proof of concept" (Year: 2014).
Non-Final Office Action for U.S. Appl. No. 15/438,863, 28 pages (May 8, 2019).
Non-Final Office Action for U.S. Appl. No. 14/937,048, 81 pages (Aug. 15, 2018).
Non-Final Office Action for U.S. 14/937,048 86 pages Oct. 2, 2019.
Second Office Action (Chinese translation) for CN201480070002.6, 3 pages (Jan. 11, 2019).
Second Office Action (English translation) for CN201480070002.6, 4 pages (Jan. 11, 2019).
Communication under Rule 71(3) EPC for EP14830919.8, 113 pages (May 2, 2018).
Final Office Action for U.S. Appl. No. 15/438,854, 30 pages (Nov. 28, 2018).
Final Office Action for U.S. Appl. No. 15/438,863, 30 pages (Nov. 28, 2018).
Office Action for U.S. Appl. No. 15/399,250, 8 pages (Jan. 24, 2019).
Final Office Action for U.S. Appl. No. 14/937,048, 52 pages (Mar. 1, 2018).
Final Office Action for U.S. Appl. No. 15/438,544, 31 pages (Mar. 1, 2018).
First Office Action for CN201480070002.6 (Chinese translation), 9 pages (Apr. 11, 2018).
First Office Action for CN201480070002.6 (English translation), 12 pages (Apr. 11, 2018).
International Search Report for PCT/US2017/067677 (High-Speed Energy Switching, filed Dec. 20, 2017), issued by ISA/US, 4 pages (Apr. 30, 2018).
Office Action for U.S. Appl. No. 14/137,854, 24 pages (Oct. 23, 2017).
Office Action for U.S. Appl. No. 14/937,048, 94 pages (Oct. 13, 2017).
Office Action for U.S. Appl. No. 15/399,250, 78 pages (Jan. 19, 2018).
Office Action for U.S. Appl. No. 15/438,544, 27 pages (Oct. 12, 2017).
Written Opinion for PCT/US2017/067677 (High-Speed Energy Switching, filed Dec. 20, 2017), issued by ISA/US, 7 pages (Apr. 30, 2018).
International Search Report for PCT/US2017/041076 (Treatment Planning, filed Jul. 7, 2017), issued by ISA/EPO, 5 pages (Sep. 27, 2017).
Written Opinion for PCT/US2017/041076 (Treatment Planning, filed Jul. 7, 2017), issued by ISA/EPO, 8 pages (Sep. 27, 2017).
18th Japan Conference on Radiation and Radioisotopes [Japanese], Nov. 25-27, 1987, 9 pages.
510(k) Summary: Ion Beam Applications S.A., FDA, Jul. 12, 2001, 5 pages.
510(k) Summary: Optivus Proton Beam Therapy System, Jul. 21, 2000, 5 pages.
Abrosimov et al., 1000MeV Proton Beam Therapy facility at Petersburg Nuclear Physics Institute Synchrocyclotron, Medical Radiology (Moscow) 32, 10 (1987) revised in Journal of Physics, Conference Series 41, 2006, pp. 424-432, Institute of Physics Publishing Limited.
Abrosimov et al., Neutron Time-of-flight Spectrometer Gneis at the Gatchina 1 GeV Protron Syncrhocyclotron, Mar. 9, 1985 and revised form Jul. 31, 1985, Lemingrad Nuclear Physics Institute, Gatchina, 188350, USSR (15 pages).
Adachi et al., A 150MeV FFAG Synchrotron with Return-Yoke Free Magent, Proceedings of the 2001 Particle Accelerator Conference, Chicago, 2001, 3 pages.
Ageyev et al., The IHEP Accelerating and Storage Complex (UNK) Status Report, 11th International Conference on High-Energy Accelerators, 1980, pp. 60-70.
Agosteo et al., Maze Design of a gantry room for proton therapy, Nuclear Instruments & Methods in Physics Research, 1996, Section A, 382, pp. 573-582.
Alexeev et al., R4 Design of Superconducting Magents for Proton Synchrotrons, Proceedings of the Fifth International Crvogenic Engineering Conference, 197 4, pp. 531-533.
Allardyce et al., Performance and Prospects of the Reconstructed CERN 600 MeV Synchrocyclotron, IEEE Transactions on Nuclear Science USA, Jun. 1977, ns-24:(3) 1631-1633.
Alonso, Magnetically Scanned Ion Beams for Radiation Therapy, Accelerator & Fusion Research Division, Lawrence Berkeley Laboratory, Berkeley, CA, Oct. 1988, 13 pages.
Amaldi et al., The Italian project for a hadrontherapy centre Nuclear Instruments and Methods in Physics Research A, 1995, 360, pp. 297-301.
Amaldi, Overview of the world landscape of Hadrontherapy and the projects of the TERA foundation, Physica Medica, An International journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977. Baveno, pp. 76-85.
An Accelerated Collaboration Meets with Beaming Success, Lawrence Livermore National Laboratory, Apr. 12, 2006, S&TR, Livermore, California, pp. 1-3, http://www.llnl.gov/str/April06/Caporaso.html.

(56) References Cited

OTHER PUBLICATIONS

Anferov et al., Status of the Midwest Proton Radiotherapy Institute, Proceedings of the 2003 Particle Accelerator Conference, 2003, pp. 699-701.
Anferov et al., The Indiana University Midwest Proton Radiation Institute, Proceedings of the 2001 Particle Accelerator Conference, 2001, Chicago, pp. 645-647.
Appun, Various problems of magnet fabrication for high-energy accelerators, Journal for All Engineers Interested in the Nuclear Field, 1967, 11 pp. 10-16 (1967) [Lang.: German], English bibliographic information (httn://www.osti.1mv/enernvcitations/product.biblio.isn?ostiid=4442292).
Arduini et al. Physical specifications of clinical proton beams from a synchrotron, Med. Phys, Jun. 1996, 23 ( 6): 939-951.
Badano et al., Proton-Ion Medical Machine Study (PIMMS) Part I, PIMMS, Jan. 1999, 238 pages.
Beam Delivery and Properties, Journal of the ICRU, 2007, 7(2):20 pages.
Beeckman et al., Preliminary design of a reduced cost proton therapy facility using a compact, high field isochronous cyclotron, Nuclear Instruments and Methods in Physics Research B56/57, 1991, pp. 1201-1204.
Bellomo et al., The Superconducting Cyclotron Program at Michigan State University, Bulletin of the American Physical Society, Sep. 1980, 25(7):767.
Benedikt and Carli, Matching to Gantries for Medical Synchrotrons IEEE Proceedings of the 1997 Particle Accelerator Conference, 1997, pp. 13 79-13 81.
Bieth et al., A Very Compact Protontherapy Facility Based on an Extensive Use of High Temperature Superconductors (HTS) Cyclotrons and their Applications 1998, Proceedings of the Fifteenth International Conference on Cyclotrons and their Applications, Caen, Jun. 14-19, 1998, pp. 669-672.
Bigham, Magnetic Trim Rods for Superconducting Cyclotrons, Nuclear Instruments and Methods (North-Holland Publishing Co.), 1975, 141:223-228.
Bimbot, First Studies of the External Beam from the Orsay S.C. 200 MeV, Institut de Physique Nucleaire, BP 1, Orsay, France, IEEE, 1979, pp. 1923-1926.
Blackmore et al., Operation of the Triumf Proton Therapy Facility, IEEE Proceedings of the 1997 Particle Accelerator Conference, May 12-16, 1997, 3:3831-3833.
Bloch, The Midwest Proton Therapy Center, Application of Accelerators in Research and Industry, Proceedings of the Fourteenth Int'l. Conf, Part Two, Nov. 1996, pp. 1253-1255.
Blosser et al., A Compact Superconducting Cyclotron for the Production of High Intensity Protons, Proceedings of the 1997 Particle Accelerator Conference, May 12-16, 1997, 1:1054-1056.
Blosser et al., Advances in Superconducting Cyclotrons at Michigan State University, Proceedings of the 11th International Conference on Cyclotrons and their Applications, Oct. 1986, pp. 157-167, Tokyo.
Blosser et al., Characteristics of a 400 (Q2/A) MeV Super-Conducting Heavy-Ion Cyclotron, Bulletin of the American Physical Society, Oct. 1974, p. 1026.
Blosser et al., Medical Accelerator Projects at Michigan State Univ. IEEE Proceedings of the 1989 Particle Accelerator Conference, Mar. 20-23, 1989, 2:742-746.
Blosser et al., Problems and Accomplishments of Superconducting Cyclotrons, Proceedings of the 14th International Conference, Cyclotrons and Their Applications, Oct. 1995, pp. 674-684.
Blosser et al., Superconducting Cyclotron for Medical Application, IEEE Transactions on Magnetics, Mar. 1989, 25(2): 1746-1754.
Blosser et al., Superconducting Cyclotrons, Seventh International Conference on Cyclotrons and their Applications, Aug. 19-22, 1975, pp. 584-594.
Blosser, Application of Superconductivity in Cyclotron Construction, Ninth International Conference on Cyclotrons and their Applications, Sep. 1981, pp. 147-157.
Blosser, Applications of Superconducting Cyclotrons, Twelfth International Conference on Cyclotrons and Their Applications, May 8-12, 1989, pp. 137-144.
Blosser, Future Cyclotrons, AIP, The Sixth International Cyclotron Conference, 1972, pp. 16-32.
Blosser, H., Present and Future Superconducting Cyclotrons, Bulletin of the American Physical Society, Feb. 1987, 32(2):171 Particle Accelerator Conference, Washington, D.C.
Blosser, H.G., Superconducting Cyclotrons at Michigan State University, Nuclear Instruments & Methods in Physics Research, 1987,vol. B 24/25, part II, pp. 752-756.
Blosser, Medical Cyclotrons, Physics Today, Special Issue Physical Review Centenary, Oct. 1993, pp. 70-73.
Blosser, Preliminary Design Study Exploring Building Features Required for a Proton Therapy Facility for the Ontario Cancer Institute, Mar. 1991, MSUCL-760a, 53 pages.
Blosser, Progress on the Coupled Superconducting Cyclotron Project, Bulletin of the American Physical Society, 1993 (p. 3).
Blosser, Synchrocyclotron Improvement Programs, IEEE Transactions on Nuclear Science USA, Jun. 1969, 16(3):Part I, pp. 405-414.
Blosser, The Michigan State University Superconducting Cyclotron Program, Nuclear Science, Apr. 1979, NS-26(2):2040-2047.
Botha et al., A New Multidisciplinary Separated-Sector Cyclotron Facility, IEEE Transactions on Nuclear Science, 1977, NS-24(3): 1118-1120.
Bues, M. et al., Therapeutic Step and Shoot Proton Beam Spot-Scanning With a Multi-Leaf Collimator: A Monte Carlo Study, Radiation Protection Dosimetry, 115(1-4):164-169 (2005).
Chichili et al., Fabrication ofNb3Sn Shell-Type Coils with Pre-Preg Ceramic Insulation, American Institute of Physics Conference Proceedings, AIP USA, No. 711, (XP-002436709, ISSN: 0094-243X), 2004, pp. 450-457.
Chong et al., Radiology Clinic North American 7, 3319, 1968, 27 pages.
Chu et al., Instrumentation for Treatment of Cancer Using Proton and Light-ion Beams, Review of Scientific Instruments, Aug. 1993, 64 (8):2055-2122.
Chu et al., Performance Specifications for Proton Medical Facility, Lawrence Berkeley Laboratory, University of California, Mar. 1993, 128 pages.
Chu, Instrumentation in Medical Systems, Accelerator and Fusion Research Division, Lawrence Berkeley Laboratory, University of Califomia, Berkeley, CA, May 1995, 9 pages.
Cole et al., Design and Application of a Proton Therapy Accelerator, Fermi National Accelerator Laboratory, IEEE, 1985, 5 pages.
Collins, et al., The Indiana University Proton Therapy System, Proceedings of EPAC 2006, Edinburgh, Scotland, 2006, 3 pages.
Communication pursuant to Article 94(3) EPC for EP14830919.8, 6 pages (May 12, 2017).
Communication pursuant to Rules 161(1) and 162 EPC in EP14830819.8, 2 pages (Sep. 2, 2016).
Conradi et al., Proposed New Facilities for Proton Therapy at iThemba Labs, Proceedings of EPAC, 2002, pp. 560-562.
C/E Source of Ions for Use in Sychro-Cyclotrons Search, Jan. 31, 2005, 9 pages.
Cosgrove et al., Microdosimetric Studies on the Orsay Proton Synchrocyclotron at 73 and 200 MeV, Radiation Protection Dosimetry, 1997, 70(1-4):493-496.
Coupland, High-field (5 T) pulsed superconducting dipole magnet, Proceedings of the Institution of Electrical Engineers, Jul. 1974, 121(7):771-778.
Coutrakon et al. Proton Synchrotrons for Cancer Therapy, Application of Accelerators in Research and Industry—Sixteenth International Conf., American Institute of Physics, Nov. 1-5, 2000, vol. 576, pp. 861-864.
Coutrakon et al., A prototype beam delivery system for the proton medical accelerator at Loma Linda, Medical Physics, Nov./Dec. 1991, 18(6):1093-1099.
CPAC Highlights Its Proton Therapy Program at ESTRO Annual Meeting, TomoTherapy Incorporated, Sep. 18, 2008, Madison, Wisconsin, pp. 1-2.

(56) References Cited

OTHER PUBLICATIONS

Cuttone, Applications of a Particle Accelerators in Medical Physics, Istituto Nazionale di Fisica Nucleare-Laboratori Nazionali del Sud, V.S. Sofia, 44 Cantania, Italy, Jan. 2010, 17 pages.

Dahl P, Superconducting Magnet System, American Institute of Physics, AIP Conference Proceedings, 1987-1988, 2: 1329-1376.

Dialog Search, Jan. 31, 2005, 17 pages.

Dugan et al., Tevatron Status IEEE, Particle Accelerator Conference, Accelerator Science & Technology, 1989, pp. 426-430.

Eickhoff et al., The Proposed Accelerator Facility for Light Ion Cancer Therapy in Heidelberg, Proceedings of the 1999 Particle Accelerator Conference, New York, 1999, pp. 2513-2515.

Enchevich et al., Minimizing Phase Losses in the 680 MeV Synchrocyclotron by Correcting the Accelerating Voltage Amplitude, Atomnaya Energiya, 1969, 26:(3):315-316.

Endo et al., Compact Proton and Carbon Ion Synchrotrons for Radiation Therapy, Proceedings of EPAC 2002, Paris France, 2002, pp. 2733-2735.

FIle History of U.S. Appl. No. 13/303,110.

File History of U.S. Appl. No. 61/843,092, 84 pages (downloaded Oct. 14, 2016).

File History of U.S. Appl. No. 61/900,455, 43 pages (downloaded Oct. 14, 2016).

File History of U.S. Appl. No. 61/946,074, 137 pages (downloaded Oct. 14, 2016).

Final Office Action for U.S. Appl. No. 14/137,854, 29 pages (Sep. 19, 2016).

First Office Action (English translation) for JP2016-541203, 10 pages (Jul. 31, 2017).

First Office Action (Japanese translation) for JP2016-541203, 7 pages (Jul. 31, 2017).

Flanz et al., Large Medical Gantries, Particle Accelerator Conference, Massachusetts General Hospital, 1995, pp. 1-5.

Flanz et al., Operation of a Cyclotron Based Proton Therapy Facility, Massachusetts General Hospital, Boston, MA 02114, pp. 1-4, retrieved from Internet in 2009.

Flanz et al., The Northeast Proton Therapy Center at Massachusetts General Hospital, Fifth Workshop on Heavy Charge Particles in Biology and Medicine, GSI, Darmstadt, Aug. 1995, 11 pages.

Flanz et al., Treating Patients with the NPTC Accelerator Based Proton Treatment Facility, Proceedings of the 2003 Particle Accelerator Conference, 2003, pp. 690-693.

Flood and Frazier, The Wide-Band Driven RF System for the Berkeley 88-Inch Cyclotron, American Institute of Physics, Conference Proceedings., No. 9, 1972, 459-466.

Foster and Kashikhin, Superconducting Superferric Dipole Magent with Cold Iron Core for the VLHC, IEEE Transactions on Applied Superconductivity, Mar. 2002, 12(1):111-115.

Friesel et al., Design and Construction Progress on the IUCF Midwest Proton Radiation Institute, Proceedings of EPAC 2002, 2002, pp. 2736-2738.

Fukumoto et al., A Proton Therapy Facility Plan Cyclotrons and their Applications, Proceedings of the 13th International Conference, Vancouver, Canada, Jul. 6-10, 1992, pp. 258-261.

Fukumoto, Cyclotron Versus Synchrotron for Proton Beam Therapy, KEK Prepr., No. 95-122, Oct. 1995, pp. 533-536.

Goto et al., Progress on the Sector Magnets for the Riken SRC, American Institute of Physics, 714 CP600, Cyclotrons and Their Applications 2001, Sixteenth International Conference, 2001, pp. 319-323.

Graffman et al., Design Studies for a 200 MeV Proton Clinic for Radiotherapy, AIP Conference Proceedings: Cyclotrons—1972, 1972, No. 9, pp. 603-615.

Graffman, et. al. Proton radiotherapy with the Uppsala cyclotron. Experience and plans Strahlentherapie, 1985, 161(12):764-770.

Graffman, S., et al., Clinical Trials in Radiotherapy and the Merits of High Energy Protons, Acta Radiol. Therapy Phys. Blol. 9:1-23 (1970).

Hardemark, B. et al., Pinnacle3® White Paper—P3IMRT. Direct machine parameter optimization, Royal Philips Electronics N.V., 8 page (2004).

Hede, Research Groups Promoting Proton Therapy Lite, Journal of the National Cancer Institute, Dec. 6, 2006, 98(23):1682-1684.

Heinz, Superconducting Pulsed Magnetic Systems for High-Energy Synchrotrons, Proceedings of the Fourth International Cryogenic Engineering Conference, May 24-26, 1972, pp. 55-63.

Hentschel et al., Plans for the German National Neutron Therapy Centre with a Hospital-Based 70 MeV Proton Cyclotron at University Hospital Essen/Germany, Cyclotrons and their Applications, Proceedings of the Fifteenth International Conference on Cyclotrons and their Applications, Caen, Franco, Jun. 14-19, 1998, pp. 21-23.

Hepburn et al., Superconducting Cyclotron Neutron Source for Therapy, International Journal of Radiation Oncology Biology Physics, vol. 3 complete, 1977, pp. 387-391.

Hirabayashi, Development of Superconducting Magnets for Beam Lines and Accelerator at KEK, IEEE Transaction on Magnetics, Jan. 1981, Mag-17(1 ):728-731.

Hyer, D. et al., A dynamic collimation system for penumbra reduction in spot-scanning proton therapy: Proof of concept; Medical Physics, 41(9):091701-1-091701-9 (2014).

Indiana's mega-million proton therapy cancer center welcomes its first patients [online] Press release, Health & Medicine Week, 2004, retrieved from NewsRx.com, Mar. 1, 2004, pp. 119-120.

International Preliminary Report on Patentability for PCT/US2014/071448, 14 pages (Jun. 30, 2016).

International Search Report and Written Opinion issued in corresponding PCT application No. PCT/US2014/071448 on Jul. 24, 2015 (18 pages).

International Search Report for PCT/US2016/048037, 11 pages (Feb. 6, 2017).

Invitation to Pay Additional Fees and, where applicable, protest fee issued in PCT application PCT/US2014/071448 on Apr. 13, 2015 (11 pages).

Invitation to Pay Additional Fees and, where applicable, protest fee issued in PCT application PCT/US2016/048037 on Oct. 20, 2016 (8 pages).

Ishibashi and Mcinturff, Stress Analysis of Superconducting 1 OT Magnets for Synchrotron, Proceedings of the Ninth International Cryogenic Engineering Conference, May 11-14, 1982, pp. 513-516.

Ishibashi and Mcinturff, Winding Design Study of Superconducting 10 T Dipoles for a Synchrotron, IEEE Transactions on Magnetics, May 1983, MAG-19(3):1364-1367.

Jahnke et al., First Superconducting Prototype Magnets for a Compact Synchrotron Radiation Source in Operation, IEEE Transactions on Magnetics, Mar. 1988, 24(2):1230-1232.

Jones and Dershem, Synchrotron Radiation from Proton in a 20 TEV, 10 Tesla Superconducting Super Collider Proceedings of the 12th International Conference on High-Energy Accelerator, Aug. 11-16, 1983, pp. 138-140.

Jones and Mills, The South African National Accelerator Centre: Particle Therapy and Isotope Production Programmes, Radiation Physics and Chemistry, Apr.-Jun. 1998, 51 ( 4-6):571-578.

Jones et al., Status Report of the NAC Particle Therapy Programme, Stralentherapie und Onkologie, vol. 175, Suppl. II, Jun. 1999, pp. 30-32.

Jones, Present Status and Future Trends of Heavy Particle Radiotherapy, Cyclotrons and their Applications 1998, Proceedings of the Fifteenth International Conference on Cyclotrons and their Applications, Jun. 14-19, 1998, pp. 13-20.

Jones, Progress with the 200 MeV Cyclotron Facility at the National Accelerator Centre, Commission of the European Communities Radiation Protection Proceedings, Fifth Symposium on Neutron Dosimetry, Sep. 17-21, 1984, vol. II, pp. 989-998.

Jongen et al., Development of a Low-cost Compact Cyclotron System for Proton Therapy, National Institute of Radiol. Sci,1991, No. 81, DD. 189-200.

Jongen et al., Progress report on the IBA-SHI small cyclotron for cancer therapy Nuclear Instruments and Methods in Physics Research, Section B, vol. 79, issue 1-4, 1993, pp. 885-889.

(56) References Cited

OTHER PUBLICATIONS

Jongen et al., The proton therapy system for MGH's NPTC: equipment description and progress report, Bulletin du Cancer/Radiotherapie, Proceedings of the meeting of the European Heavy Particle Therapy Group, 1996, 83(Suppl. 1):219-222.
Jongen et al., The proton therapy system for the NPTC: Equipment Description and progress report, Nuclear Instruments and methods in physics research, 1996, Section B, 113(1 ): 522-525.
Kanal et al., Three-dimensional Beam Scanning for Proton Therapy, Nuclear Instruments and Methods in Physic Research, Sep. 1, 1983, The Netherlands, 214(23):491-496.
Karlin et al., Medical Radiology (Moscow), 1983, 28, 13.
Karlin et al., The State and Prospects in the Development of the Medical Proton Tract on the Synchrocyclotron in Gatchina, Med. Radial., Moscow, 28(3):28-32 (Mar. 1983)(German with English Abstract on end of p. 32).
Kats and Druzhinin, Comparison of Methods for Irradiation Prone Patients, Atomic Energy, Feb. 2003, 94(2): 120-123.
Kats and Onosovskii, A Planar Magnetooptical System for the Irradiation of a Lying Patient with a Proton Beam from Various Directions, Instruments and Experimental Techniques, 1996, 39(1):127-131.
Kats and Onosovskii, A Simple, Compact, Flat System for the Irradiation of a Lying Patient with a Proton Beam from Different Directions, Instruments and Experimental Techniques, 1996, 39(1):132-134.
Khoroshkov et al., Moscow Hospital-Based Proton Therapy Facility Design, Am. Journal Clinical Oncology: CCT, Apr. 1994, 17(2):109-114.
Kim and Blosser, Optimized Magnet for a 250 MeV Proton Radiotherapy Cyclotron, Cyclotrons and Their Applications 2001, May 2001, Sixteenth International Conference, pp. 345-347.
Kim and Yun, A Light-Ion Superconducting Cyclotron System for Multi-Disciplinary Users, Journal of the Korean Physical Society, Sep. 2003, 43(3):325-331.
Kim et al., Construction of 8T Magnet Test Stand for Cyclotron Studies, IEEE Transactions on Applied Superconductivity, Mar. 1993, 3(1):266-268.
Kim et al., Design Study of a Superconducting Cyclotron for Heavy Ion Therapy, Cyclotrons and Their Applications 2001, Sixteenth International Conference, May 13-17, 2001, pp. 324-326.
Kim et al., Trim Coil System for the Riken Cyclotron Ring Cyclotron, Proceedings of the 1997 Particle Accelerator Conference, IEEE, Dec. 1981, vol. 3, pp. 214-235 or 3422-3424, 1998.
Kim, An Eight Tesla Superconducting Magnet for Cyclotron Studies, Ph.D. Dissertation, Michigan State University, Department of Physics and Astronomy, 1994, 13 8 pages.
Kimstrand, Beam Modelling for Treatment Planning of Scanned Proton Beams, Digital Comprehensive Summaries of Uppsala dissertations from the Faculty of Medicine 330. Uppsala Universitet, 2008, 58 pages.
Kishida and Yano, Beam Transport System for the RIKEN SSC (II), Scientific Papers of the Institute of Physical and Chemical Research, Dec. 1981, 75(4):214-235.
Koehler et al., Range Modulators for Protons and Heavy Ions, Nuclear Instruments and Methods, 1975, vol. 131, pp. 437-440.
Koto and Tsujii, Future of Particle Therapy, Japanese Journal of Cancer Clinics, 2001, 47(1):95-98 [Lang.: Japanese], English abstract (htt12://sciencelinks.j12/jeast/article/200206/000020020601A05 I I 453 .nhn).
Kraft et al., Hadrontherapy in Oncology, U. Amaldi and Larsson, editors Elsevier Science, 1994, 161 pages.
Krevet et al., Design of a Strongly Curved Superconducting Bending Magnet for a Compact Synchrotron Light Source, Advances in Cryogenic Engineering, 1988, vol. 33, pp. 25-32.
Laisne et al., The Orsay 200 MeV Synchrocyclotron, IEEE Transactions on Nuclear Science, Apr. 1979, NS-26(2):1919-1922.
Larsson, B., et al., "The High-Energy Proton Beam as a Neurosurgical Tool," Nature vol. 182, pp. 1222-1223 (1958).
Larsson, Biomedical Program for the Converted 200-MeV Synchrocyclotron at the Gustaf Werner Institute, Radiation Research, 1985, 104:S310-S318.
Lawrence et al., Heavy particles in acromegaly and Cushing's Disease, in Endocrine and Norendocrine Hormone Producing Tumors (Year Book Medical Chicago, 1973, pp. 29-61.
Lawrence et al., Successful Treatment of Acromegaly: Metabolic and Clinical Studies in 145 Patients, The Journal of Clinical Endrocrinology and Metabolism, Aug. 1970, 31(2), 21 pages.
Lawrence et al., Treatment of Pituitary Tumors, (Excerpta medica, Amsterdam/American Elsevier, New York, 1973, pp. 253-262.
Lawrence, J.H., Proton Irradiation of the Pituitary Cancer, vol. 10, pp. 795-798 (1957).
Lecroy et al., Viewing Probe for High Voltage Pulses, Review of Scientific Instruments USA, Dec. 1960, 31(12):1354.
Lin et al., Principles and 10 Year Experience of the Beam Monitor System at the PSI Scanned Proton Therapy Facility, Center for Proton Radiation Therapy, Paul Scherrer Institute, CH-5232, Villigen PSI, Switzerland, 2007, 21 pages.
Linfoot et al., Acromegaly, in Hormonal Proteins and Peptides, edited by C.H. Li, 1975, pp. 191-246.
Literature Author and Keyword Search, Feb. 14, 2005, 44 pages.
Literature Keyword Search, Jan. 24, 2005, 98 pages.
Literature Search and Keyword Search for Synchrocyclotron, Jan. 25, 2005, 68 pages.
Literature Search by Company Name/Component Source, Jan. 24, 2005, 111 pages.
Literature Search, Jan. 26, 2005, 37 pages.
Livingston, M.S., et al. A Capillary Ion Source for the Cyclotron, Review Science Instruments, vol. 10, p. 9. 63-67, (1939).
LLNL, UC Davis Team Up to Fight Cancer, Lawrence Livermore National Laboratory, Apr. 28, 2006, SF-06-04-02, Livermore, California, pp. 1-4.
Machine translation of JP11-028252A from jpo website Jul. 17, 2015.
Mandrillon, High Energy Medical Accelerators, EPAC 90, 2nd European Particle Accelerator Conference, Jun. 12-16, 1990, 2:54-58.
Marchand et al., IBA Proton Pencil Beam Scanning: an Innovative Solution for Cancer Treatment, Proceedings of EPAC 2000, Vienna, Austria, 3 pages.
Marti et al., High Intensity Operation of a Superconducting Cyclotron, Proceedings of the I 4the International Conference, Cyclotrons and Their Applications, Oct. 1995, pp. 45-48 (Oct. 1995).
Martin, Operational Experience with Superconducting Synchrotron Magnets Proceedings of the 1987 IEEE Particle Accelerator Conference, Mar. 16-19, 1987, vol. 3 of 3: 1379-1382.
Meote et al., ETOILE Hadrontherapy Project, Review of Design Studies Proceedings of EPAC 2002, 2002, pp. 2745-2747.
Miyamoto et al., Development of the Proton Therapy System, The Hitachi Hyoron, 79(10):775-775 779 (1997) [Lang: Japanese], English abstract (http://www.hitachi.com/rev/1998/revfeb98/rev4 706.htm).
Montelius et al., The Narrow Proton Beam Therapy Unit at the Svedberg Laboratory in Uppsala, ACTA Oncologica, 1991, 30:739-745.
Moser et al., Nonlinear Beam Optics with Real Fields in Compact Storage Rings, Nuclear Instruments & Methods in Physics Research/Section B, B30, Feb. 1988, No. 1, pp. 105-109.
Moyers et al., A Continuously Variable Thickness Scatterer for Proton Beams Using Self-compensating Dual Linear Wedges Loma Linda University Medical Center, Dept. of Radiation Medicine, Loma Linda, CA, Nov. 2, 1992, 21 pages.
National Cancer Institute Funding (Senate—Sep. 21, I 992} (www.tbomas.loc.gov/cgibin/querv/z?rl02:S21SE2-7l2 (2 pages).
Nicholson, Applications of Proton Beam Therapy, Journal of the American Society of Radiologic Technologists, May/Jun. 1996, 67(5): 439-441.
Nolen et al., The Integrated Cryogenic-Superconducting Beam Transport System Planned for MSU, Proceedings of the J21h International Conference on High-Energy Accelerators, Aug. 1983, pp. 549-551.

(56) References Cited

OTHER PUBLICATIONS

Norimine et al., A Design of a Rotating Gantry with Easy Steering for Proton Therapy, Proceedings of EPAC 2002, 2002, pp. 2751-2753.
Office Action for U.S. Appl. No. 14/137,854, 32 pages (Dec. 22, 2016).
Office Action for U.S. Appl. No. 14/137,854, 39 pages (Apr. 5, 2017).
Ogino, Takashi, Heavy Charged Particle Radiotherapy-Proton Beam, Division of Radiation Oncology, National Cancer Hospital East, Kashiwa, Japan, Dec. 2003, 7 pages.
Okumura et al., Overview and Future Prospect of Proton Radiotherapy, Japanese Journal of Cancer Clinics, 1997, 43(2):209-214 [Lang.: Japanese].
Okumura et al., Proton Radiotherapy Japanese Journal of Cancer and Chemotherapy, 1993, 10. 20(14):2149-2155[Lang.: Japanese].
Outstanding from Search Reports, Accelerator of Polarized Portons at Fermilab, 2005, 20 pages.
Paganetti et al., Proton Beam Radiotherapy—The State of the Art, Springer Verlag, Heidelberg. ISBN 3-540-00321-5, Oct. 2005,36 pages.
Palmer and Tollestrup, Superconducting Magnet Technology for Accelerators, Annual Review of Nuclear and Particle Science, 1984, vol. 34, pp. 247-284.
Patent Assignee and Keyword Searches for Synchrocyclotron, Jan. 25, 2005, 78 pages.
Patent Assignee Search Paul Scherrer Institute, Library Services at Fish & Richardson P.C., Mar. 20, 2007, 40 pages.
Patent Prior Art Search for 'Proton Therapy System', Library Services at Fish & Richardson P.C., Mar. 20, 2007, 46 pages.
Pavlovic, Beam-optics study of the gantry beam delivery system for light-ion cancer therapy, Nuclear Instruments and Methods in Physics Research, Section A, Nov. 1997, 399(2):439-454(16).
Pedroni and Enge, Beam optics design of compact gantry for proton therapy Medical & Biological Engineering & Computing, May 1995, 33(3):271-277.
Pedroni et al., A Novel Gantry for Proton Therapy at the Paul Scherrer Institute, Cycloctrons and Their Applications 2001: Sixteenth International Conference. AIP Conference Proceedings, 2001, 600:13-17.
Pedroni et al., The 200-MeV proton therapy project at the Paul Scherrer Institute: Conceptual design and practical realization, Medical Physics, Jan. 1995, 22(1 ):37-53.
Pedroni, Accelerators for Charged Particle Therapy: Performance Criteria from the User Point of View, Cyclotrons and their Applications, Proceedings of the 13th International Conference, Jul. 6-10, 1992, pp. 226-233.
Pedroni, E. and Jermann, M. "SGSMP: Bulletin Mar. 2002 Proscan Project, Progress Report on the PROSCAN Project of PSI," [online] retrieved from www.sgsmp.ch/protA23.htm, (5 pages) Mar. 2002.
Pedroni, Latest Developments in Proton Therapy Proceedings of EPAC 2000, pp. 240-244, 2000.
Pedroni, Status of Proton Therapy: results and future trends, Paul Scherrer Institute, Division of Radiation Medicine, 1994, 5 pages.
Peggs et al., A Survey of Hadron Therapy Accelerator Technologies, Particle Accelerator Conference, Jun. 25-29, 2008, 7 pages.
Potts et al., MPWP6-Therapy III: Treatment Aids and Techniques Medical Physics, Sep./Oct. 1988, 15(5):798.
Pourrahimi et al., Powder Metallurgy Processed Nb3Sn(Ta) Wire for High Field NMR magnets, IEEE Transactions on Applied Superconductivity, Jun. 1995, 5(2):1603-1606.
Prieels et al., The IBA State-of-the-Art Proton Therapy System, Performances and Recent Results, Application of Accelerators in Research and industry—Sixteenth Int'l. Conj, American Institute of Physics, Nov 1-5, 2000, 576:857-860.
Proiect of PSI [online] retrieved from www.sgsmp.ch/protA23.htm, Mar. 2002, 5 pages.
Rabin et al., Compact Designs for Comprehensive Proton Beam Clinical Facilities, Nuclear Instruments & Methods in Physics Research, Apr. 1989, Section B, vol. 40-41, Part II, pp. 1335-1339.
Research & Development Magazine, Proton Therapy Center Nearing Completion, Aug. 1999, 41(9):2 pages (www.rdmag.com).
Resmini,, Design Characteristics of the K=800 Superconducting Cyclotron at M.S.U., Cyclotron Laboratory, Michigan State University, East Lansing, Michigan 48824, IEEE Transaction on Nuclear Science, vol. NS-26, No. 2, Apr. 1979, 8 pages.
RetroSearch Berkeley 88-Inch Cyclotron 'RF' or 'Frequency Control', Jan. 21, 2005, 36 pages.
RetroSearch Berkeley 88-Inch Cyclotron, Jan. 24, 2005, 170 pages.
RetroSearch Bernard Gottschalk, Cyclotron, Beams, Compensated Upstream Modulator, Compensated Scatter, Jan. 21, 2005, 20 pages.
RetroSearch Cyclotron with 'RF' or 'Frequency Control', Jan. 21, 2005, 49 pages.
RetroSearch Gottschalk, Bernard, Harvard Cyclotron Wheel, Jan. 21, 2005, 20 pages.
RetroSearch Loma Linda University Beam Compensation, Jan. 21, 2005, 60 pages.
RetroSearch Loma Linda University, Beam Compensation Foil Wedge, Jan. 21, 2005, 15 pages.
Revised Patent Keyword Search, Jan. 25, 2005, 86 pages.
Rifuggiato et, al., Status Report of the LNS Superconducting Cyclotron Nukleonika, 2003, 48:SI31-SI34, Supplement 2.
Rode, Tevatron Cryogenic System, Proceedings of the 12th International Conference on Highenergy Accelerators, Fermilab, Aug. 11-16, 1983, pp. 529-535.
Salzburger et al., Superconducting Synchrotron Magnets Supraleitende Synchrotronmagnete, NTIS, 155 pages (Oct. 1975).
Schillo et al,. Compact Superconducting 250 MeV Proton Cyclotron for the PSI Proscan Proton Therapy Project, Cyclotrons and Their Applications 2001, Sixteenth International Conference, 2001, pp. 37-39.
Schneider et al., Nevis Synchrocyclotron Conversion Program—RF System, IEEE Transactions on Nuclear Science USA, Jun. 1969, ns 16(3): 430-433.
Schneider et al., Superconducting Cyclotrons, IEEE Transactions on Magnetics, vol. MAG-11, No. 2, Mar. 1975, New York, pp. 443-446.
Schreuder et al., The Non-orthogonal Fixed Beam Arrangement for the Second Proton Therapy Facility at the National Accelerator Centre, Application of Accelerators in Research and Industry, American Institute of Physics, Proceedings of the Fifteenth International Conference, Nov. 1998, Part Two, pp. 963-966.
Schreuder, Recent Developments in Superconducting Cyclotrons, Proceedings of the 1995 Particle Accelerator Conference, May 1-5, 1995, vol. 1, pp. 317-321.
Schubert and Blosser, Conceptual Design of a High Field Ultra-Compact Cyclotron for Nuclear Physics Research, Proceedings of the 1997 Particle Accelerator Conference, May 12-16, 1997, vol. 1, 3 pp. 1060-1062.
Schubert et al., Progress toward an experiment to study the effect of RF grounding in an internal ion source on axial oscillations of the beam in a cyclotron, National Superconducting Cyclotron Laboratory, Michigan State University, Report MSUCL-760, CP600, Cyclotrons and their Applications 2011, Sixteenth International Conference, 2001, pp. 274-276.
Schubert, Extending the Feasibility Boundary of the Isochronous Cyclotron, Dissertation submitted to Michigan State University, 1997, Abstract http://adsabs.harvard.edu/abs/1998PhDT ....... 147S.
Shelaev et al., Design Features of a Model Superconducting Synchrotron of JINR. Proceedings of the 12th International Conference on High-energy Accelerators, Aug. 11-16, 1983, pp. 416-418.
Shintomi et al., Technology and Materials for the Superconducting Super Collider (SSC) Project, The Iron and Steel Institute of Japan 00211575, 78(8): 1305-1313, 1992, [English Abstract included].
Siemens A.G., Erlangen (West Germany). Abteilung Technische Physik, Report No. BMFT-FB-T-75-25, Oct. 1975, p. 147, Journal Announcement: GRAI7619; STAR1415, Subm—Sponsored by Bundesmin. Fuer Forsch. U. Technol. In German; English Summary.
Sisterson, Clinical use of proton and ion beams from a world-wide perspective, Nuclear Instruments and Methods in Physics Research, Section B, 1989, 40-41:1350-1353.

(56) References Cited

OTHER PUBLICATIONS

Sisterson, World Wide Proton Therapy Experience in 1997, The American Institute of Physics, Applications of Accelerators in Research and Industry, Proceedings of the Fifteenth International Conference, Part Two, Nov. 1998, pp. 959-962.

Slater et al., Developing a Clinical Proton Accelerator Facility: Consortium-Assisted Technology Transfer, Conference Record of the 1991 IEEE Particle Accelerator Conference: Accelerator Science and Technology, vol. I, May 6-9, 1991, pp. 532-536.

Slater et al., Development of a Hospital-Based Proton Beam Treatment Center, International Journal of Radiation Oncology, Biology and Physics, Apr. 1988, 14(4):761-775.

Smith et al., The Northeast Proton Therapy Center at Massachusetts General Hospital Journal of Brachytherapy International, Jan. 1997, pp. 137-139.

Snyder and Marti, Central region design studies for a proposed 250 MeV proton cyclotron, Nuclear Instruments and Methods In Physics Research, Section A, 1995, vol. 355, pp. 618-623.

Soga, Progress of Particle Therapy in Japan, Application of Accelerators in Research and Industry, American Institute of Physics, Sixteenth International Conference, Nov. 2000, pp. 869-872.

Source Search "Cites of U.S. and Foreign Patents/Published applications in the name of Mitsubishi Denki Kabushiki Kaisha and Containing the Keywords (Proton and Synchrocyclotron)," Jan. 2005, 8 pages.

Spiller et al., The GSI Synchrotron Facility Proposal for Acceleration of High Intensity Ion and Proton Beams Proceedings of the 2003 Particle Accelerator Conference, May 12-16, 2003, vol. 1, pp. 589-591.

Stanford et al., Method of Temperature Control in Microwave Ferroelectric Measurements, Sperry Microwave Electronics Company, Clearwater, Florida, Sep. 19, 1980, 1 page.

Superconducting Cyclotron Contract awarded by Paul Scherrer Institute (PSI), Villigen, Switzerland, http://www.accel.de/News/superconducting_ cyclotron_ contract.htm, Jan. 2009, 1 page.

Tadashi et al., Large superconducting super collider (SSC) in the planning and materials technology, 78(8):1305-1313, The Iron and Steel Institute of Japan 00211575, Aug. 1992.

Takada, Conceptual Design of a Proton Rotating Gantry for Cancer Therapy, Japanese Journal of Medical Physics, 1995, 15(4):270-284.

Takayama et al., Compact Cyclotron for Proton Therapy, Proceedings of the 81h Symposium on Accelerator Science and Technology, Japan, Nov. 25-27, 1991, pp. 380-382.

Teng, The Fermilab Tevatron, Coral Gables 1981, Proceedings, Gauge Theories, Massive Neutrinos, and Proton Decay, 1981, pp. 43-62.

The Davis 76-Inch Isochronous Cyclotron, Beam on: Crocker Nuclear Laboratory, University of California, 2009, 1 page.

The Journal of Practical Pharmacy,1995, 46(1):97-103 [Japanese].

The K100 Neutron-therapy Cyclotron, National Superconducting Cyclotron Laboratory at Michigan State University (NSCL ), retrieved from: http://www.nscl.msu.edu/tech/accelerators/kl 00, Feb. 2005, 1 page.

The K250 Proton therapy Cyclotron, National Superconducting Cyclotron Laboratory at Michigan State University (NSCL), retrieved from: http://www.nscl.msu.edu/tech/accelerators/k.250.html, Feb. 2005, 2 pages.

The K250 Proton-therapy Cyclotron Photo Illustration, National Superconducting Cyclotron Laboratory at Michigan State University (NSCL), retrieved from: http://www.nscl.msu.edu/media/image/ experimental-equipment-technology /25 0 .html, Feb. 2005, 1 page.

Tilly, et al., Development and verification of the pulsed scanned proton beam at the Svedberg Laboratory in Uppsala, Physics in Medicine and Biology, Phys. Med. Biol. 52, pp. 2741-2454, 2007.

Tobias, C.A., et al., Pituitary Irradiation with High-Energy Proton Beams a Preliminary Report, Cancer Research, vol. 18, No. 2, pp. 121-134 (1958).

Tom, The Use of Compact Cyclotrons for Producing Fast Neutrons for Therapy in a Rotatable Isocentric Gantry, IEEE Transaction on Nuclear Science, Apr. 1979, 26(2):2294-2298.

Torikoshi, M. et al., Irradiation System for HIMAC, J. Radiat. Res, 48: Suppl. A15-A25 (2007).

Toyoda, Proton Therapy System, Sumitomo Heavy Industries, Ltd., 2000, 5 pages.

Trinks et. al., The Tritron: A Superconducting Separated-Orbit Cyclotron, Nuclear Instruments and Methods in Physics Research, Section A, 1986, vol. 244, pp. 273-282.

Tsuji, The Future and Progress of Proton Beam Radiotherapy, Journal of Japanese Society for Therapeutic Radiology and Oncology, 1994, 6(2):63-76.

U.S. Appl. No. 13/830,792, including the USPTO electronic file for U.S. Appl. No. 13/830,792.

U.S. Appl. No. 13/949,459, filed Jul. 24, 2013, including the USPTO electronic file for 13/949,459.

U.S. Appl. No. 61/676,377, including the USPTO electronic file for U.S. Appl. No. 61/676,377.

UC Davis School of Medicine, Unlikely Partners Turn Military Defense into Cancer Offense, Current Issue Summer 2008, Sacramento, California, pp. 1-2.

Umegaki et al., Development of an Advanced Proton Beam Therapy System for Cancer Treatment Hitachi Hyoron, 2003, 85(9):605-608 [Lang.: Japanese], English abstract, http://www.hitachi.com/ICSFiles/afieldfile/2004/06/0 1/r2003 _ 04_ 1 04.pdf or http://www.hitachi.com/rev/archive/2003/2005649_12606.html (full text) [Hitachi, 52(4), Dec. 2003].

Umezawa et al., Beam Commissioning of the new Proton Therapy System for University of Tsukuba, Proceedings of the 2001 Particle Accelerator Conference, vol. 1, Jun. 18-22, 2001, pp. 648-650.

Van Steenbergen, Superconducting Synchroton Development at BNL, Proceedings of the 8th Intemational Conference on High-Energy Accelerators CERN 1971, 1971, pp. 196-198.

Van Steenbergen, The CMS, a Cold Magnet Synchrotron to Upgrade the Proton Energy Range of the BNL Facility, IEEE Transactions on Nuclear Science, Jun. 1971, 18(3):694-698.

Vandeplassche et al., 235 MeV Cyclotron for MGH's Northeast Proton Therapy Center (NPTC): Present Status, EPAC 96, Fifth European Partical Accelerator Conference, vol. 3, Jun. 10-14, 1996, pp. 2650-2652.

Vorobiev et al., Concepts of a Compact Achromatic Proton Gantry with a Wide Scanning Field, Nuclear Instruments and Methods in Physics Research, Section A., 1998, 406(2):307-310.

Vrenken et al., A Design of a Compact Gantry for Proton Therapy with 2D-Scanning, Nuclear Instruments and Methods in Physics Research, Section A, 1999, 426(2):618-624.

Wikipedia, Cyclotron http://en.wikipedia.org/wiki/Cyclotron (originally visited Oct. 6, 2005, revisited Jan. 28, 2009), 7 pages.

Wikipedia, Synchrotron http://en.wikipedia.org/wiki/Synchrotron (originally visited Oct. 6, 2005, revisited Jan. 28, 2009), 7 pages.

Worldwide Patent Assignee Search, Jan. 24, 2005, 224 pages.

Worldwide Patent Keyword Search, Jan. 24, 2005, 94 pages.

Written Opinion for PCT/US2016/048037, 12 pages (Feb. 6, 2017).

Wu, Conceptual Design and Orbit Dynamics in a 250 MeV Superconducting Synchrocyclotron, Ph.D. Dissertation, Michigan State University, Department of Physics and Astronomy, 1990, 172 pages.

York et al., Present Status and Future Possibilities at NSCL-MSU, EP AC 94, Fourth European Particle Accelerator Conference, pp. 554-556, Jun. 1994.

York et al., The NSCL Coupled Cyclotron Project—Overview and Status, Proceedings of the Fifteenth International Conference on Cyclotrons and their Applications, Jun. 1998, pp. 687-691.

Yudelev et al., Hospital Based Superconducting Cyclotron for Neutron Therapy: Medical Physics Perspective, Cyclotrons and their applications 2001, 16th International Conference. American Institute of Physics Conference Proceedings, vol. 600, May 13-17, 2001, pp. 40-43.

Zherbin et al., Proton Beam Therapy at the Leningrad Synchrocyclotron (Clinicomethodological Aspects and Therapeutic Results), Aug. 1987, 32(8):17-22, (German with English abstract on pp. 21-22).

(56) References Cited

OTHER PUBLICATIONS

Boyer, A. et al., Basic Applications of Multileaf Collimators: Report of Task Group No. 50—Radiation Therapy Committee, AAPM Report No. 72, American Association of Physicists in Medicine by Medical Physics Publishing, 62 pages (2001).
Daartz, J. et al., Characterization of a mini-multileaf collimator in a proton beamline, Med. Phys., 36(5):9 pages (2009).
Fredriksson, Albin, Robust optimization of radiation therapy accounting for geometric uncertainty, Doctoral Thesis, 57 pages (2013).
Gelover, E. et al., A method for modeling laterally asymmetric proton beamlets resulting from collimation, Medical Physics, 42:1321-1334 (2015).
Hyer, D. et al., A dynamic collimation system for penumbra reduction in spot-scanning proton therapy: Proof of concept, American Association of Physicists in Medicine, 10 pages (2014).
Moignier, A. et al., Toward improved target conformity for two spot scanning proton therapy delivery systems using dynamic collimation, Medical Physics, 43:1421-1427 (2014).
Notification of Receipt of Search Copy for PCT/US2017/041076, 1 page (Aug. 1, 2017).

\* cited by examiner

TREATMENT PLANNING

CROSS-REFERENCE TO RELATED APPLICATIONS

This application is a continuation of U.S. patent application Ser. No. 15/643,865, which was filed on Jul. 7, 2017; U.S. patent application Ser. No. 15/643,865 claiming the benefit of priority of U.S. Provisional Application No. 62/360,227, which was filed on Jul. 8, 2016, and which is entitled "Treatment Planning". The contents of U.S. patent application Ser. No. 15/643,865 and of U.S. Provisional Application No. 62/360,227 is are incorporated herein by reference.

TECHNICAL FIELD

This disclosure relates generally to treatment planning in a particle therapy system.

BACKGROUND

Particle therapy systems use an accelerator to generate a particle beam for treating afflictions, such as tumors. In operation, particles are accelerated in orbits inside a cavity in the presence of a magnetic field, and are removed from the cavity through an extraction channel. A magnetic field regenerator generates a magnetic field bump near the outside of the cavity to distort the pitch and angle of some orbits so that they precess towards, and eventually into, the extraction channel. A beam, comprised of the particles, exits the extraction channel.

The particle beam can damage healthy tissue adjacent to the irradiation target. A structure may be used to limit exposure of the healthy tissue to the particle beam. For example, the structure, or a portion thereof, may be placed in between the particle beam and the healthy tissue, thereby preventing exposure of the healthy tissue to the particle beam.

SUMMARY

An example method includes receiving, from a treatment planning process, information that is based on a dose distribution for an irradiation target; and configuring an adaptive aperture based on the information. The example method may include one or more of the following features, either alone or in combination.

The information received from the treatment planning process may identify structures of the adaptive aperture; and configuring the adaptive aperture may comprise moving the structures of the adaptive aperture to produce a trimming curve. The information may identify characteristics of a trimming curve; and configuring the adaptive aperture may comprise moving structures of the adaptive aperture to produce the trimming curve. The information my identify characteristics of pre-trimmed spots, which characteristics are stored in a library in computer memory; and configuring the adaptive aperture may comprise moving structures of the adaptive aperture to trim spots of a particle beam so that the spots of the particle beam approximate the pre-trimmed spots. The information may indicate where spots are to be formed on the irradiation target; and configuring the adaptive aperture may comprise moving structures of the adaptive aperture based on where the spots are to be formed on the irradiation target. The information may identify characteristics of spots; and configuring the adaptive aperture may comprise moving structures of the adaptive aperture on a spot-by-spot basis.

Configuring the adaptive aperture may comprise moving structures of the adaptive aperture so that at least two successive spots have at least one of a different size or a different shape. The information may comprise specifications of a trimming curve for a radiation field associated with the irradiation target; and configuring the adaptive aperture may comprise moving structures of the adaptive aperture to produce the trimming curve. The specifications may identify at least one of shape or a location of the trimming curve relative to a known point. The information may comprise specifications of distinct trimming curves for different layers of the irradiation target; and configuring the adaptive aperture may comprise moving structures of the adaptive aperture to produce a trimming curve for each layer of the irradiation target based on specifications for the each layer.

The information received from the treatment planning process may comprise specifications of a single trimming curve for a radiation field associated with the irradiation target; and configuring the adaptive aperture may comprise moving structures of the adaptive aperture to produce the single trimming curve. The single trimming curve may be used to trim a radiation field for multiple layers of the irradiation target. The information may comprise specifications for a configuration of the adaptive aperture for a radiation field of the irradiation target; and configuring the adaptive aperture may comprise moving structures of the adaptive aperture based on the specifications for the configuration of the adaptive aperture. The information may comprise specifications of configurations of the adaptive aperture for different layers of the irradiation target; and configuring the adaptive aperture may comprise moving structures of the adaptive aperture for the different layers of the irradiation target based on the information.

The adaptive aperture may comprise: structures that are movable relative to the irradiation target to produce a shape to trim part of a treatment area; and a primary carriage coupled to the structures to move the structures relative to the irradiation target in a first dimension relative to the irradiation target. Configuring the adaptive aperture may comprise moving at least one of a structure among the structures or the primary carriage. The adaptive aperture may comprise secondary carriages coupled to the primary carriage and to the structures to move the structures in a second dimension relative to the irradiation target. Configuring the adaptive aperture may comprise moving at least one of the secondary carriages. The second dimension may comprise movement into, and out of, the treatment area. Moving at least one of the secondary carriages may comprise rotating the at least one secondary carriage. The structures may comprise leaves that are extendible and retractable relative to the particle beam. Configuring the adaptive aperture may comprise rotating all or part of the adaptive aperture.

An example method comprises receiving, from a treatment planning process, information that is based on a dose distribution for an irradiation target; and performing at least one of the following operations: moving structures to trim spots of a particle beam so that the spots of the particle beam approximate pre-trimmed spots for which characteristics are obtained based on the information received; moving structures to produce a trimming curve for a layer of an irradiation target based on a specification of a trimming curve for the layer included in the information received; moving structures to produce a single trimming curve for all radiation fields of an irradiation target based on specifications of the single trimming curve included in the information received; or moving structures based on configuration information for the structures in the information received. The structures may be part of an adaptive aperture and may comprise leaves that are movable into, or out of, an area to be treated by the particle beam. The information may specify a configuration of the leaves and/or carriage(s) holding the leaves.

An example particle therapy system comprises: a particle accelerator to output a particle beam for application to an irradiation target; an adaptive aperture between the particle accelerator and the irradiation target, where the adaptive aperture comprises structures that are movable into, and out of, a path of the particle beam; and a control system comprising one or more processing devices configured to perform various operations. The various operations may comprise: receiving, from a treatment planning process, information that is based on a dose distribution for the irradiation target; and configuring the adaptive aperture based on the information. The example particle therapy system may include one or more of the following features, either alone or in combination.

The information based on the dose distribution may identify characteristics of pre-trimmed spots, with the characteristics being stored in a library in computer memory; and configuring the adaptive aperture may comprise moving structures of the adaptive aperture to trim spots of a particle beam so that the spots of the particle beam approximate the pre-trimmed spots. The information may indicate where the pre-trimmed spots are to be formed on the irradiation target; and configuring the adaptive aperture may comprise moving structures of the adaptive aperture based on where the pre-trimmed spots are to be formed on the irradiation target. The characteristics may comprise one or more parameters, with the one or more parameters comprising at least one of a radius associated with a spot or an angle of rotation of the spot. The information may identify characteristics of spots; and configuring the adaptive aperture may comprise moving structures of the adaptive aperture on a spot-by-spot basis.

Configuring the adaptive aperture may comprise moving structures of the adaptive aperture so that at least two successive spots have at least one of a different size or a different shape. Configuring the adaptive aperture may comprise maintaining structures of the adaptive aperture so that at least two successive spots have at least one of a same size or a same shape. The information may comprise specifications of a trimming curve for a radiation field associated with the irradiation target; and configuring the adaptive aperture may comprise moving structures of the adaptive aperture to produce the trimming curve. The specifications may identify at least one of shape or a location of the trimming curve relative to a known point.

The information based on the dose distribution may comprise specifications of trimming curves for different layers of the irradiation target; and configuring the adaptive aperture may comprise moving structures of the adaptive aperture to produce a trimming curve for each layer of the irradiation target based on specifications for the each layer. The information may comprise specifications of a single trimming curve for a radiation field associated with the irradiation target; and configuring the adaptive aperture may comprise moving structures of the adaptive aperture to produce the single trimming curve, with the single trimming curve being used to trim a radiation field for multiple layers of the irradiation target.

The information may comprise specifications for a configuration of the adaptive aperture for a radiation field of the irradiation target; and configuring the adaptive aperture may comprise moving structures of the adaptive aperture based on the specifications for the configuration of the adaptive aperture. The information may comprise specifications of configurations of the adaptive aperture for different layers of the irradiation target; and configuring the adaptive aperture may comprise moving structures of the adaptive aperture for the different layers of the irradiation target based on the information. The adaptive aperture may comprise a primary carriage coupled to the structures to move the structures relative to the irradiation target in a first dimension relative to the irradiation target; and configuring an adaptive aperture may comprise moving at least one of a structure among the structures or the primary carriage. The adaptive aperture may comprise secondary carriages coupled to the primary carriage and to the structures to move the structures in a second dimension relative to the irradiation target; and configuring the adaptive aperture may comprise moving at least one of the secondary carriages.

The second dimension may comprise movement into, and out of, the treatment area. Moving at least one of the secondary carriages may comprise rotating the at least one secondary carriage. The structures may comprise leaves that are extendible and retractable relative to the particle beam. Configuring the adaptive aperture may comprise rotating all or part of the adaptive aperture.

An example particle therapy system comprises: a particle accelerator to output a particle beam for application to an irradiation target; and a control system comprising one or more processing devices configured to perform various operations. The operations comprise receiving, from a treatment planning process, information that is based on a dose distribution for the irradiation target; and performing at least one of the following operations: moving structures to trim spots of the particle beam so that the spots of the particle beam approximate pre-trimmed spots for which characteristics are obtained based on the information received; moving structures to produce a trimming curve for a layer of an irradiation target based on a specification of a trimming curve for the layer included in the information received; moving structures to produce a single trimming curve for all radiation fields of an irradiation target based on specifications of the single trimming curve included in the information received; or moving structures based on configuration information for the structures in the information received. The structures may be part of an adaptive aperture and may comprise leaves that are movable into, or out of, an area to be treated by the particle beam.

An example method that may be performed by a particle therapy system comprises obtaining a target dose distribution for a treatment area; identifying one or more pre-trimmed spots from among a library of pre-trimmed spots that best approximates one or more points of the target dose distribution; and outputting information identifying the one or more pre-trimmed spots. The example method may comprise one or more of the following features either alone or in combination.

The example method may comprise obtaining a set of coarse spots that approximates the target dose distribution; changing an intensity of one or more spots in the coarse set based on a maximum acceptable dosage for a portion of the treatment area; identifying a spot among the coarse spots that is within a transition region of the treatment area; and substituting the one or more pre-trimmed spots for the spot within the transition region. The example method may comprise obtaining a minimum acceptable dosage for a portion of the treatment area; where the set of coarse spots is selected based on the minimum acceptable dosage. The information may be usable to configure an adaptive aperture to achieve a dose distribution during treatment that approximates the target dose distribution.

An example method that may be performed by a particle therapy system comprises obtaining treatment planning information; determining that an irradiation target has moved since a prior application of radiation based on the treatment planning information; modifying the treatment planning information based on movement of the irradiation target to produce updated treatment planning information; and applying radiation to the irradiation target based on the updated treatment planning information. The example method may comprise one or more of the following features either alone or in combination.

Modifying the treatment planning information may be performed by a computing system of the particle therapy system. Determining that that irradiation target has moved may be based on a comparison of images of the irradiation target captured between two points in time. The treatment planning information may be modified by changing locations to which spots of radiation are to be applied to the irradiation target based on a location of the irradiation target following movement.

Two or more of the features described in this disclosure, including those described in this summary section, may be combined to form implementations not specifically described herein.

Control of the various systems described herein, or portions thereof, may be implemented via a computer program product that includes instructions that are stored on one or more non-transitory machine-readable storage media, and that are executable on one or more processing devices (e.g., microprocessor(s), application-specific integrated circuit(s), programmed logic such as field programmable gate array(s), or the like). The systems described herein, or portions thereof, may be implemented as an apparatus, method, or electronic system that may include one or more processing devices and computer memory to store executable instructions to implement control of the stated functions.

The details of one or more implementations are set forth in the accompanying drawings and the description below. Other features, objects, and advantages will be apparent from the description and drawings, and from the claims.

DESCRIPTION OF THE DRAWINGS

Like reference symbols in the various drawings indicate like elements.

DETAILED DESCRIPTION

Figure 1:
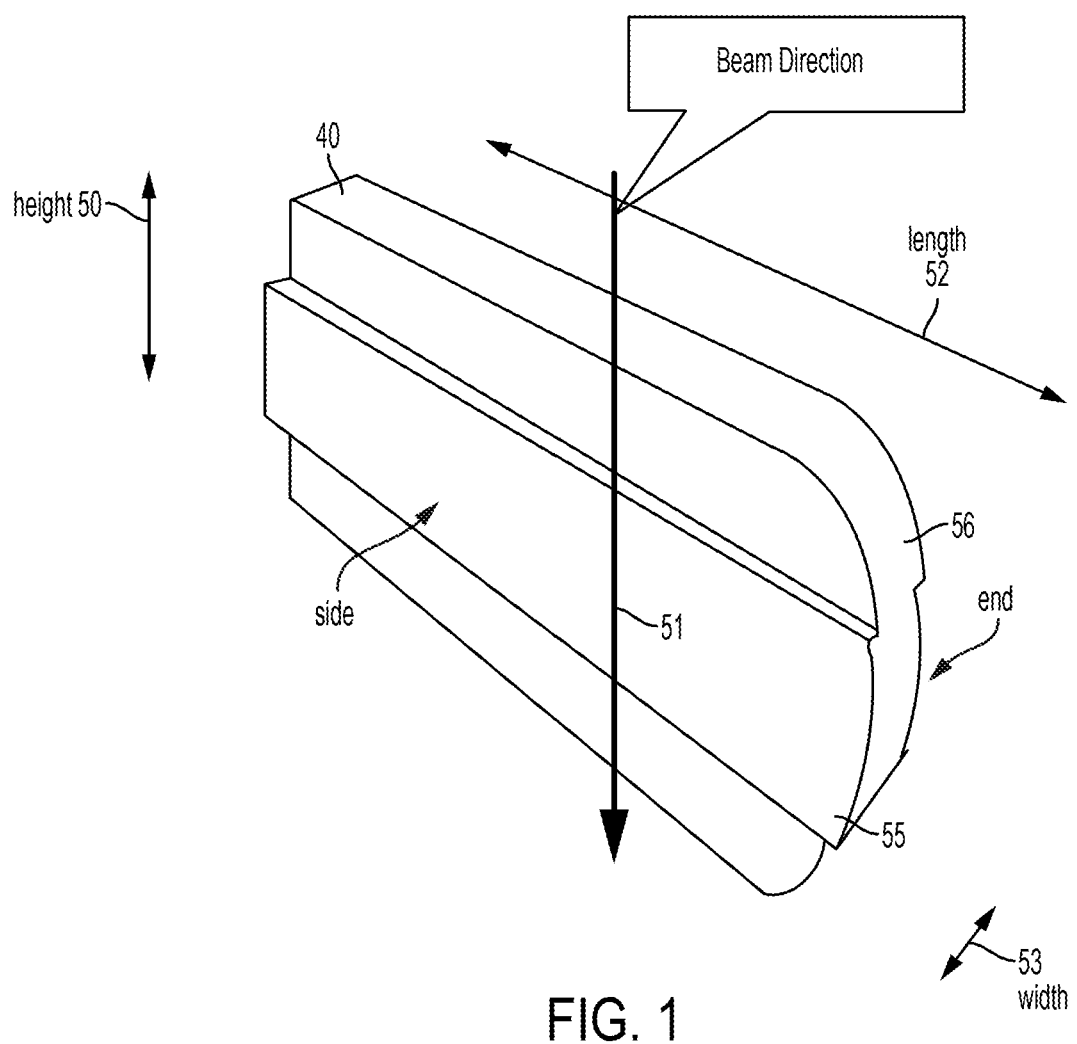
FIG. 1 is a perspective view of an example adaptive aperture leaf that is usable with the example adaptive apertures described herein.

Described herein are example implementations of an adaptive aperture (also called a "configurable collimator") that may be used to control the extent of radiation, such as a proton or ion beam, applied to a patient. In some implementations, an adaptive aperture includes structures that are controllable to allow some radiation to pass to a patient and to block some radiation from passing to the patient. Typically, the radiation that passes is directed to an irradiation target to be treated, and the radiation that is blocked would otherwise hit, and potentially damage, healthy tissue. Radiation internal to the target may be blocked as well in order to achieve a target dose distribution. In an example operation, the adaptive aperture is placed in the radiation path between a radiation source and an irradiation target and is controlled to produce a trimming curve of an appropriate size and shape. A trimming curve may be an open-ended curve or a closed curve, such as an opening that allows some radiation to pass to the irradiation target, while preventing some radiation from reaching adjacent tissue. The adaptive aperture may be used in any appropriate radiation therapy system, and is not limited to use with any particular type of system, including those described herein. Examples of systems with which the adaptive aperture may be used are described herein.

In some implementations, the adaptive aperture contains generally flat structures, which are referred to as "plates" or "leaves", and which are controllable to move into the "beam" or "treatment" area to block some radiation and allow some radiation to pass. The leaves are controllable to produce an opening of size and shape that is appropriate for the current treatment. In some implementations, the leaves are held on two carriages, and face each other and the treatment area. The leaves are controllable to move into, and out of, the treatment area, to form the opening (or aperture) though which the particle beam passes to treat an area of a patient. The leaves that form the opening also block radiation from passing to tissue (e.g., healthy tissue) adjacent to the opening that is covered by the leaves. In this context, covering includes the leaves blocking the particle beam. The leaves, or a portion thereof, may be placed in between the particle beam and target tissue to create sharp dose gradients which may better optimize the dose distribution to satisfy an objective function when combined with other particle beams.

In some implementations, each set of leaves is configurable to define an edge that is movable into a path of the particle beam so that a first part of the particle beam on a first side of the edge is blocked by the leaves, and so that a second part of the particle beam on a second side of the edge is not blocked by the leaves and is allowed to pass to the treatment area. In some implementations the leaves are connected to, are part of, or include, motors—one per leaf—that are controllable to control movement of the leaves towards or away from the treatment area to define the edge. In some implementation, the motors may be linear motors. An example linear motor includes a movable component and a stationary component. The stationary component may include a magnetic field generator, such as two magnets having their poles aligned, to generate a first magnetic field. The movable component may be sandwiched between the two magnets and may include one or more coils to conduct current to produce a second magnetic field that interacts with the first magnetic field to cause the moveable component to move relative to the stationary component. The movable component of each linear motor is connected to, or part of, a corresponding one of the leaves such that the corresponding leaf moves along with movement with the movable component.

FIG. 1 shows an example of a leaf 40 that may be used in the adaptive aperture, although the adaptive aperture is not limited to use with this type of leaf. The height 50 of the leaf is along the beamline (e.g., the direction of the particle beam). The length 52 of the leaf is along its direction of actuation into and out of the treatment area, and is based on the field size, or portion thereof, that the system can treat. The field size corresponds to the treatment area that the beam can impact. The width 53 of the leaf is the direction along which multiple leaves stack when actuated. Generally, the more leaves that are used, the higher the resolution of the trimming curve that can be produced, including for curved boundaries.

In FIG. 1, leaf 40 includes a tongue and groove feature 55 along its side, which is configured to reduce inter-leaf leakage when multiple such leaves stack. In this example, the curved end 56 of leaf 40 is configured to maintain a surface tangent to the beam at all locations in the treatment area. However, in some implementations, the end of each leaf may be flat, not curved.

In some implementations, the adaptive aperture leaves have a height that is sufficient to block at least the maximum beam energy (e.g., the maximum energy of the particle beam output by a particle therapy system). In some implementations, the adaptive aperture leaves have a height that blocks less than the maximum beam energy, for reasons described below. In some implementations, the adaptive aperture leaves have lengths that are dictated not by the area of an entire treatment area, but rather by the area of a single beam spot or multiple beam spots. In this context, a "beam spot" includes the cross-sectional area of a particle beam. In some implementations, the adaptive aperture is controllable to move into the "beam" or "treatment" area to block some radiation and allow some radiation to pass from an individual or multiple beam spot(s).

In an example, the particle therapy system may be configured to treat a tumor having a cross-section that can fit into a 20 cm×20 cm square area. In this example, each leaf in the adaptive aperture may have a length of about 2 cm, which is about enough to block particles in half of one beam spot. As noted, the adaptive aperture may include sets of leaves that face each other. So, leaves from each set may be controlled to cover the whole, single beam spot, if necessary, thereby preventing passage of radiation. The leaves may also be controllable to create one or more trimming curves that define an opening through which some, or all, of the radiation from the single beam spot can pass.

In operation, the adaptive aperture is configured to move as the beam scans across the radiation target, and to track the beam's movement during scanning. In an example, the adaptive aperture may be configured to move about 20 cm so as to enable coverage over the entirety of the 20 cm×20 cm area. As described above, the adaptive aperture may be configured to use enough leaves to cover (or "trim") one beam spot and, in some case, a small amount of extra area (e.g., 5% extra area, 10% extra area, 15% extra area, or 20% extra area).

Figure 2:
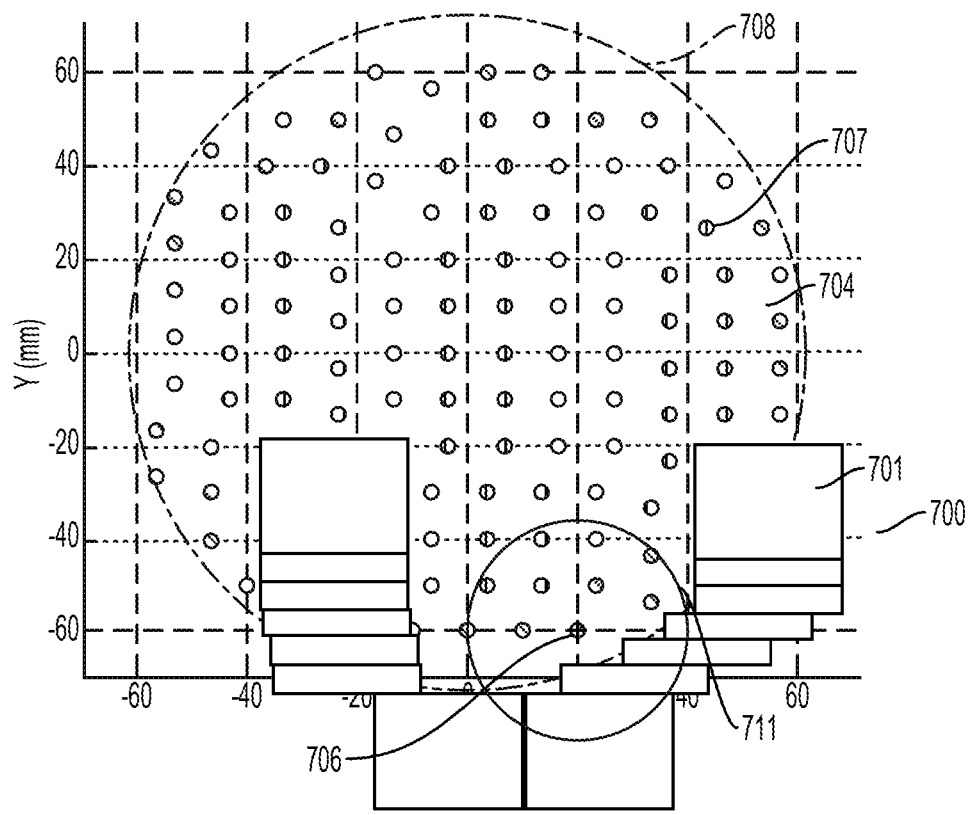
FIG. 2 is a top view of an example adaptive aperture leaves positioned relative to a treatment area of an irradiation target.

FIG. 2 shows an example implementation of an adaptive aperture 700. In this example, adaptive aperture 700 includes leaves 701 having a height and made of a material, such as nickel, brass, tungsten, or other metal, sufficient to inhibit or prevent passage of radiation at a given energy. For example in some systems, a particle accelerator is configured to generate a particle beam having a maximum energy of 100 MeV to 300 MeV. Accordingly, in such systems, the leaves may be constructed to prevent passage of a beam having an energy of 100 MeV, 150 MeV, 200 MeV, 250 MeV, 300 MeV, and so forth.

Leaves 701 are mounted on carriages to control their movement relative to a treatment area of an irradiation target, such as a cross-sectional layer of a tumor in a patient. The movement is controlled to cause leaves 701 to cover some parts of treatment area 704, thereby preventing radiation from impacting those parts during treatment, while leaving other parts of treatment area exposed to the radiation. In the example implementation of FIG. 2, there are fourteen leaves in total—seven on the left and seven on the right. In some implementations, there may be a different number of leaves, e.g., ten in total, five on the left and five on the right, twelve in total, six on the left and six on the right, and so forth.

The adaptive aperture may be used with any appropriate type of radiation therapy system. In an example implementation, the radiation therapy system is a proton therapy system. As described herein, an example proton therapy system scans a proton beam across a treatment area of an irradiation target in order to destroy malignant tissue. During scanning, the particle beam moves across the treatment area to cover the treatment area with radiation. In an example implementation, the particle beam is pulsed. Even with pulsed beams, uniform dose coverage can be achieved with a single pass of the beam. Each spot may be hit with multiple pulses to account for random variability in the intensity of each pulse that cannot be controlled. The particle beam may be passed over the treatment area multiple times in order to mitigate organ motion effects due to patient motion (e.g., due to breathing). As a result, it may be beneficial to scan the same treatment area more than once. Each successive scan may be offset from one or more other scan(s). An example of this type of scanning is called pencil-beam scanning, and the repetitive scans are referred to as painting or repainting the treatment area.

The irradiation target is typically three-dimensional in structure. Accordingly, as described herein, the irradiation target is treated cross-sectional layer (or simply "layer") by layer. That is, a layer of the irradiation target is treated, followed by another treatment of another layer, and so forth until the entire target is treated. Different layers of an irradiation target are treated by varying an energy level of the particle beam. That is, different energy levels of the particle beam impact different layers of the irradiation target, with higher energy levels affecting layers deeper inside the irradiation target relative to the particle beam source. Accordingly, during treatment, the energy level of the particle beam is changed in order to reach, and thus treat, different layers of the irradiation target.

FIG. 2 shows leaves 701 configured to allow radiation to impact part of a layer (e.g., the treatment area) and to prevent radiation from impacting other parts of the layer (e.g., healthy tissue). In FIG. 2, locations 707 represent centers of beam spots to be delivered during a scan of a proton beam across treatment area 704. Circle 708 represents a treatment boundary beyond which no radiation is intended to be delivered. Beam spots that are close to this boundary (e.g., within one standard deviation of the particle beam's profile) border healthy tissue. These are spots that are trimmed (that is, blocked) by appropriate configuration and placement of leaves on the adaptive aperture. An example of a beam spot to be trimmed is beam spot 711, having its center at location 706. As shown, ones of leaves 701 are configured to block the portion of beam spot 711 that extends beyond circle 708.

In an example implementation, on each of two separate carriages, there are five leaves that are about 5 mm in width and two leaves that are about 20 mm in width, for a total of seven leaves per carriage. Thus, in some implementations, on each of two separate carriages, there are seven leaves, two of which each have widths that are three times or more the widths of each of five other leaves. Other implementations may contain different numbers, sizes, and configurations of leaves, and different numbers and configurations of carriages. For example, some implementations may include any number between five and fifty leaves per carriage, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 leaves (or more) per carriage.

The carriages can move both horizontally and vertically, as described herein. The leaves are also movable horizontally relative to each carriage into, and out of, the treatment area. In this way, the leaves are configurable to approximate the shape of the treatment boundary in the region near the area being treated (e.g., circle 711 or a portion thereof in this example).

The leaves may be moved vertically and/or horizontally between different scans of the particle beam so that the leaves are in appropriate positions when the beam is delivered to a particular area. The leaves need not necessarily be moved for every scan pass, but instead may be moved to a location appropriate for an area. In some cases, e.g., for spots interior to the treatment area, radiation treatment may proceed without the trimming provided by the adaptive aperture.

Figure 30:
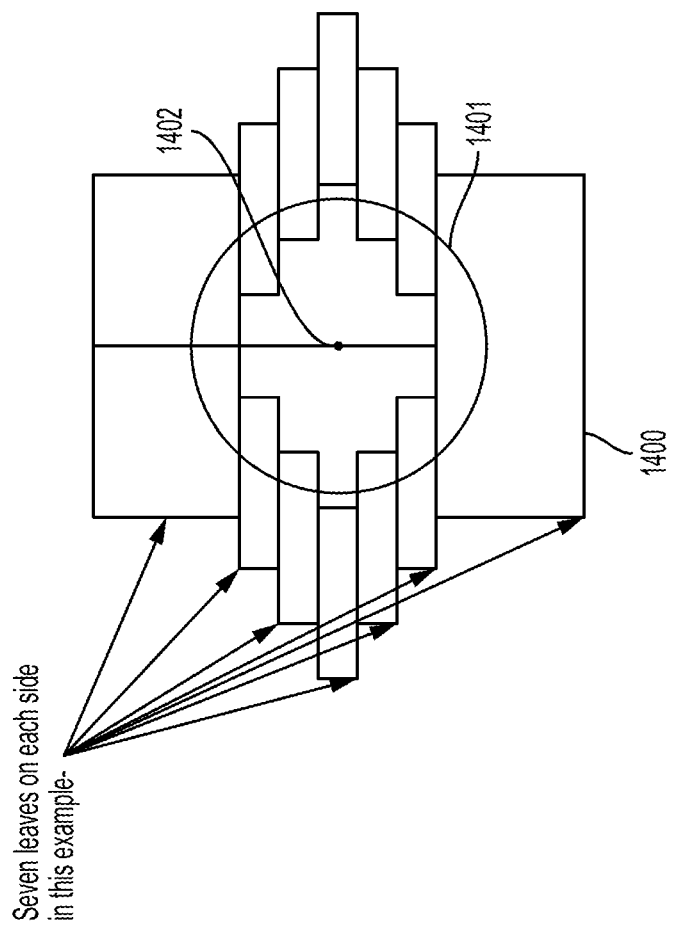
FIG. 30 is a top view of example adaptive aperture leaves positioned relative to a treatment area of an irradiation target.

FIG. 30 shows another example of leaves 1400 that are part of an adaptive aperture configured to trim a radiation spot 1401 centered at location 1402. In this example, there are seven leaves on each of two sides of the adaptive aperture (supported by corresponding carriages). The leaves on each side include two leaves that are wider than the other five; however, the adaptive aperture is not limited to this configuration. In this case, spot 1401 has a radius of 2.5 sigma defining an 8 mm Gaussian radiation spot.

Figure 4:
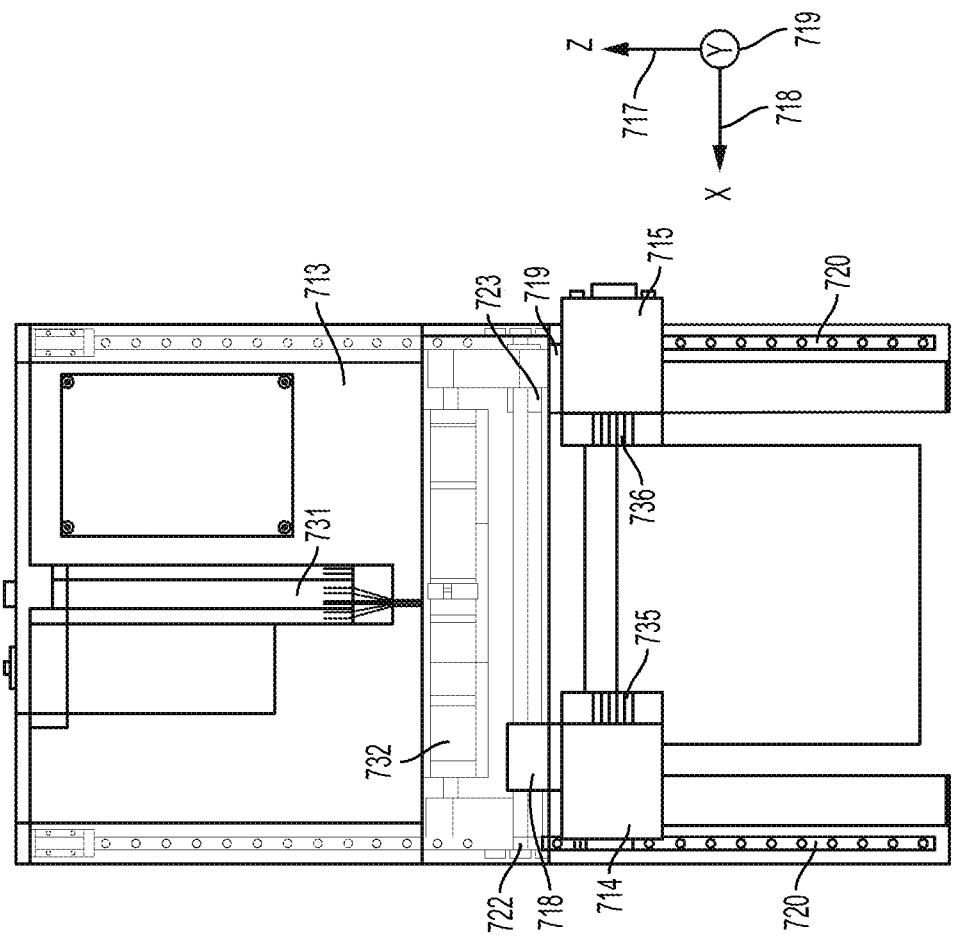
FIG. 4 is a front view of an example adaptive aperture having components portrayed in see-through to show the interiors thereof.
Figure 3:
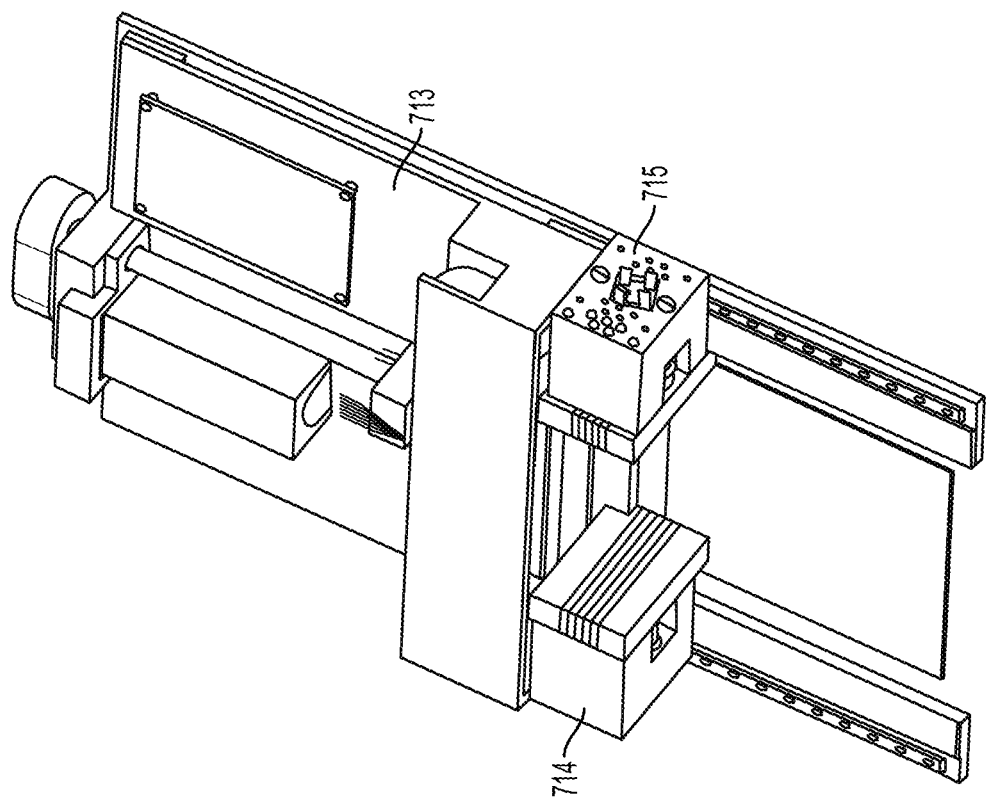
FIG. 3 is a perspective view of an example adaptive aperture.
Figure 5:
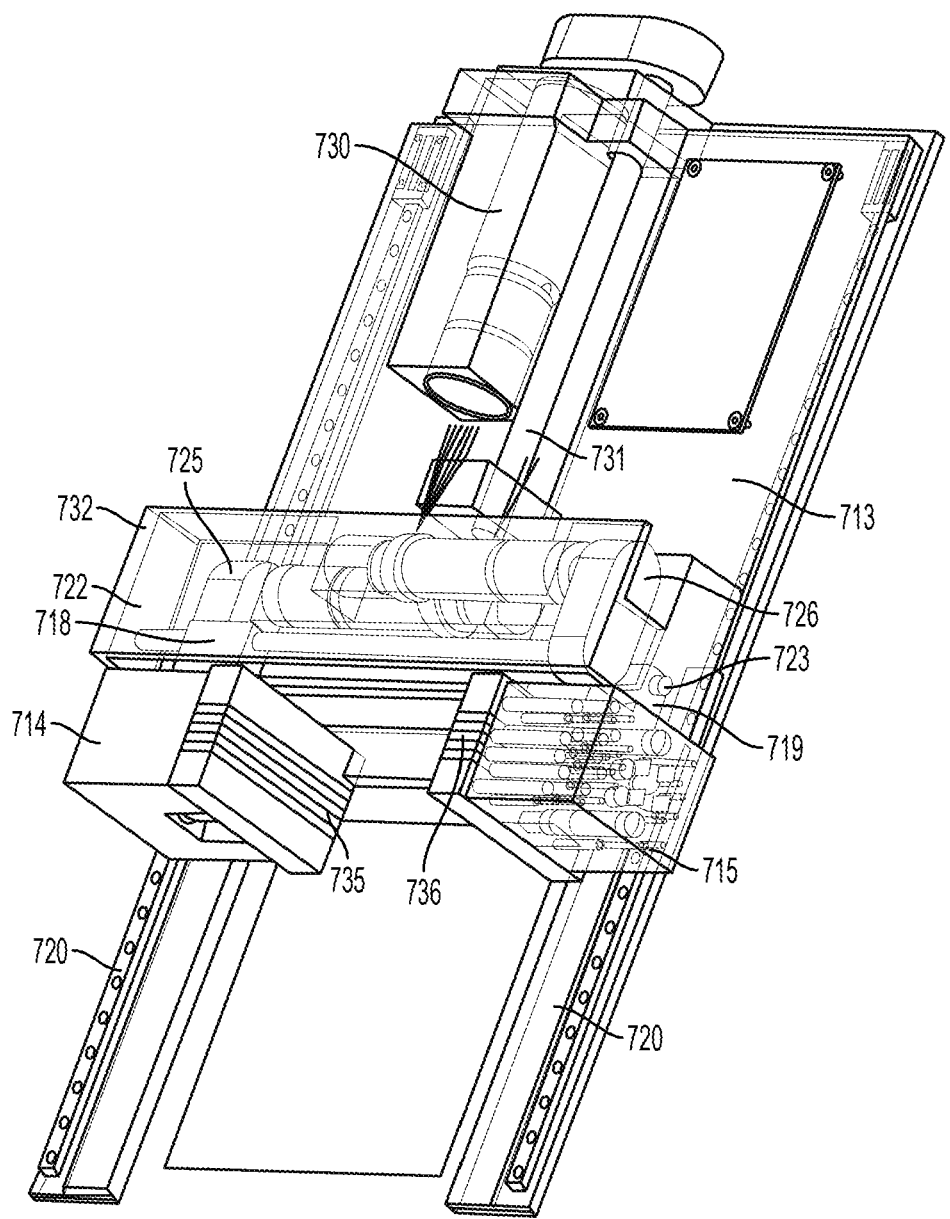
FIG. 5 is a perspective view of an example adaptive aperture having components portrayed in see-through to show the interiors thereof.

FIGS. 3, 4, and 5 show an example implementation of components of an example implementation of an adaptive aperture, including carriages 713, 714, 715 configured to hold, and to move, the leaves described above both vertically and horizontally relative to the treatment target. As shown, vertical movement includes movement in the Cartesian Z-dimension 717, and horizontal movement includes movement in the Cartesian X-dimension 718 (with the Cartesian Y-dimension being into, or out of, the page in FIG. 4). FIGS. 4 and 5 show parts of carriage housings as transparent in order to show components inside the housings; however, the housings are not actually transparent.

Carriage 713 is referred to herein as the primary carriage, and carriages 714 and 715 are referred to herein as secondary carriages. Secondary carriages 714, 715 are coupled to primary carriage 713, as shown in FIGS. 3 to 5. In this example, secondary carriages 714, 715 each include a housing that is fixed to primary carriage 715 via a corresponding member 718, 719. In this example, primary carriage 713 is movable vertically (the Z-dimension) along tracks 720. The vertical movement of primary carriage 713 also causes the secondary carriages to move vertically. In some implementations, the secondary carriages move vertically in concert. In some implementations, vertical movement of each secondary carriage is independent of vertical movement of the other secondary carriage.

As shown in FIGS. 3 to 5, each secondary carriage 714, 715 is connected to a corresponding rod 722, 723, along which the secondary carriage moves. More specifically, in this example, motor 725 drives secondary carriage 714 to move along rod 722 towards or away from secondary carriage 715. Likewise, in this example, motor 726 drives secondary carriage 715 to move along rod 723 towards or away from secondary carriage 714. Control over movement of the primary and secondary carriages is implemented to position the leaves relative to the irradiation target, as described herein. In addition, the leaves themselves are also configured to move in and out of the carriages, as also described herein.

As shown in FIG. 5, a motor 730 drives the vertical movement of primary carriage 713. For example, as shown in FIG. 4, lead screw 731 is coupled to housing 732, which holds motors 725, 726 that drive corresponding secondary carriages 714, 715, and which is mounted on tracks 720. Lead screw 731 is coupled to, and driven in the Z-dimension by, motor 730. That is, motor 730 drives lead screw 731 in the Z-dimension. Because lead screw 731 is fixed to housing 732, this movement also causes housing 732, and thus secondary carriages 714, 715, to move along tracks 720 in the Z-dimension.

In this example implementation, as noted, seven leaves 735, 736 are mounted on each secondary carriage 714, 715. Each secondary carriage may be configured to move its leaves horizontally (in the X-dimension) into, or out of, the treatment area. The individual leaves on each secondary carriage may be independently movable in the X-dimension relative to other leaves on the same secondary carriage. In some implementations, the leaves may also be configured to move in the Y-dimension. Furthermore, the leaves on one secondary carriage 714 may be movable independently of the leaves on the other secondary carriage 715. These independent movements of leaves on the secondary carriages, together with the Z-dimension movements enabled by the primary carriage, allow the leaves to be moved into various configurations. As a result, the leaves can conform, both horizontally and vertically, to treatment areas that are arbitrarily shaped both in horizontal and vertical dimensions. The sizes and shapes of the leaves may be varied to create different conformations.

The leaves may be made of any appropriate material that prevents or inhibits transmission of radiation. The type of radiation used may dictate what material(s) are used in the leaves. For example, if the radiation is X-ray, the leaves may be made of lead. In the examples described herein, the radiation is a proton or ion beam. Accordingly, different types of metals or other materials may be used for the leaves. For example, the leaves may be made of nickel, tungsten, lead, brass, steel, iron, or any appropriate combinations thereof. The height of each leaf may determine how well that leaf inhibits transmission of radiation.

In some implementations, the leaves may have the same height, whereas in other implementations, some of the leaves may have heights that are different from heights of others of the leaves. For example, in FIGS. 2 to 5, the leaves are each 5 mm in height. However, any appropriate heights may be used. For example, leaves 735, 736 may have any of the following (or other heights): 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, and so forth. The leaves may have any combination of the foregoing heights. In addition, each of the leaves may have a different height than one or more others of the leaves.

In some implementations, leaves of the same width or of varying widths may be stacked to inhibit radiation transmission. In some implementations, thinner leaves (e.g., leaves of lesser width) may be used in connection with thicker leaves (e.g., leaves of greater width). In some implementations, the leaves have enough height to completely block the particle beam at the maximum beam energy. Leaves of the same height or of varying heights may be stacked to inhibit radiation transmission. In some implementations, shorter leaves (e.g., leaves of lesser height) may be used in connection with longer leaves. In some implementations, the leaves have enough height to completely block the particle beam at the maximum beam energy. In some implementations, the leaves have enough height to block the particle beam at less than the maximum beam energy (and not to block the particle beam at maximum energy). For example, while a proton therapy system may have the capability to deliver a beam of energy 230 MeV that can treat to a depth in the patient of 32 cm, in some implementations, the adaptive aperture can only block protons of at most 175 MeV that can treat to a depth of no more than 20 cm. In doing so, less beam-stopping material may be used, e.g., 2.1 cm of Tungsten instead of 3.3 cm, or 3.3 cm of Nickel instead of 5.2 cm. In this example, the proton therapy system would still be capable of treating at depths exceeding 20 cm, but the adaptive aperture would not be used for such treatments. This may be deemed acceptable because, in some circumstances, deeper treatments benefit less from the particle beam collimation that the adaptive aperture provides. That is, in some treatment scenarios, shallow, low-energy treatments are where the adaptive aperture will be most effective, and there may be engineering advantages to reducing the amount of material in the leaves. Thus, in some example implementations, shorter leaves are used and the adaptive aperture is restricted to use with shallow, lower-than-maximum energy treatments.

In the implementations of FIGS. 2 to 5, the leaves are semi-rectangular in shape and have about the same surface area when viewed from the side. In some implementations, this need not be the case. For example, the leaves may have different shapes than those shown. Example shapes include, but are not limited to, circular shapes, curvilinear shapes, oval shapes, square shapes, and triangular shapes. Furthermore, individual leaves may have different shapes than others of the leaves contained in the same carriage or in a different carriage. For example, one carriage may contain both rectangular and curvilinear shaped leaves.

In some implementations, the leaves have heights that are enough not only to fully stop a particle beam at the maximum expected proton energy (e.g., 3.3 cm of Tungsten at 230 MeV or, e.g., 5.2 cm of nickel), but also to have enough extra material to prevent proton transmission between the leaves. This material may have a tongue and groove structure as shown in FIG. 1, or a similar configuration. The leaf ends may be configured to include curved or tapered surfaces to enhance delivered penumbra for proton beams of various divergence.

In some implementations, there may be more than one primary carriage and corresponding motors and rails. For example, a first primary carriage may control Z-dimension movement of a first secondary carriage, and a second primary carriage may control Z-dimension movement of a second secondary carriage. Therefore, in such implementations, the two secondary carriages can be moved independently in the Z-dimension, if desired. In any case, the primary carriage may be computer controlled. For example, executable instructions are stored in computer memory (e.g., one or more non-transitory machine-readable storage media), and executed by one or more processing devices to control the movement. Control may be performed with, or without, user input during treatment.

As explained, each secondary carriage 714, 715 includes a corresponding motor to control X carriage movement, as described above. In some implementations, there may be also one motor for each leaf, whereas in other implementations a single motor may control all leaves. The motors may be mounted on a corresponding secondary carriage. As a result, the motors move along with the corresponding secondary carriage. As noted, the motors control movement of leaves in each carriage. The leaves may be mounted on actuators that enable movement in two dimensions. In the examples of FIGS. 2 to 5, the leaves are each part of an integrated leaf. Referring to the example of FIG. 6, mechanisms enable the individual leaves to move in and out (the X-dimension) of the integrated leaf that comprises each carriage into, or out of, the treatment area.

Figure 6:
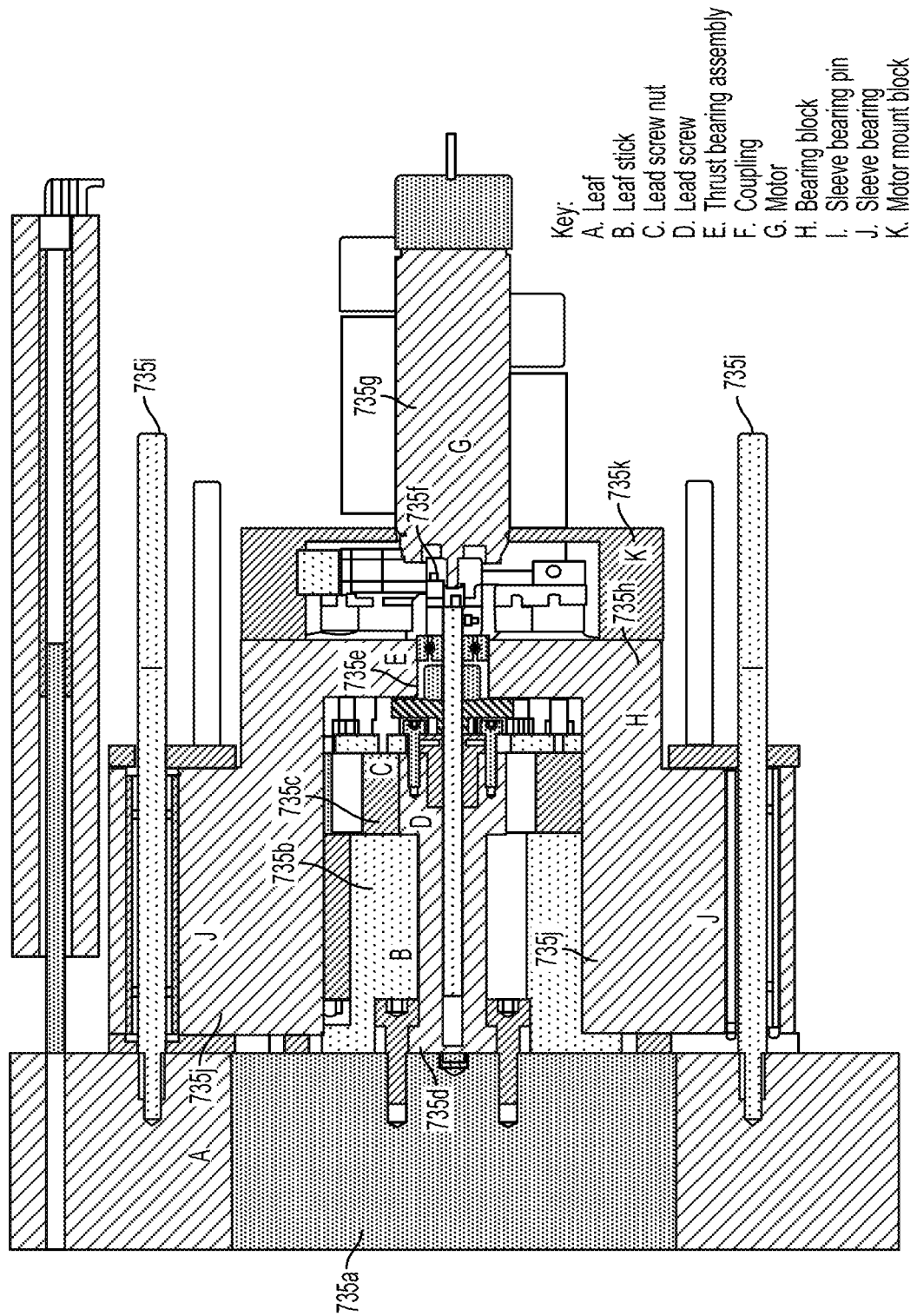
FIG. 6 is a top view of example control structures used to move a leaf into, and out of, a treatment area of an irradiation target.

In some implementations, all leaves on a single carriage are independently movable. FIG. 6 shows the movement mechanism for a leaf 735*a* that is part of a secondary carriage. Each leaf in each secondary carriage may have a configuration, and movement mechanism, that is similar to, or identical to, the leaf and movement mechanism of FIG. 6.

In the example of FIG. 6, the movement mechanism includes a leaf stick 735*b*, a lead screw nut 735*c*, a lead screw 735*d*, a thrust bearing assembly 735*e*, a coupling 735*f*, a motor 735*g*, a bearing block 735*h*, a sleeve bearing pin 735*i*, a sleeve bearing 735*j*, and a motor mount block 735*k*. In operation the motor shaft, through the coupling, spins the lead screw. This causes the lead screw nut to advance or retract depending on the direction of screw rotation. The lead screw nut is fixed to the leaf assembly so the leaf is moved forward or backward (into or out of the beam path) as the motor spins. Sleeve bearing pins are fixed to the leaf and slide along sleeve bearings which are held captive in the bearing block that supports the whole assembly. This bearing block houses the bearings and provides space for the motor assemblies for all leaves on the carriage.

In some implementations, the motors described with respect to FIG. 6 may be replaced with linear motors. In some implementations, the linear motors are controllable to configure a set of leaves to define a first edge, and to configure another set of leaves to define a second edge that faces the first edge. Each of the linear motors may include a movable component and a stationary component. The stationary component may include a magnetic field generator to generate a first magnetic field. An example of a magnetic field generator includes two stationary magnets that are adjacent and spaced apart, and that have their poles aligned. The movable component includes one or more coils to conduct current to produce a second magnetic field that interacts with the first magnetic field to cause the moveable component to move relative to the stationary component. For example, the movable component may be a coil-carrying plate between the two magnets that make up the stationary component. When current passes through the coil, that current produces a magnetic field that interacts with the magnetic field produced by the two magnets, and that causes the movable component (e.g., the current-carrying plate) to move relative to the two magnets. In some implementations, a single linear motor may control a single leaf. Because a leaf is attached to the movable component, the leaf moves along with the movable component. The linear motors of different leaves may be controlled to control movement of the leaves, and thus to define the edges of the adaptive aperture described herein.

As described, the adaptive aperture can be used to trim each layer of a scanned treatment with a different aperture shape, allowing for three-dimensional field shaping techniques such as layer stacking. However, an implementation of the adaptive aperture may be configured to mimic either a machined patient-specific structure or a multi-leaf collimator.

In this regard, some existing treatment planning systems (TPSs) perform treatment planning treatment planning processes that calculate the shape of a fixed brass aperture meant to be uniformly applied to the entire treatment volume. TPSs may also dictate, or contain instructions to configure, an adaptive aperture shape for a target. A computer program can interpret an aperture shape, either from a continuous aperture curve or set of fixed multi-leaf collimator leaf positions, and translate that shape into a series of dynamic leaf positions for the adaptive aperture that correlate with delivered radiation treatment spots. Existing TPS functionality can thus be leveraged, allowing the adaptive aperture to be compatible, with relatively few modifications, to existing TPS software.

Another example technique that may improve edge conformality and that is enabled by the adaptive aperture takes advantage of the possibility that a treatment dose to the same treatment area of a layer will be delivered in several passes or paintings. Repainting, which is described herein, is a technique used in scanned proton therapy in which dose is divided to a treatment area using several particle beam passes in order to spread the delivered radiation uniformly during a timescale that is long compared with patient motion, such as breathing. There are also other reasons in which dose to a given spot may not all be delivered in one pulse. Some example reasons include: dynamic dose control can regulate the charge in each pulse to deliver an accurate total dose, there are safety limits to the charge in a pulse, and a required dynamic range of dose may exceed the capabilities of the particle accelerator.

If the spots in an irradiated volume will be painted several times during a treatment (e.g., during multiple scans), then the conformality of the adaptive aperture to the lateral edge of the irradiation target can be improved by shifting the leaves slightly (e.g., at the sub-millimeter level), vertically, horizontally, or both vertically and horizontally between each painting (e.g., between each scan pass of the particle beam covering a same treatment area). In this way, what might have been a slightly jagged edge owing to the finite size of the individual leaves can be smoothed to attain a better approximation of the intended aperture curve.

Adding rotational degrees of freedom can improve the ability of the adaptive aperture to conform to radiation targets. For example, the entirety of the assembly of FIGS. 3 to 5 may be configured to be rotated in a plane perpendicular to the beam direction, in a plane parallel to the beam direction, or in a combination thereof. In some implementations, each individual secondary carriage 714, 715 may be configured to rotate independently in a same plane. In this way, the adaptive aperture may provide more flexibility to conform to complex shapes that are not ideally oriented. In some implementations, both the primary carriage and each secondary carriage may be rotatable.

In the example implementations described above, each leaf is independently actuated such that an arbitrary shape can be traced with a leaf configuration. It may be, however, that such flexibility is not required to achieve acceptable edge conformality. The leaves could be mechanically constrained with the ability to achieve only a finite number of configurations. For example, the leaves could be restricted to arrangements that put them in a vertical line, forward diagonal shape, backward diagonal shape, concave shape, convex shape, or any other achievable shape. In this way, flexibility could be traded for mechanical simplicity. The leaves may be actuated using a cam timing gear through one remote motor rather than four motors mounted on a secondary carriage. In some implementations, discrete shapes of the gears may be machined out of sectors of wheels which are rotated into place as needed. In order to reduce the number of motors, feedback, controllers, and associated wiring, an assembly may be used that has one motor that achieves discrete leaf configurations.

Figure 7:
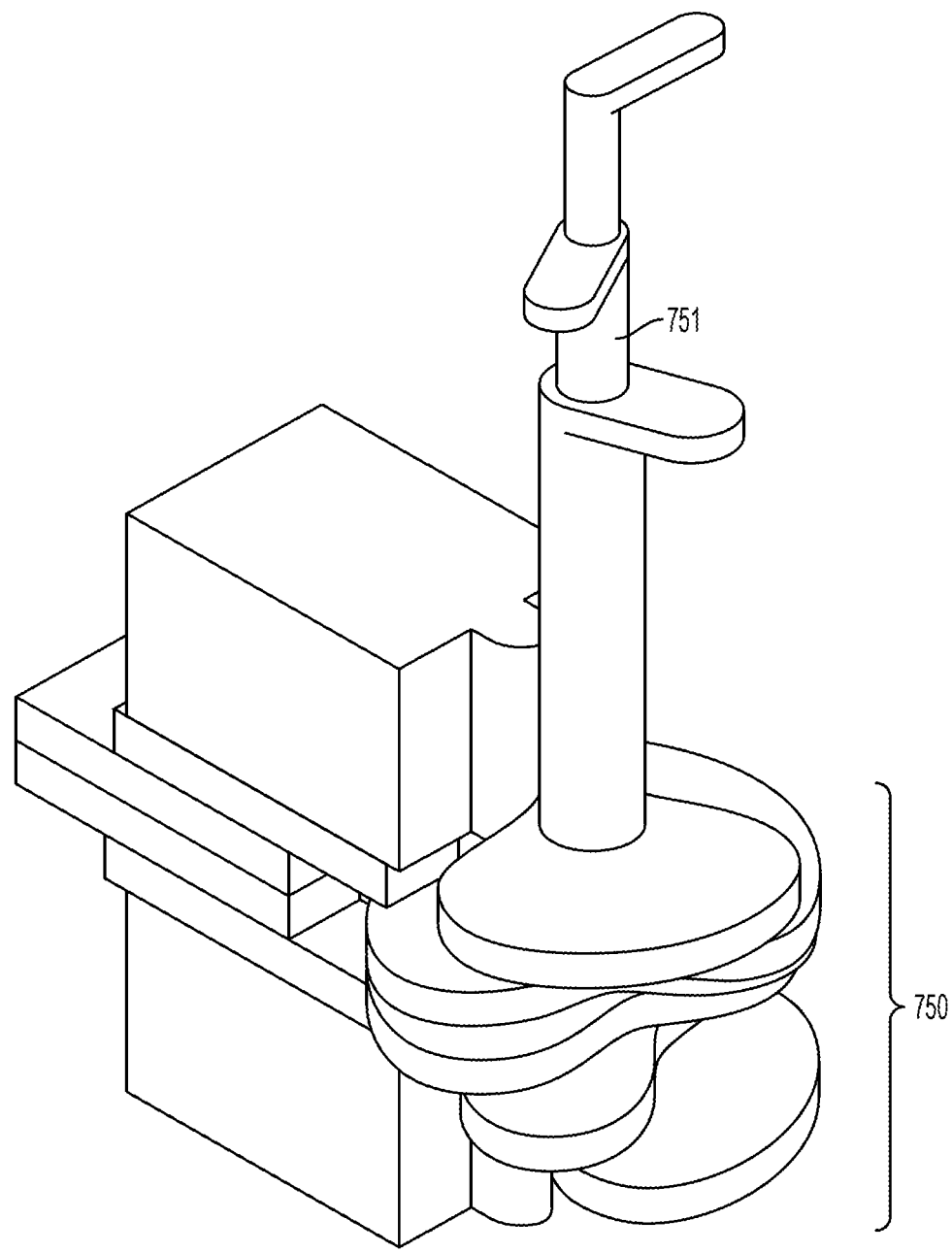
FIG. 7 is a perspective view of an example adaptive aperture having curved leaves.

FIG. 7 shows an example implementation of an adaptive aperture having cams that are rotatable relative to shaft 751. In the example of FIG. 7, all leaves 750 are actuated by one motor. This motor is at the top of vertical shaft 751. The shape and orientations of leaf cams are chosen to achieve different leaf configurations for different rotational angles of the main drive shaft.

Another possible advantage of the adaptive aperture is the ability to collimate edges that are completely internal to the field. If a treatment plan calls for a volume to be treated that completely surrounds a volume to be protected—for example, a tumor that completely surrounds a spinal cord—a single, machined structure will typically be unable to block radiation to the protected volume without blocking some of treated volume as well. The adaptive aperture can treat such a field using a sequence of leaf positions. For example, the adaptive aperture can be reconfigured dynamically, and during treatment, to protect the areas that require protection, while allowing treatment on areas that require treatment.

In some cases, better beam performance (penumbra or edge sharpness) results when the particle beam is tangent to the surface of a leaf edge. However, since the beam effectively originates from a single point source, the angle with which it passes through the plane of the adaptive aperture changes as the beam is moved away from the center of the field. For this reason, leaves may have curved edges, as shown in FIG. 1, so that the edges can always be placed a location that makes them tangent to the particle beam. In an example implementation of the adaptive aperture, the tracks on which both primary and secondary carriages move are curved so that flat leaf edges can be used in lieu of curved leaf edges, and so that the flat but remain tangent to the particle beam.

Figure 29:
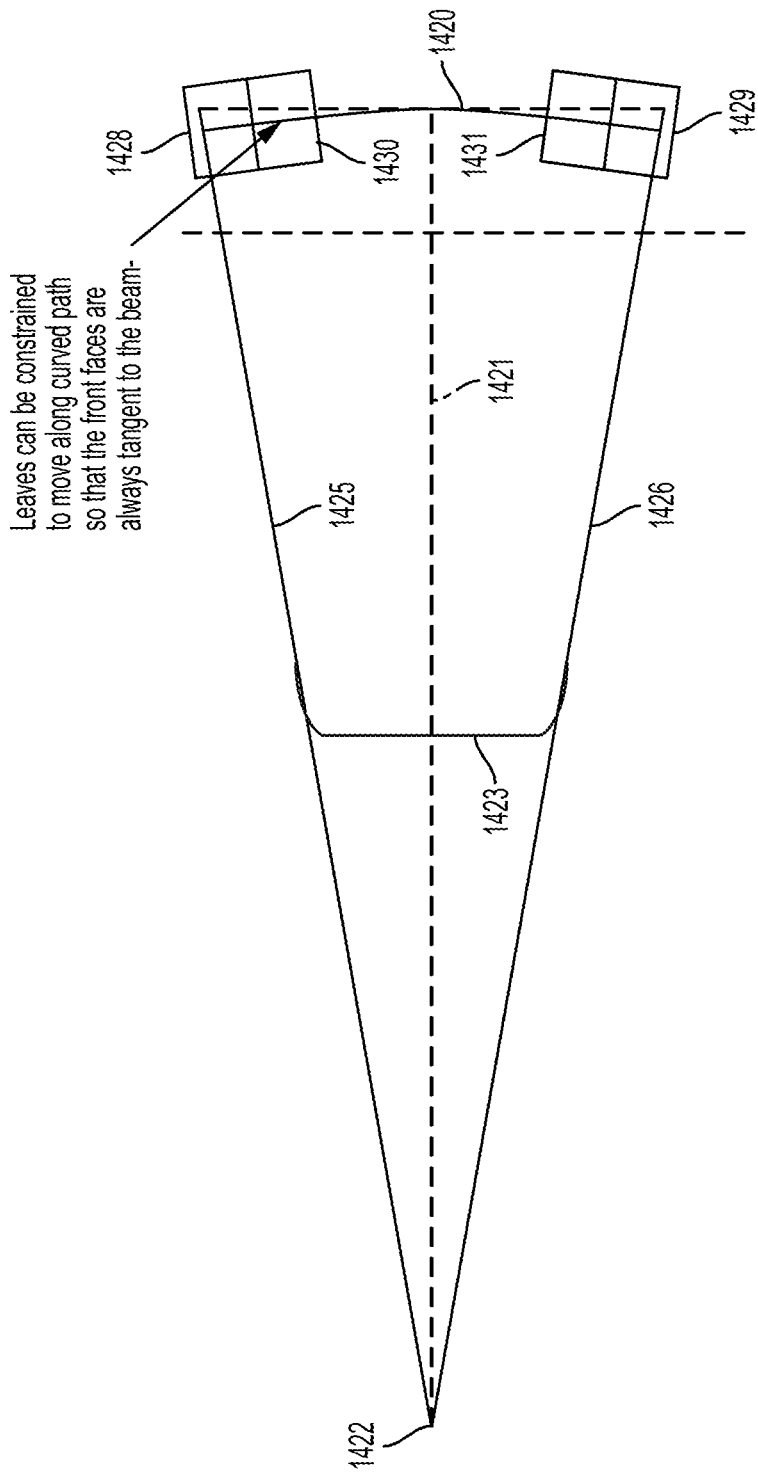
FIG. 29 is a top view of example adaptive aperture leaves on carriages mounted on a track that is curved relative to the direction of a particle beam.

FIG. 29 shows an example implementation of a curved track 1420. In the example of FIG. 29, the particle beam 1421 originates from source 1422, which may be a particle accelerator like the synchrocyclotron described herein. Particle beam 1422 may scan through field 1423 and, at one extent, may be at location 1425 and, at another extent, may be at location 1426. Carriages holding leaves 1428 and 1429 are mounted on curved track 1420 so that leaves 1428 and 1428 can move towards or away from each other. In this example, the leaves have straight ends (or "fronts") 1431, 1431 in contrast to curved end 56 of FIG. 1. By employing a curved track, the particle beam can remain tangent, or substantially tangent, to the straight ends throughout the scan field 1423. Keeping the particle beam tangent to the ends can be advantageous in that it enables the trimming provided by the adaptive aperture to be consistent throughout the range of the beam field.

To summarize, in some implementations, the adaptive aperture may trim only a small fraction of a treatment area at one time, e.g., an area that is less than the entire treatment area and that is about equal to one spot size, two spot sizes, three spots sizes, four spot sizes, five spot sizes, and so forth. Thus, in some implementations, the adaptive aperture may be small enough to trim a single spot at once and may be large enough to trim several spots in one position, but not the entire field without moving. The adaptive aperture may be configured to move around and within the field as the beam scans. For example, in some implementations, the adaptive aperture tracks the beam as it scans, and its configuration and reconfiguration may be synchronized to the scanning and to the pulses provided by the beam (e.g., different reconfigurations for different beam pulses and/or locations). By not using leaves large enough to trim an entire treatment area, the adaptive aperture can be made smaller and therefore the adaptive aperture can be placed closer to the patient with little or no interference from other devices. In some implementations, no leaf of the adaptive aperture even has one dimension that spans an entire maximum treatment area. In some implementations, each individual leaf is movable in two dimensions within the treatment area, and the device is mounted on a gantry (e.g., in the context of a particle therapy system such as that described herein) to be rotated on one or more axes and made extendable towards and away from isocenter.

Example treatment planning processes are described in the context of a system, such as that described herein, that contains an adaptive aperture. The example treatment planning processes described below, however, are not limited to use with the systems described herein, and may be used with any appropriate system that applies radiation to a target, such as a tumor, for treatment.

An example treatment planning process (TPP) performed by a TPS may employ inverse planning. Generally, inverse planning includes obtaining a target dose distribution of radiation, and then performing a process, such as an optimization process, to determine characteristics that together achieve the target dose distribution. The process may be performed by executing, on one or more processing devices, one or more computer programs that are stored on, and retrieved from, one or more non-transitory machine-readable storage media. The characteristics may include, but are not limited to, spot size, spot shape, spot location, spot weight (the number of protons per spot), spot orientation, and so forth. In some implementations, the characteristics may include information relating to the construction of the adaptive aperture, e.g., the numbers and locations of its leaves, the spot resolution that can be achieved using the adaptive aperture, the ways and extents that the carriages can be moved, and so forth. In such examples, the TPS leverages its knowledge of the structure of the adaptive aperture to produce instructions to the adaptive aperture to control its configuration.

Figure 31:
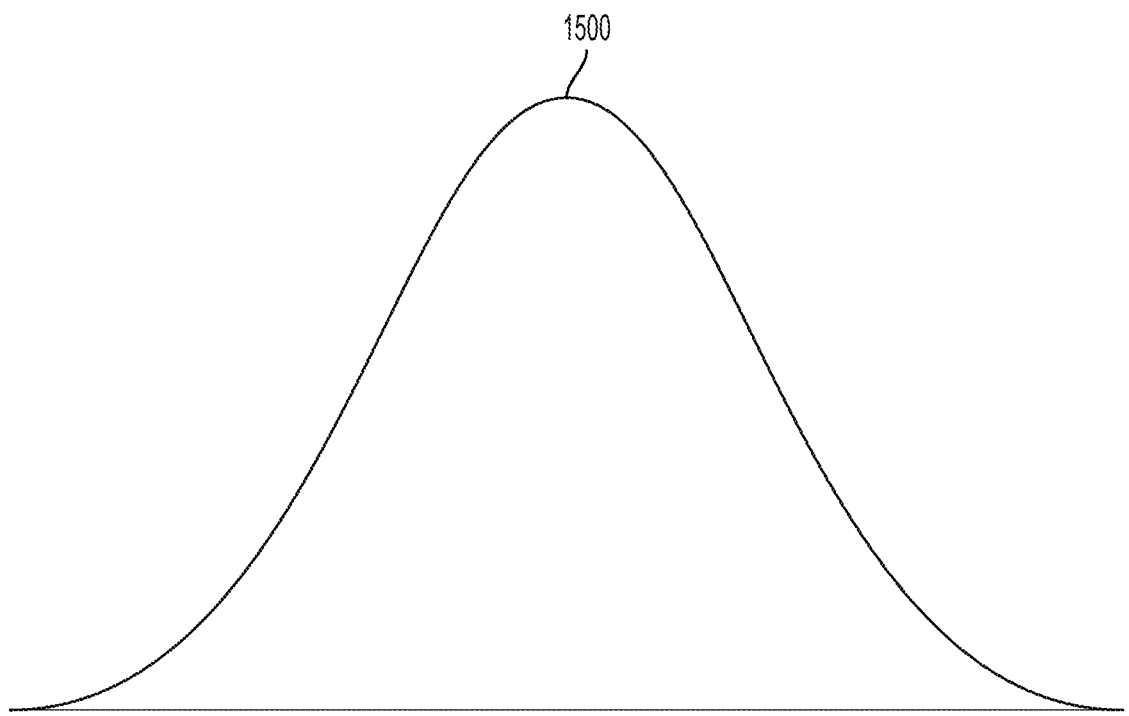
FIG. 31 is a graph showing an Gaussian distribution of a spot produced by the example particle therapy system.

As described herein, the example adaptive apertures of FIGS. 1 to 7, 29, and 30 may be used to trim a single spot, a set of spots, a treatment layer, or a treatment field. A treatment field includes the extent of radiation that can be applied at a particular layer, and may extend beyond the layer itself. An example spot may have a Gaussian distribution, as shown in the graph of FIG. 31. That is, the distribution of protons in the spot is Gaussian in that the center 1500 of the spot has the highest concentration of protons and that concentration decreases as the distance from the center of the spot decreases. This Gaussian distribution can have an effect on treatment planning. For example, in some implementations, a TPP may take this distribution into account in determining the appropriate dose for a given location of a radiation target, and also may take this distribution into account in determining whether, and where, to trim the spot using the adaptive aperture (or any other appropriate spot-trimming mechanism). For example, referring to FIG. 2, the adaptive aperture may be used to trim spots at the border between a radiation target defined by circle 708 (e.g., a tumor) and healthy tissue. However, trimming is not limited to the border between diseased and healthy tissue. For example, a treatment plan may require that spots interior to a treatment layer be trimmed, e.g., in order to achieve a desired dose distribution. Accordingly, the adaptive aperture may be configured to implement interior spot trimming as well.

Figure 32:
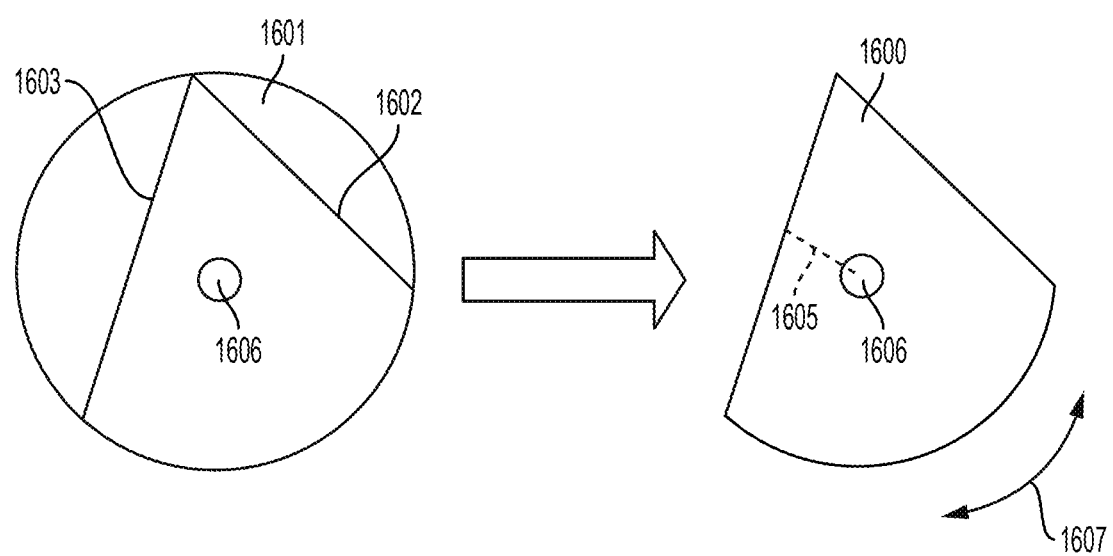
FIG. 32 depicts an original spot and a pre-trimmed spot produced by trimming the original spot.

An example TPP is executed by a TPS. An example TPP references a library containing information defining characteristics of pre-trimmed spots that the process may use to achieve a target dose distribution. For example, the library may define a trimmed spot based on one or more parameters. For example, referring to FIG. 32, a pre-trimmed spot 1600 (shown in top view) may be defined in terms of its radius and angle of rotation. In the example of FIG. 32, pre-trimmed spot 1600 is created by trimming original spot 1601 at chords 1602 and 1603. In pre-trimmed spot 1600, the radius is the line 1605 from the center 1606 of the non-trimmed spot that is perpendicular to the spot edge. In the example of FIG. 32, the angle of rotation is defined as the amount that the spot has been rotated 1607, either clockwise or counterclockwise, relative to its original position. In some examples, such as spot 1600 of FIG. 32 multiple radii (in this case two) may define the spot. In some implementations, a single radius may define the spot, in part. And, in other implementations, more than two radii may define a spot, in part. The library may store information defining characteristics of any appropriate number of pre-trimmed spots, which may be used to generate actual spots.

A pre-trimmed spot may have any appropriate shape, and is not limited to the shapes shown in FIG. 32. For example, a pre-trimmed spot may have one or more step-like edges, like the spots trimmed in FIGS. 2 and 30.

In some implementations, additional, or other, information may be used to define spots in the library. For example, area, shape, or other descriptive information may define each spot. This information may be in addition to, or instead of, the radius and rotation indicated above The information that defines each spot, e.g., a radius and rotation, is stored in computer memory, e.g., in one or more files, look-up tables, or other constructs, that enable the information to be indexed to corresponding leaf movements of the adaptive aperture.

More specifically, in some implementations, each trimmed spot may be created from a radiation spot (e.g., one generated by the synchrocyclotron described herein) that has been trimmed. As described herein, the trimming may be performed using the adaptive aperture. The configuration of the adaptive aperture used to create each trimmed spot may be indexed to, or otherwise stored in association with, the information in the library that defines the spot. The configuration may include, but is not limited to, the leaf configuration of the adaptive aperture (e.g., which leaves are extended and which are not), the rotational angle of the adaptive aperture, the position(s) of the primary and secondary carriage(s), and so forth. Any appropriate information that characterizes the configuration of the adaptive aperture to produce the corresponding trimmed spot may be stored.

In some implementations, during treatment planning, the TPP performs a process, such as an optimization process, in which the TPP selects information for pre-trimmed spots from the library in order to achieve the target dose distribution for the treatment. For example, the TPP may use that information to simulate dose distributions for trimmed spots iteratively until the target dose distribution, or a dose distribution acceptably close to the target dose distribution, is achieved. The information that produces the best dose distribution is received by a computing system that controls the adaptive aperture, and that information is translated into leaf and/or carriage positions. In some implementations, the TPP may employ a Monte Carlo optimization process in order to achieve the desired dose distribution. Generally, a Monte Carlo optimization process includes defining a domain of possible inputs (e.g., information defining trimmed spots from the library), generating inputs randomly from a probability distribution over the domain, performing a deterministic computation on the inputs, and aggregating the results. In some implementations, the TPP may employ a Pencil Beam-based optimization process, or any other appropriate optimization process in order to achieve the desired dose distribution.

In some implementations, during treatment planning, the TPP performs a process, such as an optimization process, in which the TPP optimizes trimming curves in order to achieve a target dose distribution for the treatment. For example, the TPP may obtain information defining trimming curves to be produced using the adaptive aperture, and use that information to simulate dose distributions for trimmed spots iteratively until the target dose distribution, or a dose distribution acceptably close to the target dose distribution, is achieved. The information defining the trimming curves may include, e.g., lengths, curvatures, angles, orientations, and any other appropriate information that can define a trimming curve. In this example, the information is independent of the pre-trimmed spots in the library, and the pre-trimmed spots are not used to control the adaptive aperture. Rather, the information that produces the best dose distribution is received by a computing system that controls the adaptive aperture, and that information is translated into leaf and/or carriage positions. As above, in some implementations, the TPP may employ a Monte Carlo optimization process, a Pencil Beam-based optimization process, or any other appropriate optimization process in order to achieve the desired dose distribution.

In some implementations, during treatment planning, the TPP performs a process, such as an optimization process, in which the TPP defines different spot sizes and/or shapes to be produced through trimming based on information such as, but not limited to, spot radius and orientation. For example, the TPP may use that information to simulate dose distributions for trimmed spots iteratively until the target dose distribution, or a dose distribution acceptably close to the target dose distribution, is achieved. Information identifying the sizes and shapes may include information identifying a spot radius and/or orientation as described herein, or any other appropriate identifying information. In this example, the information is independent of the pre-trimmed spots in the library, and the pre-trimmed spots are not used to control the adaptive aperture. Rather, the information that produces the best dose distribution is received by a computing system that controls the adaptive aperture, and that information is translated into leaf and/or carriage positions. As above, in some implementations, the TPP may employ a Monte Carlo optimization process, a Pencil Beam-based optimization process, or any other appropriate optimization process in order to achieve the desired dose distribution.

In some implementations, during treatment planning, the TPP performs a process, such as an optimization process, in which the TPP defines leaf and/or carriage movements of the adaptive aperture to perform treatment. That is, the TPP knows the geometry, structures, and capabilities of the adaptive aperture, and leverages this knowledge to optimize the treatment plan. For example, the TPP may use that information to simulate dose distributions for trimmed spots iteratively until the target dose distribution, or a dose distribution acceptably close to the target dose distribution, is achieved. The leaf and/or carriage positions that are closest to the target dose distribution are provided, by the TPP, to a control/computing system that controls configuration of the adaptive aperture. In this example, the information identifying leaf and/or carriage movements is independent of the pre-trimmed spots in the library, and the pre-trimmed spots are not used to control the adaptive aperture. Rather, the information is received by the control/computing system that controls the adaptive aperture, and that information is used to position the leave(s) and/or carriage(s) of the adaptive aperture. As above, in some implementations, the TPP may employ a Monte Carlo optimization process, a Pencil Beam-based optimization process, or any other appropriate optimization process in order to achieve the desired dose distribution.

In general, after the TPP determines the appropriate dose distribution, including information to control the adaptive aperture, the TPP provides that information to a control system (e.g., one or more computers) for the particle therapy (or other radiation therapy) system. In some implementations, the information provided from the TPP identifies the spots in the library that are to be used to implement the dose distribution, and indicates where those spots are to be formed on/applied to the irradiation target at the time of delivery of each spot. In some implementations, the information provided from the TPP identifies the spot sizes and shapes that are to be used to implement the dose distribution, and indicates where those spots are to be formed on/applied to the irradiation target at the time of delivery of each spot. Information identifying the sizes and shapes may include information identifying a spot radius and/or orientation as described herein, or any other appropriate identifying information. In some implementations, the information provided from the TPP identifies trimming curves to be produced by the adaptive aperture. In some implementations, the information provided from the TPP includes leaf and/or carriage positions that are specified for the adaptive aperture.

The control system uses the information received from the TPP to determine the configuration of the adaptive aperture needed to obtain the target dose distribution or a dose distribution that is acceptably close to the target dose distribution. In an example, information that characterizes the configuration of the adaptive aperture needed to create a trimmed spot may be associated with (e.g., indexed to) information defining the corresponding pre-trimmed spot (e.g., its radius and orientation). The control system obtains the information characterizing the configuration of the adaptive aperture, and uses that information, together with the information indicating where the spots are to be applied at the time of delivery of each spot, to control operation of the particle accelerator and the adaptive aperture. That is, the information indicating where the spots are to be applied at the time of delivery of each spot is used to control beam output and direction; and the information characterizing the configuration of the adaptive aperture is used to configure the adaptive aperture at appropriate times in order to achieve the target dose distribution. In an example, information that characterizes the configuration of the adaptive aperture needed to create a trimming curve may be derived from a shape of that curve received from the TPP. In an example, information that characterizes the configuration of the adaptive aperture may be received directly from the TPP in the form of leaf and/or carriage positions.

In operation, for each trimmed spot, the adaptive aperture is configured to achieve the appropriate spot size and shape. For example, the leaves of the adaptive aperture are extended or retracted, as appropriate, to produce a trimmed spot that is identical to, or approximates, a spot for a particular location. In some implementations, locations of the adaptive aperture leaves, and therefore movements thereof, are determined relative to a predefined isocenter of the irradiation target. Movements of the leaves are commanded by the control system in accordance with the required configuration for each spot. Movements of the primary and/or secondary carriages may also be commanded, as appropriate, in addition to, or instead of, movements of the leaves. As explained, in some implementations, the size and shape of each spot may vary spot-by-spot (e.g., on a spot-by-spot basis), requiring reconfiguration of the adaptive aperture in between spot scans. In some implementations, the configuration of the adaptive aperture is maintained between spot scans, thereby reducing the need for reconfiguration each time the beam is moved. In some implementations, e.g., at the interior of a layer of an irradiation target, trimming is not performed, e.g., all of the leaves of the adaptive aperture may be retracted. In some implementations, including at the interior of a layer of the irradiation target, trimming is performed, e.g., to define one or more spot edges to achieve the target dose distribution.

As described herein, treatment may be performed on the irradiation target layer-by-layer. Layers may be accessed by varying the energy of the particle beam, with higher-energy beams penetrating to reach deeper layers (relative to the beam source). As described herein, the energy of the particle beam may be changed by moving one or more plates into the particle beam path, by changing the energy of the beam using a variable-energy accelerator, or by a combination thereof.

Figure 33:
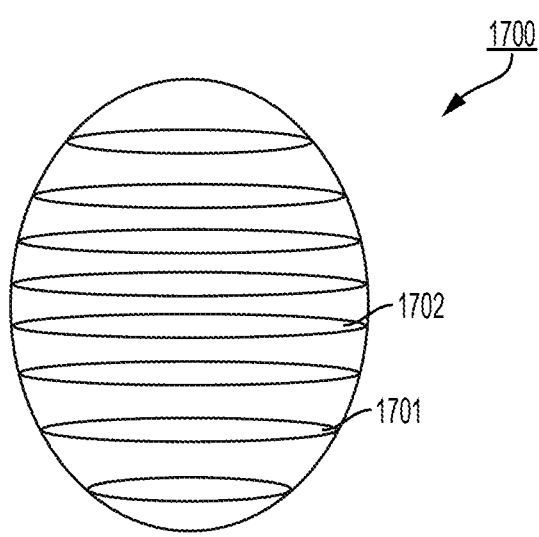
FIG. 33 is a perspective view of an irradiation target containing layers to be treated by particle therapy.

In some implementations, the adaptive aperture may trim a single spot, part of a layer to be treated, the entire layer to be treated, or the entire radiation field for that layer. That is, the adaptive aperture may be used to trim more than an individual spot or set of spots within a field or layer. For example, the adaptive aperture may be configured differently, for each layer or field for that layer. In this regard, FIG. 33 shows a side view of an irradiation target 1700 having several layers to be treated, including layers 1701 and 1702. Referring also to FIGS. 1 to 7, the adaptive aperture may be configured to trim layer 1702; and the adaptive aperture may be configured to trim the layer 1701. In each case, appropriate leaves may be extended or retracted, and one or more carriages may be moved to appropriate locations, in order to change the configuration of the adaptive aperture to a configuration that is appropriate for the layer. The TPP may perform appropriate optimizations to define the trimming to be performed for each layer.

Figure 34:
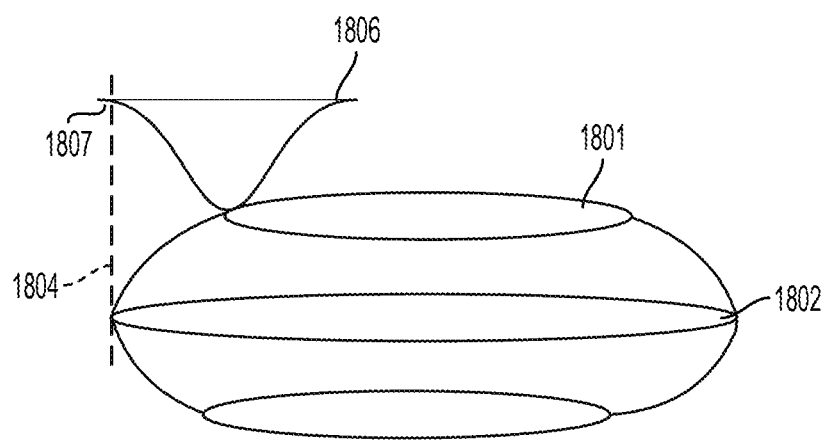
FIG. 34 is a perspective view of an irradiation target containing layers to be treated, and application of a trimming curve to the irradiation target.

In some implementations, the adaptive aperture may trim a curve that has been generated by the TPP for all layers of an irradiation target. More specifically, in some implementations, an optimized treatment plan may not require different trimming for different layers (e.g., depths) of an irradiation target. That is, a single trimming curve (an aperture may be a trimming curve) may be configured and used for all layers of the irradiation target, even if those layers have different cross-sectional shapes. For example, in FIG. 34, layers 1801 and 1802 have different widths. The TPP may generate an optimized trimming curve that is capable of trimming both layers. For example, as shown in FIG. 34, a trimming curve 1804 may trim at edges of wider layers (e.g., 1802) of the irradiation target, and only trim the tail edge 1807 of a Gaussian spot 1806 (depicted as an inverted Gaussian curve) produced at more narrow layers (e.g., 1801). The TPP may generate the optimized trimming curve by dividing the irradiation target into voxels of a predefined shape and volume, and by iteratively adjusting parameters for the voxels until an optimized trimming curve is determined. For example, for each voxel, the TPP selects parameters such as spot weight, location, size, shape, etc., and iterates through those parameters until the target dose distribution is obtained across the irradiation target, or until a dose distribution within a specified tolerance of the target dose distribution is obtained across the irradiation target. After that optimized dose distribution is determined, the TPP may determine a trimming curve that best fits each layer of the irradiation target based on the determined dose distribution.

More specifically, in an example, the TPP examines the determined dose distribution for each layer and, based on those dose distributions, selects a single trimming curve that is most appropriate for all layers. For example, in some implementations, the trimming curve may be configured to accommodate the irregular patterns of different layers of the irradiation target. Selection of the size and shape of the trimming curve may also be based on structures inside the irradiation target or external to the irradiation target. For example, different exterior structures may be more tolerant of exposure to radiation than others. The trimming curve may be configured to accommodate such tolerances.

As described, in some implementations, the TPP provides, to the control system, specifications of the trimming curve of FIG. 34. The specifications may include, e.g., the shape and location of the trimming curve relative to a known point, such as an isocenter in the irradiation target. In an example, the control system configures the adaptive aperture to produce a trimming curve that meets the specifications provided by the TPP. In this example, the adaptive aperture is not reconfigured to treat successive layers, and thus mimics a preconfigured (and not adaptive/reconfigurable) aperture or other appropriate structure.

In the foregoing example, the same trimming curve is used for each layer to be treated. This can be advantageous since it allows the adaptive aperture to be used with legacy TPPs. More specifically, some legacy TPPs are configured for operation with a predefined aperture, where a conventional aperture is a static (e.g., non-adaptive) structure or structures that create a hole through which radiation passes unimpeded. By configuring the adaptive aperture so that it maintains the same configuration throughout treatment, the adaptive aperture can be used with legacy TPPs of the type described above.

In the example implementations described above, the TPP selects parameters such as spot weight, location, size, shape, etc., and iterates through those parameters until the target dose distribution is obtained across the irradiation target. In some example implementations, the TPP does not have knowledge of, or take into account, the configuration of the adaptive aperture when obtaining the target dose distribution. Rather, the specifications provided by the TPP are interpreted by the control system to control the configuration of the adaptive aperture, e.g., to extend or retract leaves, move carriage(s), etc. in order to achieve an appropriate trimming curve based on the dose distribution.

As described, in some implementations, the TPP has knowledge of, and takes into account, the configuration of the adaptive aperture when obtaining a target dose distribution. For example, the TPP may know the number of leaves in the adaptive aperture, the dimensions and shape of each leaf, the relative locations of the leaves, the number of carriages, how the carriages move, and so forth. This information may be taken into account, along with, e.g., the spot weight, spot location, spot size, spot orientation, and/or spot shape, when determining an optimized dose distribution for the irradiation target. The TPP may use this information in determining appropriate leaf positions corresponding to each delivered spot. That is, the TPP has knowledge of the true geometry and motion constraints of the adaptive aperture leaves and includes that geometry directly in its optimization calculations. The TPP then produces a prescription for the exact positions of the leaves and/or carriages for every spot. Thus, in this example, the specifications provided by the TPP to the control system include information used to configure the adaptive aperture. For example, the specifications may include a configuration of leaves and/or carriages of the adaptive aperture. In some implementations, a different set of configurations of the adaptive aperture, as appropriate, may be provided for each layer of, or spot on, the irradiation target. In this example, information about the trimming curve itself need not be provided by the TPP, since the configuration information for the adaptive aperture (including, e.g., the leaf configuration information) provided by the TPP defines the trimming to be produced.

In an example implementation, the TPP performs an optimization process, such as the Monte Carlo optimization or the Pencil Beam optimization, using information defining different spot shapes (e.g., obtained from the library or elsewhere) and using known adaptive aperture (e.g., leaf) configurations. In an example optimization process, for a known particle beam, the TPP may iterate through different combinations of beam shape and adaptive aperture configurations to obtain a resulting dosage, and compare the resulting dosage to a target dosage (for the area under consideration). If the resulting dosage deviates from the target dosage by more than a defined amount, a different combination of spot shape and adaptive aperture configuration is selected, and the process is repeated until an optimization is achieved (e.g., the resulting dosage matches the target dosage for the area or is within the defined tolerance relative to the target dosage).

In some implementations, a TPP selects beam spot shapes based on the dose and dose restrictions of an inverse planning process. In some implementations, the selection of spot shapes and sizes may be based on spots defined in the library described herein that contains information defining characteristics of pre-trimmed spots. In some implementations, the selection of spot shapes and sizes may be independent of spots defined in the library described herein that contains information defining characteristics of pre-trimmed spots. For example, TPP may configure the adaptive aperture—including leaves and/or carriages—to produce spots having any appropriate shapes. In other words, the TPP may be programmed with the capabilities of the particle therapy system, and also be programmed with a treatment plan for an irradiation target, such as a tumor. Given this information, the TPP may instruct the adaptive aperture to produce spot shapes and sizes by trimming the particle beam in any appropriate manner to achieve the desired treatment. The trimming that is produced by the adaptive aperture is not limited to producing predefined spots from the library in this example.

In some implementations, a TPP selects beam spot shapes based on the dose and dose restrictions of an inverse planning process. A radiation plan that describes the positioning and shape of multiple treatment spots may be developed with reference to a dose map prepared by a physician using planning software to convert the dose map to a radiation plan. The dose map may be prepared, for example, using a graphics terminal with the physician viewing one or more CT images of the patient to define target (e.g., desired) doses in different zones within the volume of the patient. An optimization process may be performed to determine which spots to apply to the treatment area to achieve the target dose.

Figure 37:
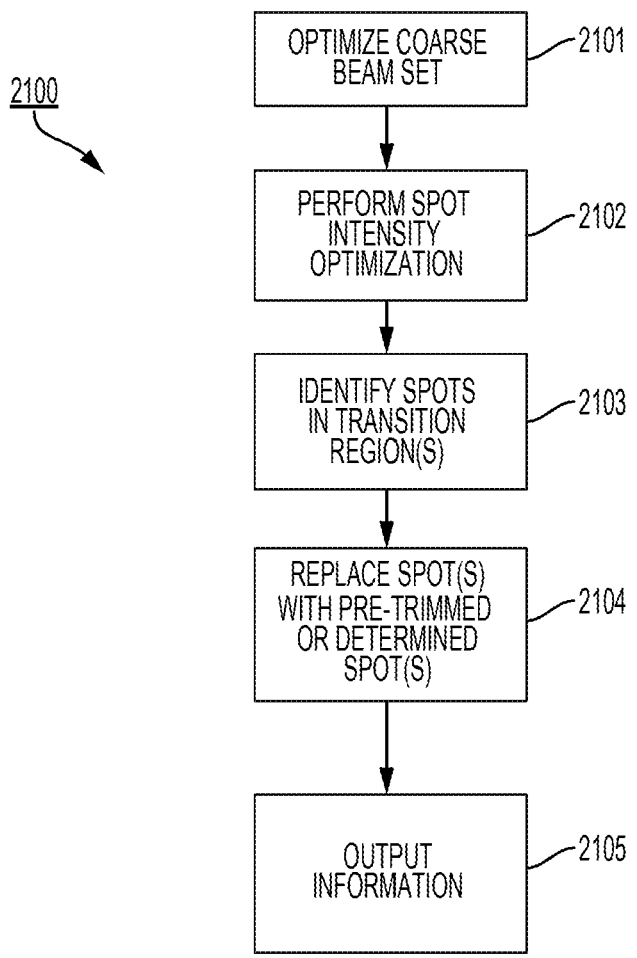
FIG. 37 is a flowchart showing an example of an optimization process performed to model, and to obtain, treatment plan information.

FIG. 37 shows an example of an optimization process 2100 that may be performed, e.g., by the TPP. The process may be implemented as a computer program stored on one or more non-transitory machine-readable media. The instructions may be executed on one or more processing devices (e.g., microprocessors) to implement the operations shown in FIG. 37. In this regard, although the process of FIG. 37 is defined in terms of physical entities, such as spots, intensities, treatment areas, and so forth, the process of FIG. 37 is not performed on those physical entities, but rather is performed using data that represents those physical entities and that models those physical entities and their interactions. Accordingly, although the description of FIG. 37 and the accompanying figures refers to the entities themselves (e.g., spots, treatment areas, etc.), the entity names are actually shorthand for data describing those entities (as the modeling and optimization process are performed on a computer, and output a treatment plan that is later implemented using a therapy system, such as those described herein).

Figure 38:
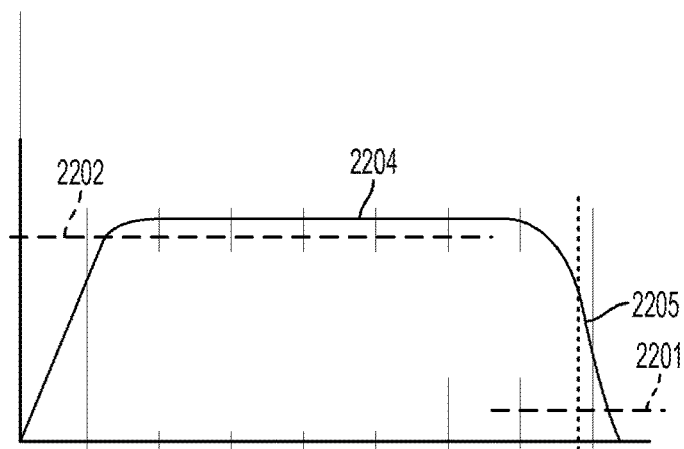
FIG. 38 is a side view of an example treatment area that identifies dosage to be applied to the treatment area.

The optimization process includes optimizing (2101) a coarse beam set. Referring to FIG. 38, in this example, this operation (2101) includes obtaining a minimum objective dosage 2202 and a maximum objective dosage 2201. In an example, the minimum objective is the minimum dosage to be applied to a treatment area 2204, such as a tumor (e.g., 98% of a desired dose over 98% of the treatment area). The maximum objective is the maximum amount of dosage to be applied outside the treatment area, e.g., to normal tissue or critical structures, such as organs. In some implementations, the dosage may be for a single scan (e.g., part of a target cumulative dose) and in some implementations the dosage may be the target cumulative dose.

The minimum dosage and maximum dosage may be determined, e.g., by a physician in the manner described above based on various factors. Data defining a set of Gaussian spots (in this example, spots A, B, C, D, and E of FIG. 39) is used to model the effect of radiation in those spots on the treatment area. Spots A, B, C, D, and E constitute an initial estimation of which spots will provide treatment to the treatment area given the constraints of the minimum objective and the maximum objective, e.g., spots that come closest to achieving the minimum objective but not exceeding the maximum objective. However, at this point, those objectives may not actually be met. At this stage—the coarse beam set—the spots have the same, or about the same, intensity, as depicted graphically in FIG. 39. In some implementations, different sets of coarse spots may be selected and the results of their application modeled. The set that most closely approximates the target dosage may be the set that is selected as the coarse set. For example, a set that is within a defined percentage of the target dose distribution may be selected, with the target percentage being any appropriate percentage, e.g., 5%, 10%, 15%, 20%, etc.

Figure 39:
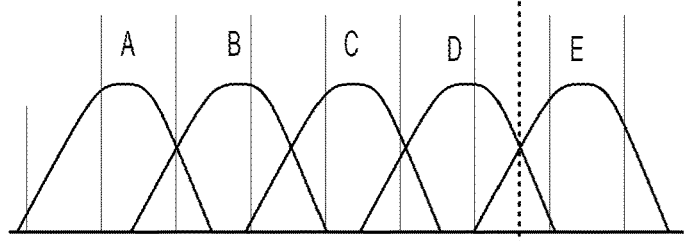
FIG. 39 is a side view of a coarse set of spots to be applied to the treatment area.
Figure 40:
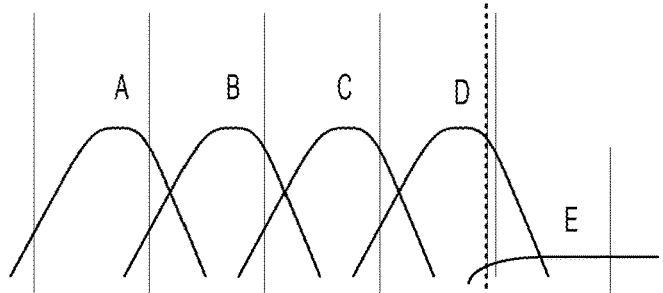
FIG. 40 is a side view of the set of spots of FIG. 39, with a spot having been intensity modulated.

The optimization process includes performing (2102) spot intensity optimization to further approximate the target dosage. In this example, spot intensity optimization includes identifying which spots should be increased or decreased in intensity given constraints, such as the minimum objective and the maximum objective (based, e.g., on the location of the treatment area, the location of normal tissue, the location of critical structures, and other appropriate criteria). Referring to FIGS. 39 and 40, in this example, the optimization process recognizes that spot E is at the edge of the treatment area 2204 and mostly outside of the treatment area. Therefore, the optimization process decreases the intensity of spot E (e.g., to some level at or below the maximum objective). This is depicted graphically in FIG. 40 by spot E being reduced in size and/or shape relative to spots A, B, C, and D. This optimization may be performed for multiple spots, as appropriate, and brings the modeled dosage closer to the target dosage. In some implementations, different beam intensities may be selected and the results of their application modeled. The beam intensity that most closely approximates the target dosage at the appropriate location may be the beam intensity that is selected.

The optimization process includes identifying (2103) spots within (e.g., that affect) one or more transition regions in the treatment area. For example a transition region may be the edge 2205 of the treatment area, and a spot at the transition region may include spot D (as evidenced by line 2206). Notably, a transition region need not only be at an edge of the treatment area. As described herein, transition regions may be at locations internal to the treatment area, and may depend upon the dose profile, the locations of critical structures in the treatment area, the shape of a tumor to be treated, and other appropriate factors.

Figure 41:
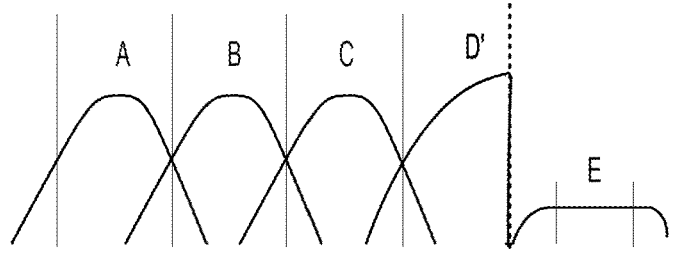
FIG. 41 is a side view of the set of spots of FIG. 40, with a spot having been replaced by a pre-trimmed spot.
Figure 42:
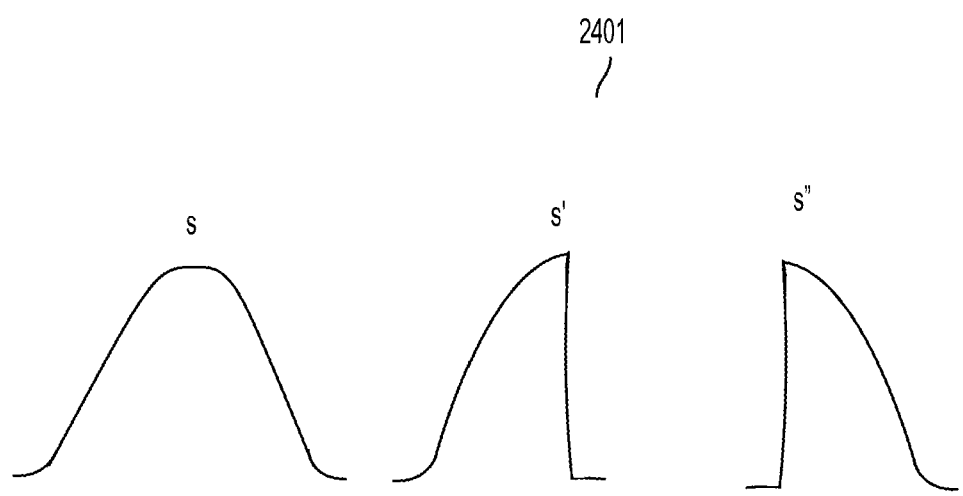
FIG. 42 shows side views of example spots in a library.

The optimization process includes replacing (2104) a spot (or spots) at the transition region(s) with one or more spots of alternate shapes. In some implementations, referring to FIG. 41, this operation includes replacing spot D at the transition regions with a pre-trimmed spot from the library that best approximates the target dose distribution. For example, FIG. 42 shows side views of examples of pre-trimmed spots in the library (with the side views showing distributions of protons within the spot, e.g., Gaussian or trimmed from Gaussian). An appropriate spot, such as spot 2401, is selected and replaced for spot D, with resulting replaced spot D' having (in this case) the shape shown in FIG. 41. In some implementations, differently-shaped spots may be selected from the library and the results of their application modeled. The pre-trimmed spot that most closely approximates the target dosage at the appropriate location may be selected for use. Operations 2101 through 2104 may be repeated, as necessary and appropriate, for different treatment areas and different locations within a single treatment area.

In some implementations, operation 2104 does not include use of pre-trimmed spots from the library. Instead, operation 2104 may include defining spot shapes based on information including, but not limited to, the desired treatment that is to be applied to an irradiation target and the ways in which the leaves and carriages of the adaptive aperture can move to produce one or more trimming curves. The configuration of one or more of the spots may be defined in real-time and, in some implementations, are not pre-defined. The spots may be defined using radius and/or orientation information for each spot, alone or in combination with any other appropriate information that can be used to specify spot size and shape. In this regard, in some implementations, real-time may include actions that occur on a continuous basis or track each other in time, taking into account delays associated with processing, data transmission, hardware, and the like.

The optimization process outputs (2105) information that defines which spots to apply to the treatment area. Some of the spots may not be trimmed (e.g., spots A, B, C), in which case only intensity and other appropriate information is provided to the therapy control system. For trimmed spots (e.g., spot D), those match the spots from the library, and information identifying those pre-trimmed spots is output to the control system. For implementations that do not employ pre-trimmed spots, information characterizing spot size and shape may be used. As described herein, information in the library defining the shape of those spots is indexed or otherwise associated with configurations of the adaptive aperture. Accordingly, that information is obtained by the control system, and used to control the adaptive aperture, as appropriate, to form those spots. For intensity-modulated spots, information for those spots is also output and used to produce spots with appropriate intensity. In some implementations, intensity-modulates spots may also be pre-trimmed spots that have been modulated in accordance with a desired intensity.

Figure 35:
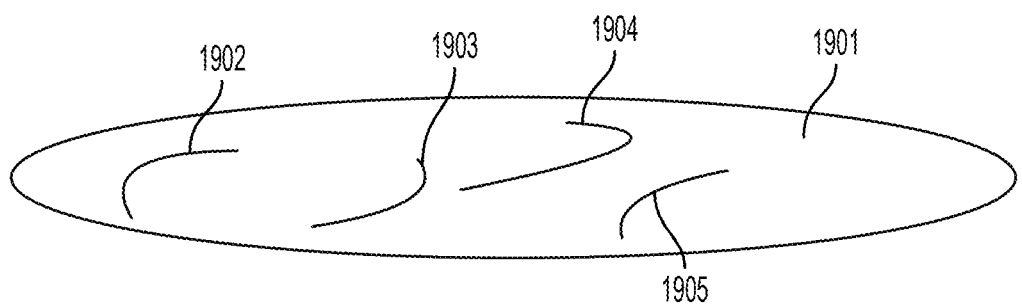
FIG. 35 is perspective view of a layer of an irradiation target and trimming curves superimposed thereon.

As noted above, a trimming curve may define an aperture, e.g., one or more curves or a hole that limit the extent to which radiation passes to an irradiation target. In some implementations, a trimming curve may simply be a line or curve that defines an edge of a spot or field of an irradiation target. For example referring to FIG. 35, a layer 1901 may include multiple internal trimming curves 1902 to 1905, none of which are closed curves.

Figure 17:
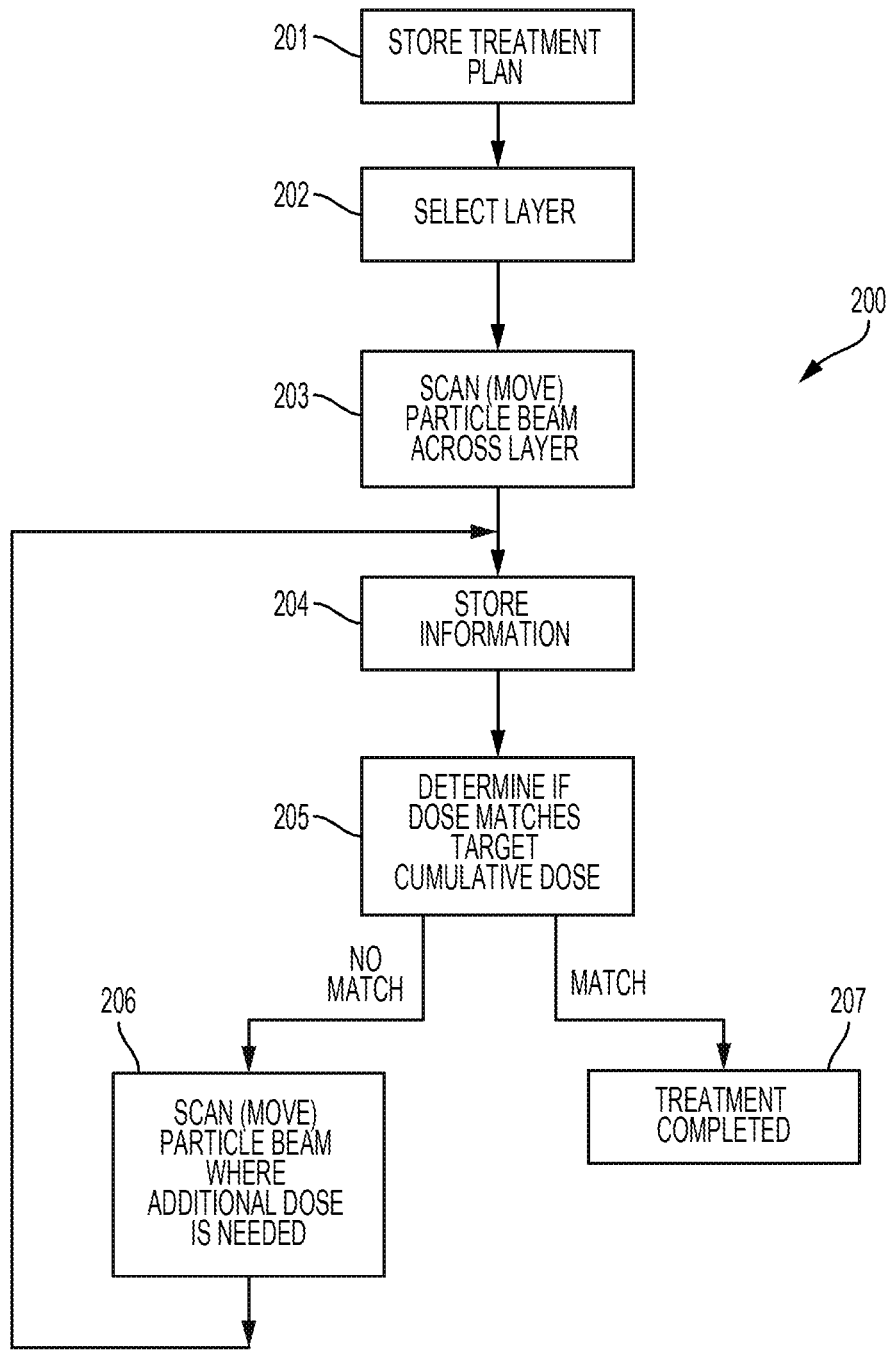
FIG. 17 is a flowchart showing an example process for performing raster scanning that may be performed using the hardware of FIGS. 10 to 15.
Figure 36:
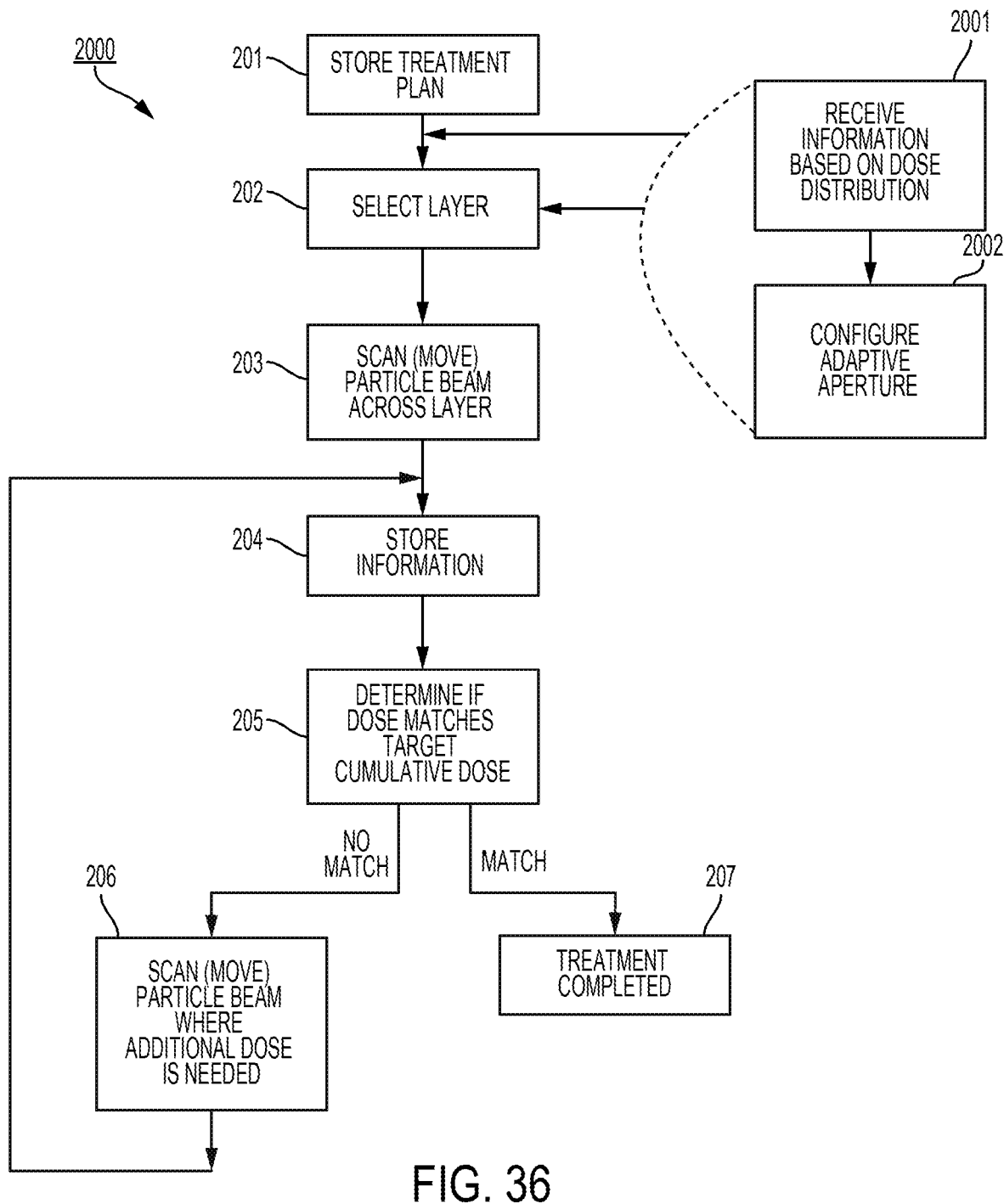
FIG. 36 is a flowchart showing an example scanning process that includes configuring trimming curves based on information about a target dose distribution.

FIG. 36 shows how configuration of the adaptive aperture fits into the process of FIG. 17. Other than operations 2001 and 2002, the operations of FIG. 36 are the same as those of FIG. 17. In this example, as part of the layer selection process or prior thereto, the control system of a particle therapy system receives (2001), from a TPP, information that is based on a dose distribution for an irradiation target; and configures (2002) the adaptive aperture by performing at least one of the following operations: (A) moving structures to trim spots of a particle beam so that the spots of the particle beam approximate pre-trimmed spots for which characteristics are obtained based on the information received; (B) moving structures to produce a trimming curve for each layer of an irradiation target based on specifications of trimming curves for different layers included in the information received; (C) moving structures to produce a single trimming curve for all radiation fields of an irradiation target based on specifications of the single trimming curve included in the information received; or (D) moving structures to produce a trimming curve for a radiation field of an irradiation target based on configuration information for the structures in the information received.

As described herein, in some implementations, the structures may be leaves that are moved into, or out of, the beam path. In some implementations, process 2000 of FIG. 36 may be implemented with a device other than the adaptive aperture. As appropriate, any two or more of the foregoing operations (A), (B), (C), or (D) may be combined, or used together, in whole or in part.

Also described herein is an example of a particle accelerator system, such as a proton or ion therapy system, which may employ adaptive apertures of FIGS. 1 to 7, 29, and 30, and which may configure those adaptive apertures in accordance with information from a TPP as described herein. The example particle therapy system includes a particle accelerator—in this example, a synchrocyclotron—mounted on a gantry. The gantry enables the accelerator to be rotated around a patient position, as explained in more detail below, to allow a particle beam from the particle accelerator hit any arbitrary treatment area in the patient. In some implementations, the gantry is steel and has two legs mounted for rotation on two respective bearings that lie on opposite sides of a patient. The particle accelerator is supported by a steel truss that is long enough to span a treatment area in which the patient lies and that is attached at both ends to the rotating legs of the gantry. As a result of rotation of the gantry around the patient, the particle accelerator also rotates.

In an example implementation, the particle accelerator (e.g., the synchrocyclotron) includes a cryostat that holds one or more superconducting coils, each for conducting a current that generates a magnetic field (B). In an example, the cryostat uses liquid helium (He) to maintain each coil at superconducting temperatures, e.g., 4° Kelvin (K). Magnetic yokes or smaller magnetic pole pieces are located inside the cryostat, and define the shape of a cavity in which particles are accelerated. Magnetic shims may pass through the magnetic yokes or pole pieces to change the shape and/or magnitude of the magnetic field in the cavity.

In this example implementation, the particle accelerator includes a particle source (e.g., a Penning Ion Gauge—PIG source) to provide an ionized plasma column to the cavity. Hydrogen gas is ionized to produce the plasma column. A voltage source provides a radio frequency (RF) voltage to the cavity to accelerate pulses of particles from the plasma column into the cavity. The magnetic field in the cavity is shaped to cause particles to move orbitally within the cavity. The magnetic field may be, e.g., at least 4 Tesla, as explained herein.

As noted, in an example, the particle accelerator is a synchrocyclotron. Accordingly, the RF voltage is swept across a range of frequencies to account for relativistic effects on the particles (e.g., increasing particle mass) when accelerating particles from the plasma column. The magnetic field produced by running current through a superconducting coil, together with the shape of the cavity, causes particles accelerated from the plasma column to accelerate orbitally within the cavity. In other implementations, a particle accelerator other than a synchrocyclotron may be used. For example, a cyclotron, a synchrotron, a linear accelerator, and so forth may be substituted for the synchrocyclotron described herein.

In the example synchrocyclotron, a magnetic field regenerator ("regenerator") is positioned near the outside of the cavity (e.g., at an interior edge thereof) to adjust the existing magnetic field inside the cavity to thereby change locations (e.g., the pitch and angle) of successive orbits of the particles accelerated from the plasma column so that, eventually, the particles output to an extraction channel that passes through the cryostat. The regenerator may increase the magnetic field at a point in the cavity (e.g., it may produce a magnetic field "bump" of about 2 Tesla or so at an area of the cavity), thereby causing each successive orbit of particles at that point to precess outwardly toward the entry point of the extraction channel until it reaches the extraction channel. The extraction channel receives, from the cavity, particles accelerated from the plasma column and outputs the received particles from the cavity as a particle beam.

The superconducting ("main") coils can produce relatively high magnetic fields. The maximum magnetic field generated by a main coil may be within a range of 4 T to 20 T or more. For example, a main coil may be used to generate magnetic fields at, or that exceed, one or more of the following magnitudes: 4.0 T, 4.1 T, 4.2 T, 4.3 T, 4.4 T, 4.5 T, 4.6 T, 4.7 T, 4.8 T, 4.9 T, 5.0 T, 5.1 T, 5.2 T, 5.3 T, 5.4 T, 5.5 T, 5.6 T, 5.7 T, 5.8 T, 5.9 T, 6.0 T, 6.1 T, 6.2 T, 6.3 T, 6.4 T, 6.5 T, 6.6 T, 6.7 T, 6.8 T, 6.9 T, 7.0 T, 7.1 T, 7.2 T, 7.3 T, 7.4 T, 7.5 T, 7.6 T, 7.7 T, 7.8 T, 7.9 T, 8.0 T, 8.1 T, 8.2 T, 8.3 T, 8.4 T, 8.5 T, 8.6 T, 8.7 T, 8.8 T, 8.9 T, 9.0 T, 9.1 T, 9.2 T, 9.3 T, 9.4 T, 9.5 T, 9.6 T, 9.7 T, 9.8 T, 9.9 T, 10.0 T, 10.1 T, 10.2 T, 10.3 T, 10.4 T, 10.5 T, 10.6 T, 10.7 T, 10.8 T, 10.9 T, 11.0 T, 11.1 T, 11.2 T, 11.3 T, 11.4 T, 11.5 T, 11.6 T, 11.7 T, 11.8 T, 11.9 T, 12.0 T, 12.1 T, 12.2 T, 12.3 T, 12.4 T, 12.5 T, 12.6 T, 12.7 T, 12.8 T, 12.9 T, 13.0 T, 13.1 T, 13.2 T, 13.3 T, 13.4 T, 13.5 T, 13.6 T, 13.7 T, 13.8 T, 13.9 T, 14.0 T, 14.1 T, 14.2 T, 14.3 T, 14.4 T, 14.5 T, 14.6 T, 14.7 T, 14.8 T, 14.9 T, 15.0 T, 15.1 T, 15.2 T, 15.3 T, 15.4 T, 15.5 T, 15.6 T, 15.7 T, 15.8 T, 15.9 T, 16.0 T, 16.1 T, 16.2 T, 16.3 T, 16.4 T, 16.5 T, 16.6 T, 16.7 T, 16.8 T, 16.9 T, 17.0 T, 17.1 T, 17.2 T, 17.3 T, 17.4 T, 17.5 T, 17.6 T, 17.7 T, 17.8 T, 17.9 T, 18.0 T, 18.1 T, 18.2 T, 18.3 T, 18.4 T, 18.5 T, 18.6 T, 18.7 T, 18.8 T, 18.9 T, 19.0 T, 19.1 T, 19.2 T, 19.3 T, 19.4 T, 19.5 T, 19.6 T, 19.7 T, 19.8 T, 19.9 T, 20.0 T, 20.1 T, 20.2 T, 20.3 T, 20.4 T, 20.5 T, 20.6 T, 20.7 T, 20.8 T, 20.9 T, or more. Furthermore, a main coil may be used to generate magnetic fields that are within the range of 4 T to 20 T (or more, or less) that are not specifically listed above.

Figure 8:
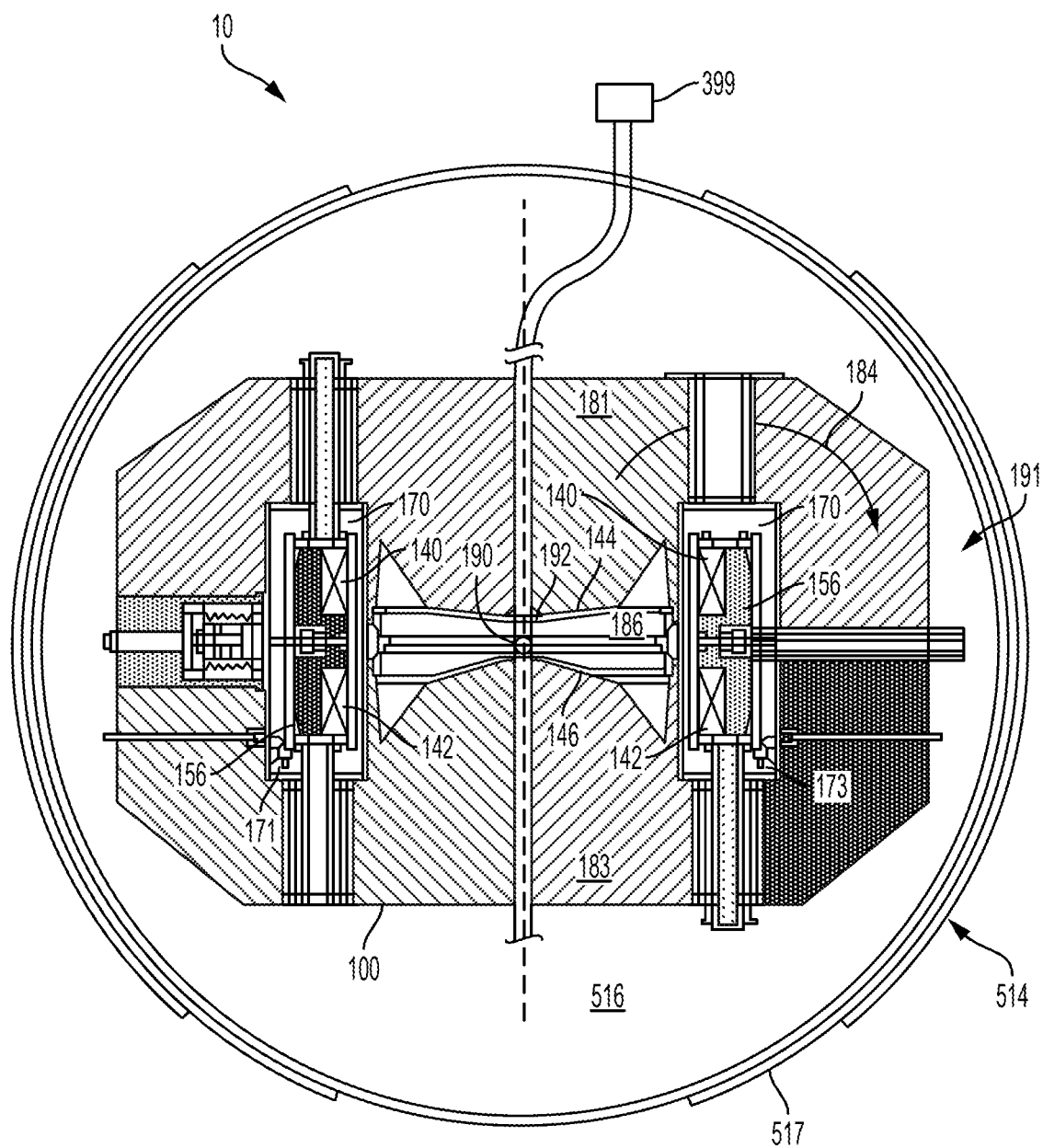
FIG. 8 is a cross-sectional view of an example synchrocyclotron for use in a particle therapy system.
Figure 9:
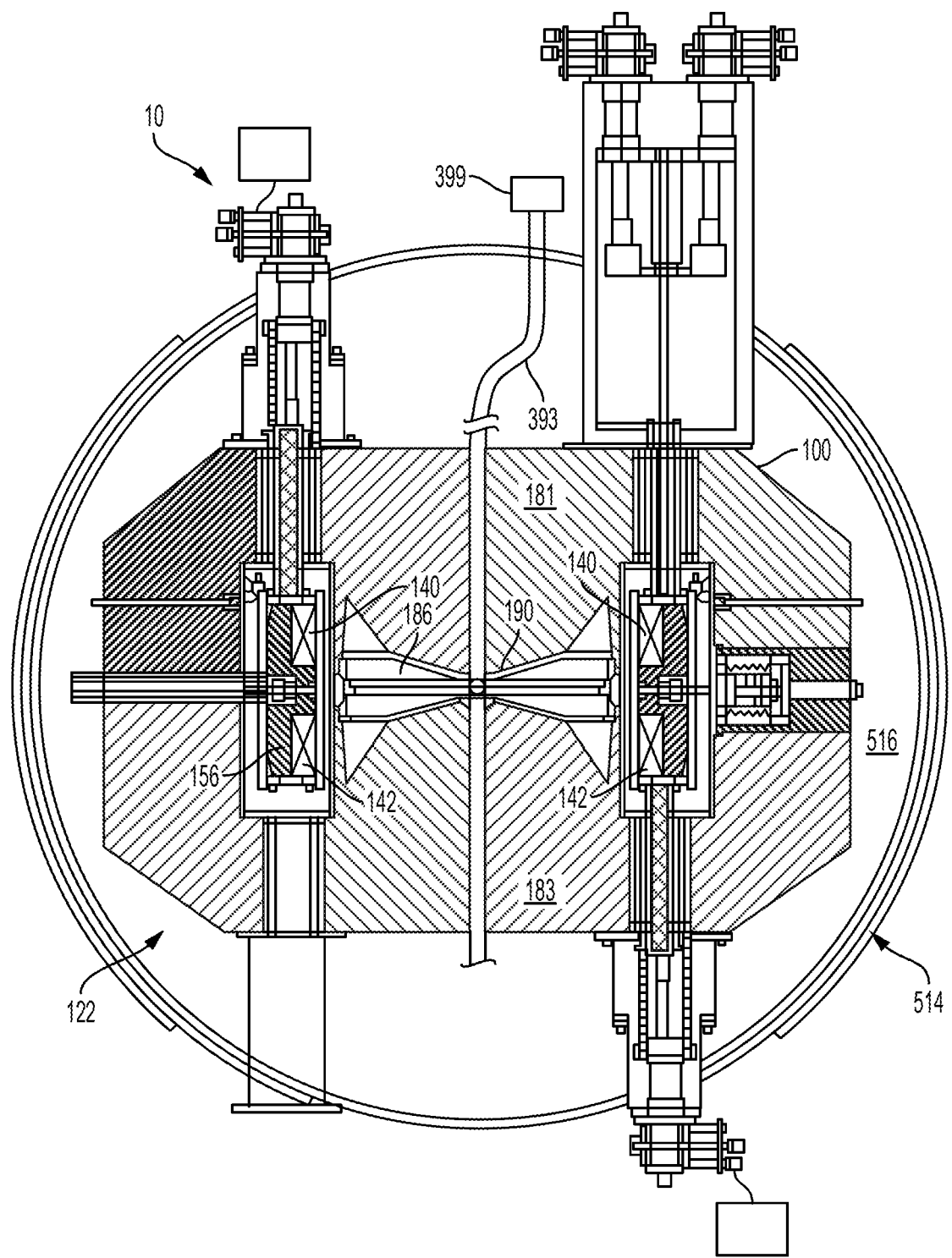
FIG. 9 is a cross-sectional view of an example synchrocyclotron for use in a particle therapy system.

In some implementations, such as the implementation shown in FIGS. 8 and 9, large ferromagnetic magnetic yokes act as a return for stray magnetic field produced by the superconducting coils. For example, in some implementations, the superconducting magnet can generate a relatively high magnetic field of, e.g., 4 T or more, resulting in considerable stray magnetic fields. In some systems, such as that shown in FIGS. 8 and 9, the relatively large ferromagnetic return yoke 100 is used as a return for the magnetic field generated by superconducting coils. A magnetic shield surrounds the yoke. The return yoke and the shield together dissipated stray magnetic field, thereby reducing the possibility that stray magnetic fields will adversely affect the operation of the accelerator.

In some implementations, the return yoke and shield may be replaced by, or augmented by, an active return system. An example active return system includes one or more active return coils that conduct current in a direction opposite to current through the main superconducting coils. In some example implementations, there is an active return coil for each superconducting coil, e.g., two active return coils-one for each superconducting coil (referred to as a "main" coil). Each active return coil may also be a superconducting coil that surrounds the outside of a corresponding main superconducting coil concentrically.

Current passes through the active return coils in a direction that is opposite to the direction of current passing through the main coils. The current passing through the active return coils thus generates a magnetic field that is opposite in polarity to the magnetic field generated by the main coils. As a result, the magnetic field generated by an active return coil is able to dissipate at least some of the relatively strong stray magnetic field resulting from the corresponding main coil. In some implementations, each active return may be used to generate a magnetic field of between 2.5 T and 12 T or more. For example, the magnetic field may be 2.5 T, 2.6 T, 2.7 T, 2.8 T, 2.9 T, 3.0 T, 3.1 T, 3.2 T, 3.3 T, 3.4 T, 3.5 T, 3.6 T, 3.7 T, 3.8 T, 3.9 T, 4.0 T, 4.1 T, 4.2 T, 4.3 T, 4.4 T, 4.5 T, 4.6 T, 4.7 T, 4.8 T, 4.9 T, 5.0 T, 5.1 T, 5.2 T, 5.3 T, 5.4 T, 5.5 T, 5.6 T, 5.7 T, 5.8 T, 5.9 T, 6.0 T, 6.1 T, 6.2 T, 6.3 T, 6.4 T, 6.5 T, 6.6 T, 6.7 T, 6.8 T, 6.9 T, 7.0 T, 7.1 T, 7.2 T, 7.3 T, 7.4 T, 7.5 T, 7.6 T, 7.7 T, 7.8 T, 7.9 T, 8.0 T, 8.1 T, 8.2 T, 8.3 T, 8.4 T, 8.5 T, 8.6 T, 8.7 T, 8.8 T, 8.9 T, 9.0 T, 9.1 T, 9.2 T, 9.3 T, 9.4 T, 9.5 T, 9.6 T, 9.7 T, 9.8 T, 9.9 T, 10.0 T, 10.1 T, 10.2 T, 10.3 T, 10.4 T, 10.5 T, 10.6 T, 10.7 T, 10.8 T, 10.9 T, 11.0 T, 11.1 T, 11.2 T, 11.3 T, 11.4 T, 11.5 T, 11.6 T, 11.7 T, 11.8 T, 11.9 T, 12.0 T, or more. Furthermore, an active return coil may be used to generate magnetic fields that are within the range of 2.5 T to 12 T (or more, or less) that are not specifically listed above.

Figure 10:
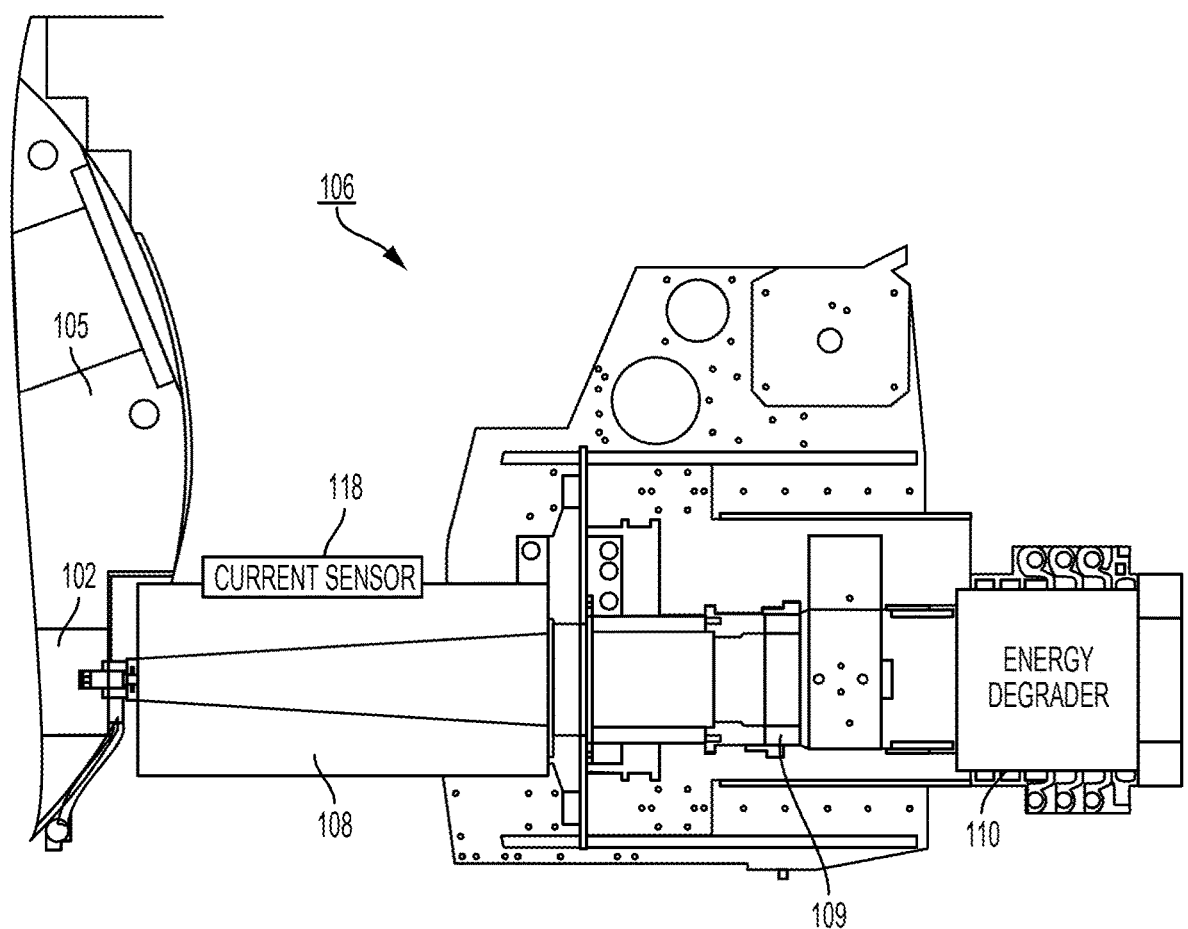
FIG. 10 is a side view of an example scanning system.
Figure 11:
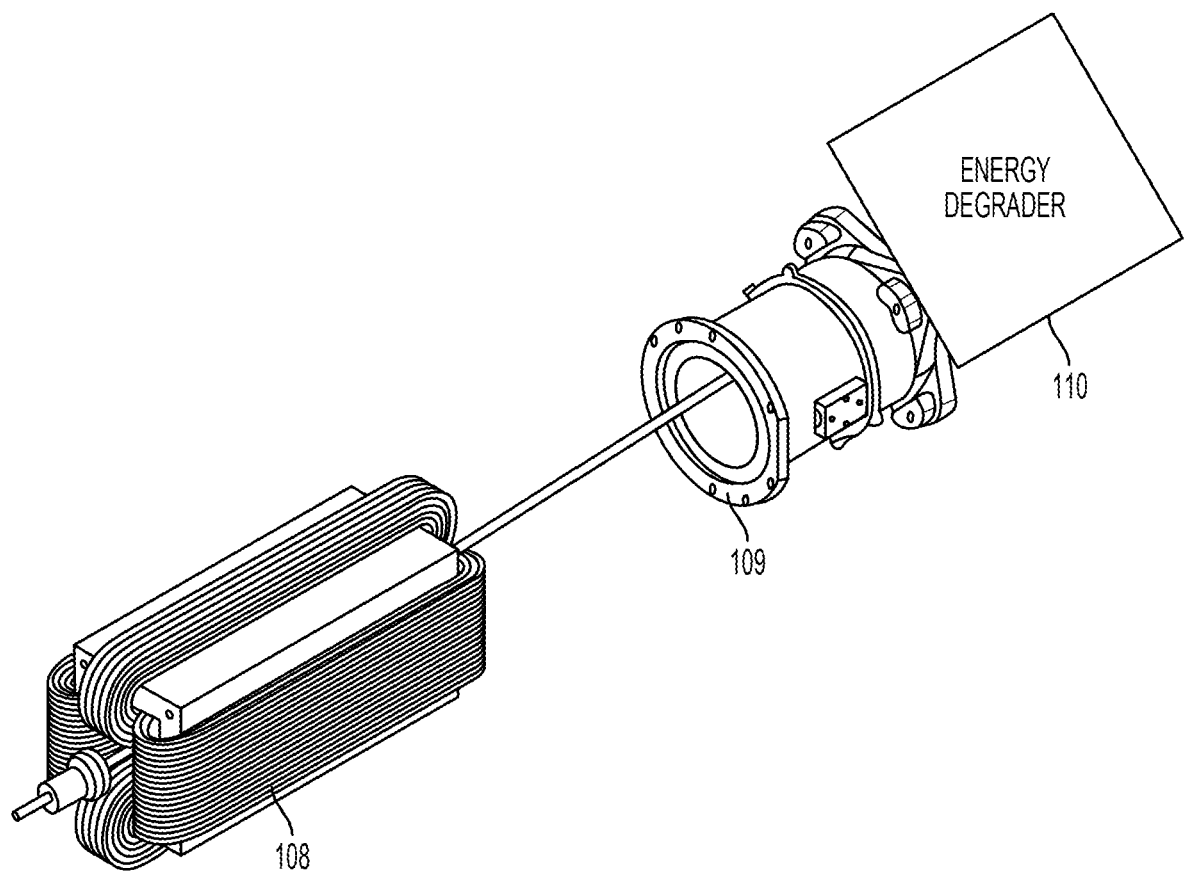
FIG. 11 is a perspective view of components of an example scanning system.

Referring to FIG. 10, at the output of extraction channel 102 of particle accelerator 105 (which may have the configuration shown in FIGS. 8 and 9), is an example scanning system 106 that may be used to scan the particle beam across at least part of an irradiation target. FIG. 11 also shows examples of components of the scanning system. These include, but are not limited to, a scanning magnet 108, an ion chamber 109, and an energy degrader 110. Other components that may be incorporated into the scanning system are not shown in FIG. 11, including, e.g., one or more scatterers for changing beam spot size. The example scanning system, including components thereof, may be mounted to the gantry and move along with the particle accelerator during movement of the gantry.

In an example operation, scanning magnet 108 is controllable in two dimensions (e.g., Cartesian XY dimensions) to direct the particle beam across a treatment area (e.g., a cross-section) of an irradiation target. Ion chamber 109 detects the dosage of the beam and feeds-back that information to a control system to adjust beam movement. Energy degrader 110 is controllable to move material (e.g., one or more individual plates) into, and out of, the path of the particle beam to change the energy of the particle beam and therefore the depth to which the particle beam will penetrate the irradiation target. In this way, the energy degrader selects a depth-wise layer of an irradiation target to scan in two dimensions.

Figure 13:
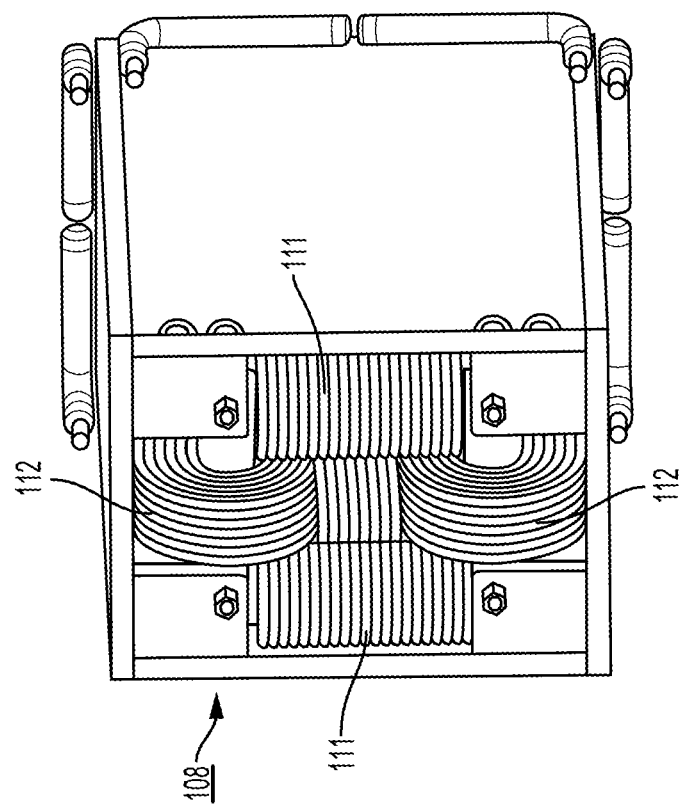
FIG. 13 is a perspective view of an example magnet for use in a scanning system of the type shown in FIGS. 10 and 11.
Figure 12:
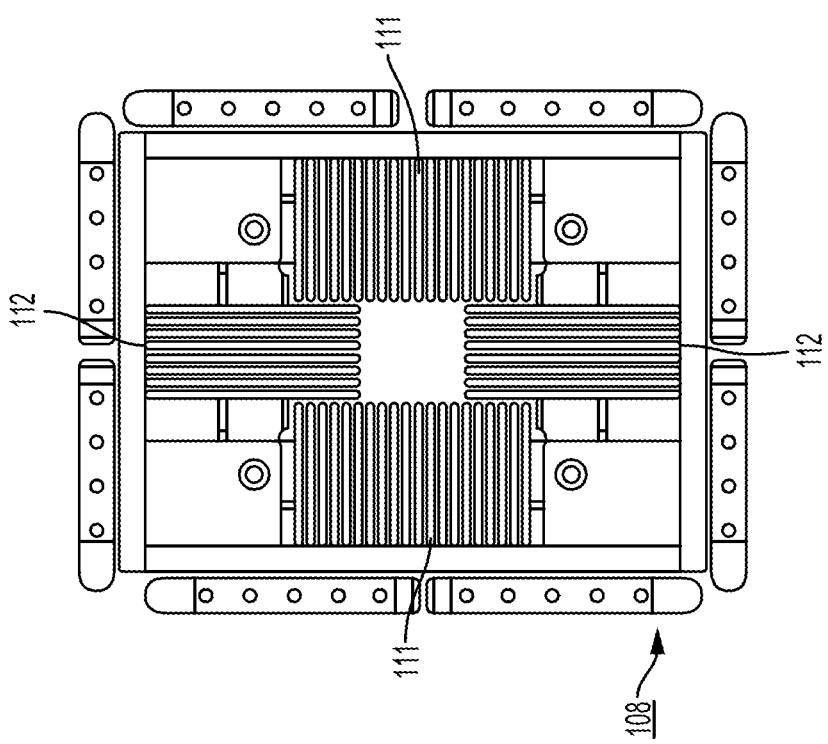
FIG. 12 is a front view of an example magnet for use in a scanning system of the type shown in FIGS. 10 and 11.

FIGS. 12 and 13 show views of an example scanning magnet 108. In this example implementation, scanning magnet 108 includes two coils 111, which control particle beam movement in the X-dimension, and two coils 112, which control particle beam movement in the Y-dimension. Control is achieved, in some implementations, by varying current through one or both sets of coils to thereby vary the magnetic field(s) produced thereby. By varying the magnetic field(s) appropriately, the particle beam can be moved in the X- and/or Y-dimension across the irradiation target. In some implementations, the scanning magnet is not movable physically relative to the particle accelerator. In other implementations, the scanning magnet may be movable relative to the particle accelerator (e.g., in addition to the movement provided by the gantry). In some implementations, the scanning magnet may be controllable to move the particle beam continuously so that there is uninterrupted motion of the particle beam over at least part of, and possibly all of, a layer of an irradiation target being scanned or a portion thereof (e.g., a treatment area). In other implementations, the scanning magnets are controllable at intervals or specific times. In some implementations, there may be different scanning magnets to control all or part movement of a particle beam in the X- and/or Y-dimensions.

In some implementations, scanning magnet 108 may have an air core. In other implementations, scanning magnet 108 may have a ferromagnetic (e.g., an iron) core. In general, a magnet having an air core includes a magnetic coil around a core that is a non-ferromagnetic material, such as air. For example, an air core magnet may include self-supporting coils that surround air. In some implementations, an air core magnet may include coils that are wound around an insulator, such as ceramic or plastic, which may or may not include air.

In some cases, an air core may have advantages over a ferromagnetic core. For example, the amount that the particle beam moves (e.g., is deflected) in the X- and/or Y-dimensions is determined, at least in part, based on the amount of current applied to the magnet (referred to as the "magnet current"). A scanning magnet typically has a movement (or deflection) range, which is the extent over which the magnet will move the beam. At extremes of this range, such as at the edges, larger amounts of current are applied to the scanning magnet in order to achieve relatively high amounts of beam deflection. Some types of scanning magnets having a ferromagnetic core may saturate at these extremes, resulting in a non-linear relationship between current and magnet movement. That is, the amount of deflection produced by the magnet may not be linearly proportional to the amount of current applied to the magnet. Due to this non-linearity, in some cases, it may be difficult to determine and/or set some beam locations using magnet current. Accordingly, when a scanning magnet having a ferromagnetic core is used, there may need to be some calibration and/or compensation performed in order to correct for non-linearities such as that described above.

In contrast, a scanning magnet having an air core may not saturate in the same manner as a scanning magnet having a ferromagnetic core. For example, an air core magnet may not saturate or may saturate less than a magnet having a ferromagnetic core. As a result, the relationship between current and magnet movement may be more linear, particularly at the range extremes, making determinations of beam location based on magnet current more accurate, at least in some cases. This increased linearity also can enable more accurate movement of the beam, particularly at range extremes. That is, since the relationship between current and beam movement is generally more linear over a larger range when an air core scanning magnet is used, beam movement may be more easily reproducible using an air core scanning magnet. This can be advantageous, since a depth-wise layer of an irradiation target may require multiple scans, each providing a percentage of a total cumulative radiation dose. Precision in delivery of multiple doses to the same area, such as that which can be obtained through use of an air core scanning magnet, can affect the efficacy of the treatment.

Although the relationship between current and magnet movement may be more linear in an air core magnet, in some cases, an air core magnet may be more susceptible to stray magnetic fields than a magnet having a ferromagnetic core. These stray magnetic fields may impact the scanning magnet during motion of the scanning magnet produced by the gantry. Accordingly, in some implementations that use a scanning magnet having an air core, the current applied to the scanning magnet to move the beam may be calibrated to account for the position of the scanning magnet relative to the patient (or, correspondingly, to account for the position of the gantry, since the position of the gantry corresponds to the position of the scanning magnet relative to the patient). For example, the behavior of the scanning magnet may be determined and, if necessary, corrected, for different rotational positions (angles) of the gantry, e.g., by increasing or decreasing some applied current based on rotational position.

In some implementations, the scanning magnet may have a core that is comprised of both air and a ferromagnetic material (e.g., iron). In such implementations, the amount and configuration of air and ferromagnetic material in the core may be determined taking the foregoing factors into account.

In some implementations, a current sensor 118 may be connected to, or be otherwise associated with, scanning magnet 108. For example, the current sensor may be in communication with, but not connected to, the scanning magnet. In some implementations, the current sensor samples current applied to the magnet, which may include current to coil(s) for controlling beam scanning in the X-dimension and/or current to coil(s) for controlling beam scanning in the Y-dimension. The current sensor may sample current through the magnet at times that correspond to the occurrence of pulses in the particle beam or at a rate that exceeds the rate that the pulses occur in the particle beam. In the latter case, the samples, which identify the magnet current, are correlated to detection of the pulses by the ion chamber described below. For example, the times at which pulses are detected using the ion chamber (described below) may be correlated in time to samples from the current sensor, thereby identifying the current in the magnet coil(s) at the times of the pulses. Using the magnet current, it thus may be possible to determine the location on the irradiation target (e.g., on a depth-wise layer of the irradiation target) where each pulse, and thus dose of particles, was delivered. The location of the depth-wise layer may be determined based on the position of the energy degrader (e.g., the number of plates) in the beam path.

During operation, the magnitude(s) (e.g., value(s)) of the magnet current(s) may be stored for each location at which a dose is delivered, along with the amount (e.g., intensity) of the dose. A computer system, which may be either on the accelerator or remote from the accelerator and which may include memory and one or more processing devices, may correlate the magnet current to coordinates within the irradiation target, and those coordinates may be stored along with the amount of the dose. For example, the location may be identified by depth-wise layer number and Cartesian XY coordinates or by Cartesian XYZ coordinates (with the layer corresponding to the Z coordinate). In some implementations, both the magnitude of the magnet current and the coordinate locations may be stored along with the dose at each location. This information may be stored in memory either on, or remote from, the accelerator. As described in more detail herein, this information may be used during scanning to apply multiple doses to the same locations to achieve target cumulative doses.

In some implementations, ion chamber 109 detects dosage (e.g., one or more individual doses) applied by the particle beam to positions on an irradiation target by detecting the numbers of ion pairs created within a gas caused by incident radiation. The numbers of ion pairs correspond to the dose provided by the particle beam. That information is fed-back to the computer system and stored in memory along with the time that the dose is provided. This information may be correlated to, and stored in association with, the location at which the dose was provided and/or the magnitude of the magnet current at that time, as described above.

As described in more detail below, in some implementations, the scanning system is run open loop, in which case the particle beam is moved freely and uninterrupted across an irradiation target so as to substantially cover the target with radiation. As the radiation is delivered, dosimetry implemented by the particle therapy control system records (e.g., stores) the amount of the radiation per location and information corresponding to the location at which the radiation was delivered. The location at which the radiation was delivered may be recorded as coordinates or as one or more magnet current values, and the amount of the radiation that was delivered may be recorded as dosage in grays. Because the system is run open loop, the delivery of the radiation is not synchronized to the operation of the particle accelerator (e.g., to its RF cycle). However, the dosimetry may be synchronized to the operation of the particle accelerator. More specifically, the dosimetry records the amount and location of each dose delivered as the dose is delivered (that is, as close in time to delivery as possible given the limits of technology). Since the dose is delivered in synchronism with the operation of the accelerator (e.g., one pulse is delivered per RF cycle), in some implementations, the dosimetry that records the dose and the location operates in synchronism, or substantially in synchronism, with delivery of radiation doses to the target, and thus in synchronism with the operation of the particle accelerator, such as its RF cycle.

Figure 14:
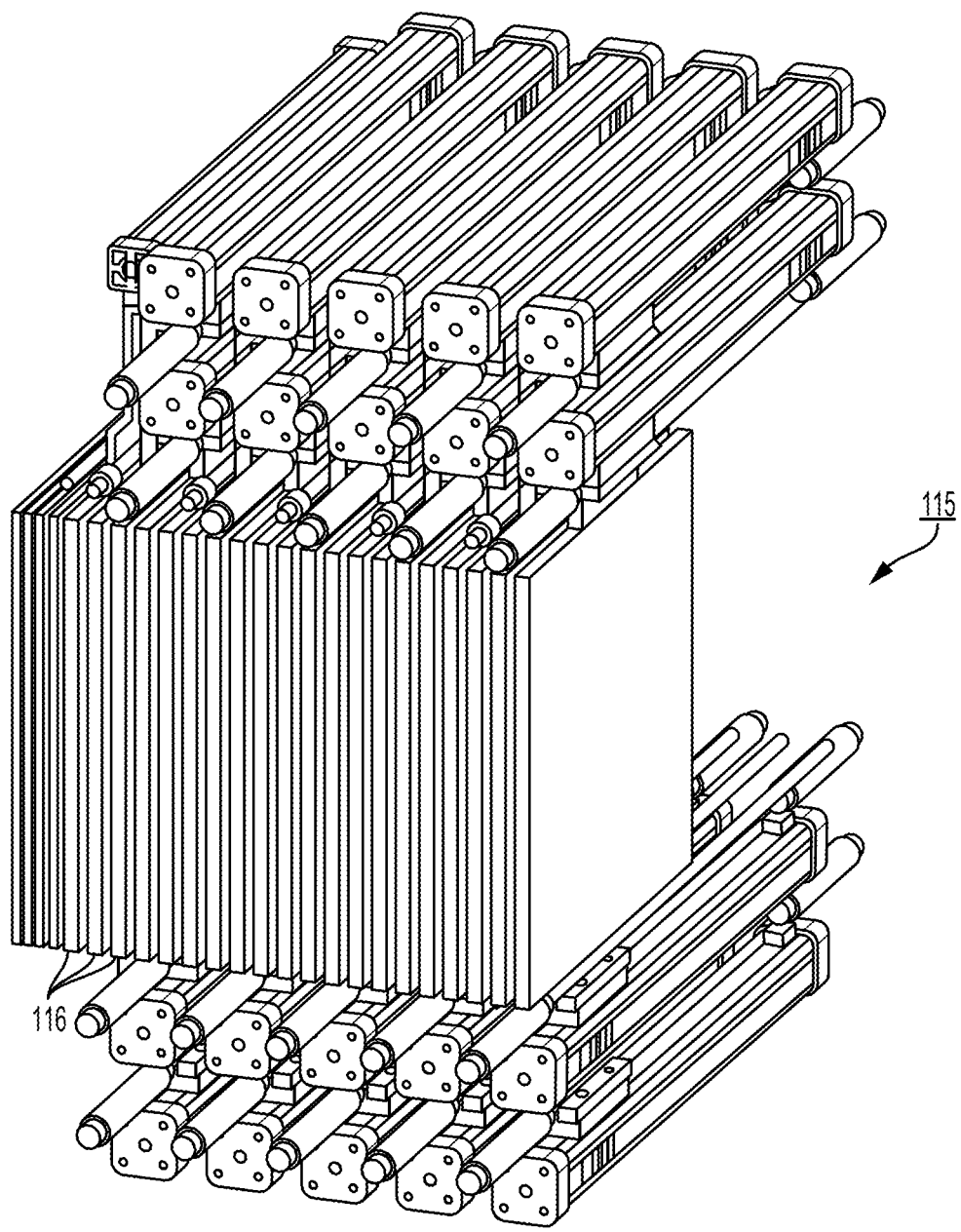
FIG. 14 is a perspective view of an example energy degrader (range modulator) for use in a scanning system of the type shown in FIGS. 10 and 11.

FIG. 14 shows a range modulator 115, which is an example implementation of energy degrader 110. In some implementations, such as that shown in FIG. 14, the range modulator includes a series of plates 116. The plates may be made of one or more of the following example materials: carbon, beryllium or other material of low atomic number. Other materials, however, may be used in place of, or in addition to, these example materials.

One or more of the plates is movable into, or out of, the beam path to thereby affect the energy of the particle beam and, thus, the depth of penetration of the particle beam within the irradiation target. For example, the more plates that are moved into the path of the particle beam, the more energy that will be absorbed by the plates, and the less energy the particle beam will have. Conversely, the fewer plates that are moved into the path of the particle beam, the less energy that will be absorbed by the plates, and the more energy the particle beam will have. Higher energy particle beams typically penetrate deeper into the irradiation target than do lower energy particle beams. In this context, "higher" and "lower" are meant as relative terms, and do not have any specific numeric connotations.

Figure 15:
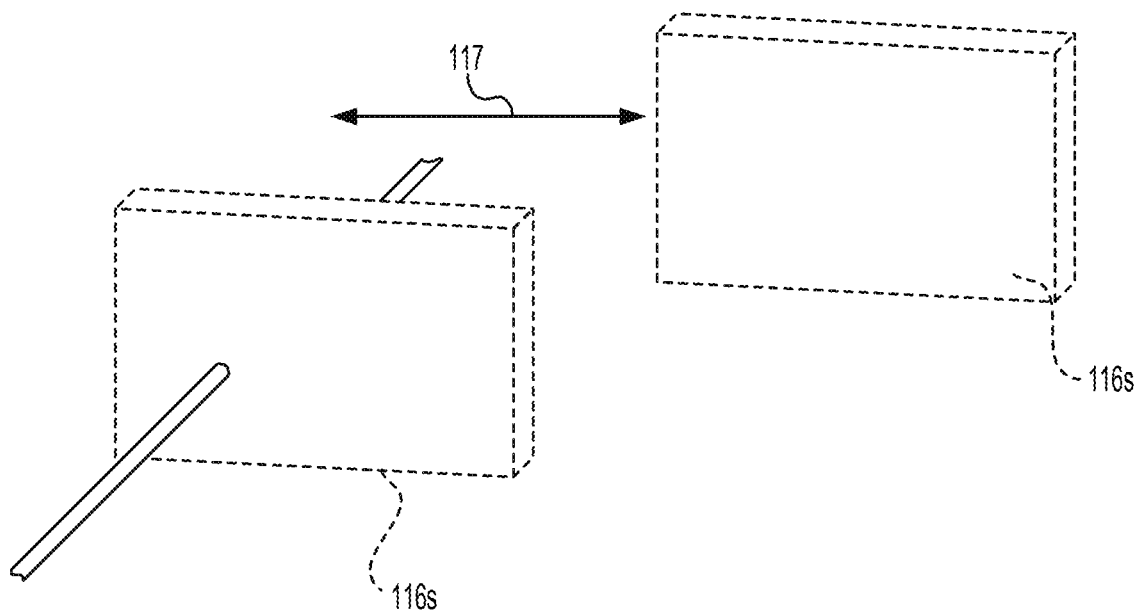
FIG. 15 is a perspective view of a process for moving a leaf of an energy degrader in the path of a particle beam.

Plates are moved physically into, and out of, the path of the particle beam. For example, as shown in FIG. 15, a plate 116a moves along the direction of arrow 117 between positions in the path of the particle beam and outside the path of the particle beam. The plates are computer-controlled. Generally, the number of plates that are moved into the path of the particle beam corresponds to the depth at which scanning of an irradiation target is to take place. For example, the irradiation target can be divided into cross-sections or depth-wise layers, each of which corresponds to an irradiation depth. One or more plates of the range modulator can be moved into, or out of, the beam path to the irradiation target in order to achieve the appropriate energy to irradiate each of these cross-sections or depth-wise layers of the irradiation target. The range modulator may be stationary relative to the particle beam during scanning of a part of (e.g., cross-section of) an irradiation target, except for its plates moving in and out of the path of the particle beam. Alternatively, the range modulator of FIGS. 14 and 15 may be replaced with a range modulator that, at least some of the time, tracks movement of the particle beam, thereby enabling use of smaller plates.

In implementations that use a range modulator of the type described above, the number of plates that are moved into the beam path determine/set the depth-wise layer of the irradiation target that is to be scanned. For example, if two plates are moved into the beam path, the layer will be more shallow than if one or no plates are moved into the beam path. The layer may be identified, and stored in memory, based on the number of plates moved into the beam path. In some implementations, the plates may have different heights. In such implementations, the heights of the various plates also affect which layer is to be scanned (e.g., how deep the particle beam will penetrate the target).

In some implementations, the particle accelerator may be a variable-energy particle accelerator. In example systems where a variable-energy particle accelerator is used, there may be less need for an energy degrader of the type described herein, as the energy level of the particle beam may be controlled by the particle accelerator. For example, in some systems that employ a variable-energy particle accelerator, an energy degrader may not be needed. In some systems that employ a variable-energy particle accelerator, an energy degrader may still be used to change beam energy levels.

In some implementations, a treatment plan is established prior to treating the irradiation target. The treatment plan may be stored in memory that is accessible to a computer system that controls operation of the particle therapy system. As described, the treatment plan may be received from a TPS/TPP and may include information about how radiation treatment is to be provided by the particle therapy system. For example, the treatment plan may specify how scanning is to be performed for a particular irradiation target. In some implementations, the treatment plan specifies that raster scanning is to be performed. Raster scanning includes producing an uninterrupted movement of the particle beam across the irradiation target. For example, the scanning magnet moves continually to scan (e.g., move) the particle beam across the irradiation target so as to produce uninterrupted movement of the particle beam over at least part of a layer of an irradiation target. The movement may be uninterrupted across an entire layer of the irradiation target or across only part of a layer. In some implementations, the beam may be moved at a constant speed along all or part of a layer of the irradiation target. In some implementations, the speed at which the beam is moved along all or part of a layer of the irradiation target may vary. For example, the particle beam may move more quickly across internal portions of a layer than at edges of the layer. The speed of movement may be specified in the treatment plan.

In some implementations, the treatment plan may also specify the target cumulative dose of radiation (particles) to be applied to various positions on layers of an irradiation target. The dose is cumulative in the sense that it may be achieved through application of one or more doses of particles. For example, the same location (e.g., in XYZ space) on an irradiation target may be irradiated ten times, each time with 10% of the target cumulative dose to achieve the target cumulative dose. In some implementations, the treatment plan need not specify the amount of dose for each location, the locations, or the number of times that locations are to be irradiated. That is, this information may be omitted from the treatment plan in some implementations. Rather, in some implementations, the intensity of the particle beam may be set beforehand to provide a particular dose of radiation per instance of irradiation. The particle beam may then be scanned over a layer of the irradiation target in an open loop manner, without requiring feedback to move to a next location. As the particle beam is scanned, the location of the beam is determined and the corresponding dose at that location is determined. The determination may be made at about the same time as the scanning and delivery (that is, as close in time to delivery as possible given the limits of technology). The cumulative dose at that location, which includes the current dose as well as any dose previously delivered during the current treatment, is compared to the target cumulative dose from the treatment plan. If the two do not match, then additional dose may be applied to that location during a subsequent scan. Since it is not always known precisely how much radiation will be delivered to a location per scan, the number of times that a location is scanned may not be set beforehand. Likewise, since there may be fluctuations in the amount of radiation actually delivered per scan to a location, the precise amount of radiation per scan is not necessarily set beforehand. Consequently, in some implementations, such information need not be included in the treatment plan.

In some implementations, the treatment plan may also include one or more patterns, over which the particle beam may be scanned per layer. The treatment plan may also specify the number of plates of an energy degrader to achieve a particular energy level/layer. Other implementations may include information in addition to, or instead of, that specified above.

In some implementations, the overall treatment plan of an irradiation target may include different treatment plans for different cross-sections (layers) of the irradiation target. The treatment plans for different cross-sections may contain the same information or different information, such as that provided above.

Figure 16:
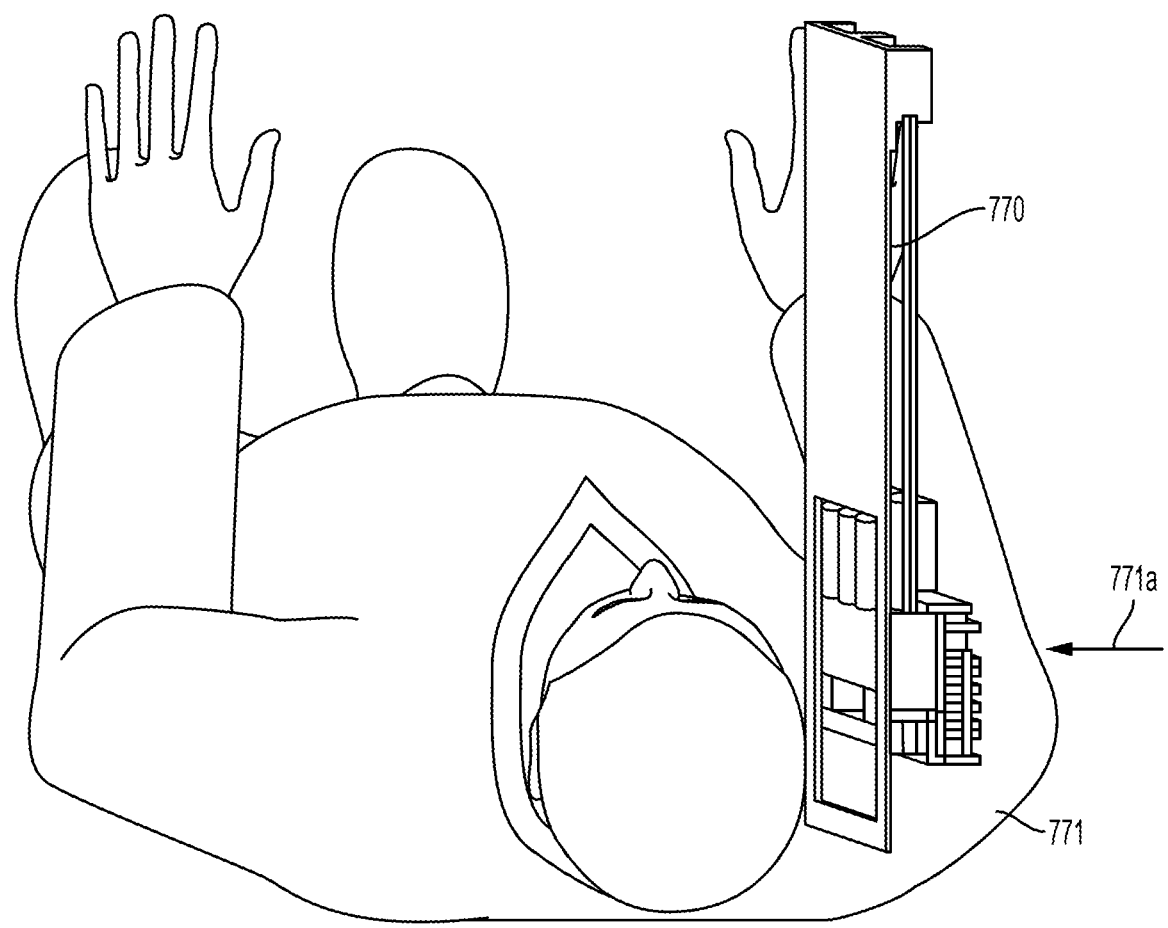
FIG. 16 is a perspective view of an adaptive aperture positioned relative to a patient during particle therapy treatment.

The scanning system may include the adaptive aperture of FIGS. 1 to 7, 29, and 30 (or a variant thereof), which is placeable relative to the irradiation target to limit the extent of the particle beam and thereby limit the extent of the particle beam. For example, the adaptive aperture may be placed in the beam path down-beam of the energy degrader and before the particle beam hits the treatment area of the irradiation target. The adaptive aperture is controllable to allow at least part of the particle beam to pass therethrough and then hit certain parts of the treatment area, while preventing the particle beam from hitting other parts of the patient. For example, the adaptive aperture may be controlled to prevent the particle beam from hitting healthy tissue or to prevent the particle beam from hitting other parts of the irradiation target (e.g., if certain parts of the target are to receive more radiation than other parts). The adaptive aperture may be controlled to perform trimming internal to, or external to, a layer of an irradiation target, as described. FIG. 16 depicts placement of an implementation 770 of the adaptive aperture described herein relative to a patient 771. The direction of beam 771a is also shown.

As noted above, in some implementations, scanning is performed in an open-loop manner, e.g., by an open-loop control system that may be implemented using one or more processing devices, such as the computing device that controls the particle therapy system. In this example, open-loop scanning includes moving the particle beam across an irradiation target to substantially cover the target with radiation. In some implementations, movement is not synchronized with operation of the accelerator, e.g., with the RF frequency, but rather runs independently of the operation of the accelerator when the accelerator is operating. For example, movement of the particle beam may be uninterrupted, and not dependent upon the RF cycle of the particle accelerator. Uninterrupted movement may occur across all or part of a layer of an irradiation target. However, as described herein, the dosimetry may be synchronized with delivery of pulses of the particle beam to the irradiation target. In examples where the dosimetry is synchronized with delivery of pulses of the particle beam, the dosimetry is also synchronized with operation of the accelerator (e.g., with the RF frequency used to draw pulses of the particle beam from the ion source plasma column).

The radiation level of an individual dose of particle beam (e.g., an individual pulse from the accelerator) may be set beforehand. For example, each individual dose may be specified in grays. An individual dose may be, or correspond to, a percentage of the target cumulative dose that is to be applied to a location (e.g., an XYZ coordinate) in an irradiation target. In some implementations, the individual dose may be 100% of the target cumulative dose and, as a result, only a single scan may be needed to deliver a single dose of radiation (e.g., one or more particle pulses) per location to the irradiation target. In some implementations, the individual dose may be less than 100% of the target cumulative dose, resulting in the need for multiple scans of the same location to deliver multiple doses of radiation to the irradiation target. The individual dose may be any appropriate percentage of the target cumulative dose, such as: 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or any percentage in between these values.

The scanning magnet current may be controlled, in accordance with the treatment plan, to scan a depth-wise layer of the irradiation target. The layer is selected by appropriately positioning one or more energy degraders from the range compensator in the path of the particle beam and/or by setting an energy level of a variable-energy particle accelerator. As the layer is scanned, the current sensor samples the current applied to the scanning magnet. The amount of magnet current may be recorded, e.g., stored in memory. If more than one magnet or magnet coil is used, the amount of magnet current may be stored along with the identity of the magnet or coil. In addition, the current may be correlated to coordinates within the irradiation target (e.g., Cartesian XYZ coordinates) and those coordinates may be stored in addition to, or instead of, the corresponding magnet current. As explained above, the current sensor may sample the magnet current and correlate the sampling time to the time at which an irradiation dose (e.g., pulse) is delivered.

In this regard, ion chamber 109 may detect the intensity of doses delivered to the irradiation target as that dose is delivered. The intensity of each dose is recorded (e.g., stored in memory) along with the location of each delivered dose. As noted, the location of each delivered dose may be stored by coordinates, magnet current, or using some other appropriate metric. As noted above, the dosimetry—the dose verification—may be synchronized with delivery of the dose and, thus, with the output of the accelerator (which corresponds to the RF frequency, as described above). Accordingly, in some implementations, each time a dose is delivered, the intensity of that dose is determined almost immediately and the location at which the dose is applied is determined almost immediately. This information may be stored in one or more tables (e.g., one table per layer or multiple tables per layer) or other appropriate computer storage construct.

In some implementations, the tables may be updated as additional doses are delivered. For example, a table may keep a running track of the amount of dose delivered at each location. So, if the beam dose is "X" grays, at a first scan pass, the table may record X grays for a location. At a second scan pass, the table may record 2X grays, and so forth until the target cumulative dose is reached.

In this regard, for each location, a processing device associated with the accelerator (e.g., the computer system that controls the particle therapy system) may compare the cumulative dose from a table, such as that described above, to the target cumulative dose. If the cumulative dose matches the target cumulative dose, treatment for that location (or layer) is deemed completed. If the cumulative dose does not match the target cumulative dose, additional treatment is performed. For example, the layer or location is scanned again at the same locations, which are obtained from the table. The linear correlation between magnet current and beam movement produced by use of an air core magnet can facilitate repeated, and relatively accurate, repeated scanning at the same locations during multiple passes of the beam during scanning. The leaves of the adaptive aperture described herein may be moved slightly (e.g., a fraction of a millimeter, a millimeter, or multiple millimeters) between each scan of the same area, as described above.

Scanning may be repeated, at the same locations, any appropriate number of times until the target cumulative dose is reached at each location. In this regard, the entire layer may be re-scanned or only select portions of the layer may be re-scanned, dependent upon the target cumulative doses for the different locations on the layer. In some implementations, the intensity of the particle beam is not varied between scans. In other implementations, the intensity of the particle beam may be varied between scans, particularly if a small dose is required to top-off a cumulative dose to reach the target cumulative dose. The intensity of the dose may be increased or decreased, e.g., by altering the operation of the ion source (e.g., increasing the plasma ionization), altering the sweep of the RF frequency, or by any other appropriate methods.

As noted, scanning may be repeated for an entire layer or for only a portion of a layer. In some implementations, an entire layer, or a portion thereof, may be fully treated before treating another layer. That is, scanning may be repeated until the total cumulative dose is reached for each location on a layer before another layer is treated. In some implementations, each layer may be treated partially (e.g., scanned once) in sequence, and then re-scanned in sequence. In some implementations, several designated layers may be completely treated before other layers are treated. In some implementations, the entire target may be scanned once, followed by successive scans of the entire target until the appropriate total cumulative dose is delivered to each location. The adaptive aperture may be reconfigured for each scan or its configuration may remain static between scans.

During movement between layers, the beam may be turned-off. For example, during movement between layers, the ion source may be turned-off, thereby disrupting the output of the beam. During movement between layers, the RF sweep in the particle accelerator may be turned-off, thereby disrupting the extraction (and thus output) of the beam. During movement between layers, both the ion source and the circuitry that creates the RF sweep may be deactivated in some implementations. In some implementations, rather than turning-off the ion source and/or the RF sweep during movement between layers, the beam may be deflected to a beam-absorbing material using a kicker magnet (not shown) or the scanning magnet.

Different cross-sections of the irradiation target may be scanned according to different treatment plans. As described above, an energy degrader is used to control the scanning depth. In some implementations, the particle beam may be interrupted or redirected during configuration of the energy degrader. In other implementations, this need not be the case.

Described herein are examples of treating cross-sections of an irradiation target. These may be cross-sections that are roughly perpendicular to the direction of the particle beam. However, the concepts described herein are equally applicable to treating other portions of an irradiation target that are not cross-sections perpendicular to the direction of the particle beam. For example, an irradiation target may be segmented into spherical, cubical or other shaped volumes, and those volumes may be treated using the example processes, systems, and/or devices described herein.

FIG. 17 is a flowchart showing an example implementation of the scanning process described herein. Although process 200 of FIG. 17 is described in the context of the hardware described herein, process 200 may be performed using any appropriate hardware. The operations shown in process 200 may be performed in the same order as depicted or in a different order, where appropriate.

According to process 200, a treatment plan is stored (201). The treatment plan may be a treatment plan as described above. For example, the treatment plan may specify the type of scanning (e.g., uninterrupted raster scanning) and the total cumulative dose of radiation to be delivered to each location in each layer of an irradiation target. In some implementations, the treatment plan may omit, e.g., the doses to be delivered for each scan at individual locations and their intensities, as well as the number of doses to be delivered to each location and the identity of the locations. In some implementations, the treatment plan may include, e.g., the doses to be delivered for each scan at individual locations and their intensities, as well as the number of doses to be delivered to each location and the identity of the locations.

Figure 18:
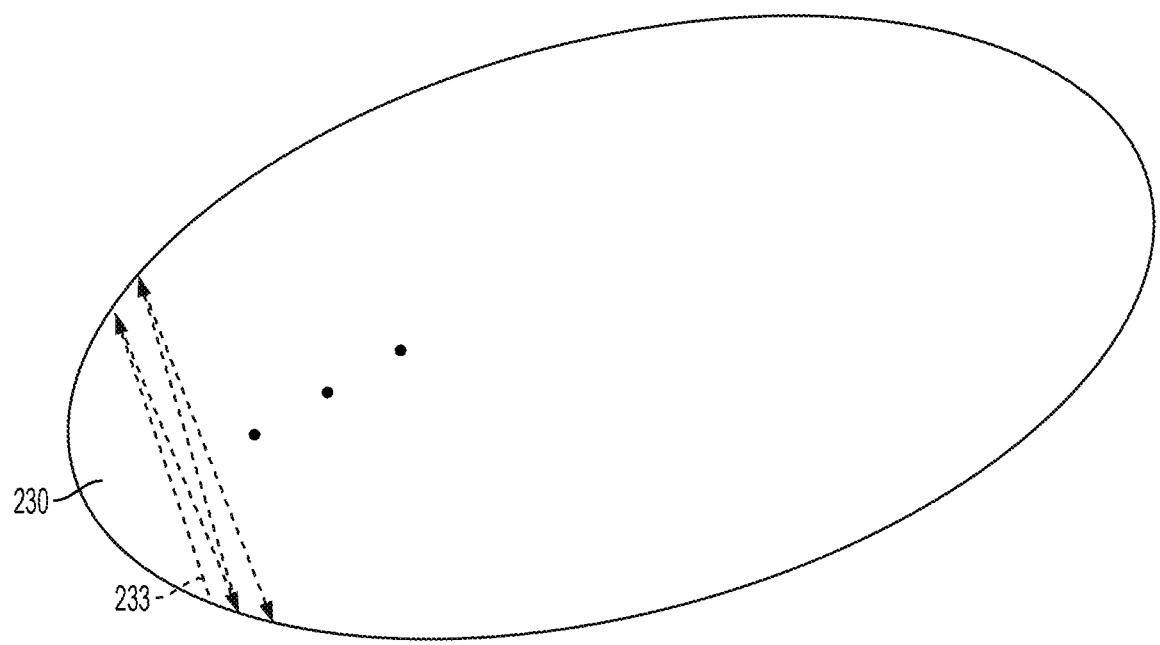
FIG. 18 is a top view show an example cross-section of an irradiation target and a radiation scan path.

An energy degrader may be set to select (202) a layer, and current may be applied to the magnet and controlled to move (203) the particle beam in accordance with a pattern set forth, e.g., in the treatment plan, to scan the layer. The current control may produce uninterrupted movement of the beam across at least part of the irradiation target to deliver doses of charged particles. An example of a pattern of beam movement 230 across a layer 233 of an irradiation target is shown in FIG. 18. As the beam moves, each pulse of the beam delivers a dose of radiation to the target. The dose has an intensity, which may be set beforehand in the accelerator or during scanning, and is delivered to specific positions. The exact positions at which dose is to be delivered need not be set beforehand, but rather may be arrived at by a combination of beam movement and pulse output.

For positions at which the dose is delivered, information is stored (204) (or otherwise recorded), which identifies a location and an amount of dose delivered at the location. This information is typically stored after the dose is delivered. As explained above, the information may be determined as close to delivery of the dose as possible, using the ion chamber to determine particle beam intensity (e.g., the amount of the dose) and the current sensor on the scanning magnet to determine the location at which the dose is delivered. As described above, in some implementations, in synchronism with the delivery, information identifying doses of the particle beam delivered to the irradiation target is stored along with at least one of: coordinates at which the doses were delivered or magnet currents at which the doses were delivered. As also described above, this information may be stored in tables, which may be used to store the cumulative dose of radiation applied at positions on various layers of an irradiation target.

The entire layer may be scanned and information therefor recorded, as described above, or only part of the layer may be scanned and information therefor recorded. The adaptive aperture is mounted on an appropriate location of the scanning system in such as manner as to enable the adaptive aperture to track the particle beam's movement during scanning operations. At a point during scanning, the cumulative dose delivered at each position is compared to a target cumulative dose for that position. For example, this may be done after part of a layer containing that position is scanned, after the entire layer is scanned, after a set of layers are scanned, or after all layers in an irradiation target are scanned. It is determined (205) if the current cumulative dose matches the target cumulative dose at specific positions. If the current cumulative dose does match the target cumulative dose at specific positions, scanning is completed (207) for those positions. If the current cumulative dose does not match the target cumulative dose at specific positions, the scanning system is operated to compensate for deficiencies in the recorded (e.g., current cumulative) doses relative to corresponding target cumulative doses for those positions. For example, if the current cumulative dose does not match the target cumulative dose at specific positions, the current in the scanning magnet may be controlled in order to move (206) the beam so as to deliver additional dose to the specific positions.

As explained above, in some implementations, 100% of the dose may be applied during a single scan (e.g., a single delivery of particles) of a layer. In that case, more than one scan per layer may not be necessary. In other implementations, less than 100% of the dose may be applied during a single scan. In that case, more than one scan per layer will be necessary. To this end, according to the scanning process, for positions at which dose is applied, if the current cumulative dose at each position does not match the target cumulative dose at a corresponding position, the magnet current is controlled in order to move the beam so as to deliver additional dose to positions that require more dose. In other words, the layer may be re-scanned any appropriate number of times until the target cumulative dose is reached for all positions of the layer. In some implementations, in one scan or in multiple scans, the actual delivered dose may exceed 100% of the target cumulative dose. What dose to deliver may be dictated by appropriate medical professionals.

As noted above, the layer may be re-scanned at any appropriate point, e.g., after part of the layer is completed with a current scan, after the entire layer is completed with the current scan, after a set of layers is completed with a scan, or after all layers are completed with a scan. During re-scanning, the process above is repeated until the target cumulative dose is reached for all, or some subset of, positions in the irradiation target. In some implementations, the intensity of the particle beam may need to be adjusted, e.g., for the last scan. For example, if the intensity is set at 25% of the target cumulative dose, but only 20% is delivered at each scan, then a fifth (and possibly sixth) dose will require a lower intensity than 25% in order to reach the target cumulative dose.

In some implementations, information from the TPP may be used to configure the adaptive aperture for an initial spot or series of spots. As described herein, configuring may include, for example, positioning carriages 713, 714, and/or 715, and/or one or more of leaves 735 and/or 736. In some implementations, the initial configuration may be made based on assumptions included in the treatment planning process including, but not limited to, the position of the irradiation target and patient during treatment. In some cases, however, the position of the irradiation target and patient during treatment may change relative to the assumptions included in the TPP. For example, the patient may move, breathing may impact target positions, and so forth. To account for these changes caused by movement, spot characteristics including, but not limited to, spot location, spot size, spot shape, spot weight, or spot orientation, may be correspondingly changed in order to implement the treatment. In some implementations, rather than modifying inputs to the TPP in order to make these changes via the TPP, the changes may be made online—e.g., during treatment while the accelerator is operational—without requiring any, or some, additional input from the TPP or the TPS.

For example, in some implementations, the position of the irradiation target may be tracked directly within the treatment room. For example, the treatment room may include one or more imaging systems to image and thereby track motion of the irradiation target. Examples of in-room imaging systems that may be used to track motion of an irradiation target are described in U.S. Patent Publication No. 2016/0067525, which was filed on Sep. 9, 2014, and which is titled "Patient Positioning System". U.S. Patent Publication No. 2016/0067525 is incorporated by reference, at least for its disclosure of systems used to locate, and track, motion of an irradiation target in a treatment room.

In some implementations, the imaging system can be a three-dimensional (3D) imaging system. In some implementations, the imaging system can be a two-dimensional (2D) imaging system. In some implementations, the imaging system may be, or include, one or more of the following types of imaging systems: a CT system, an X-ray device to capture a radiograph image, a magnetic resonance imaging (MRI) device to capture an MRI image, a positron emission tomography (PET) device to capture a PET image, a SPECT/CT device (where SPECT is Single-photon emission computed tomography), and/or a video surface imaging device, or any combination of these imaging devices. In some implementations, images may be captured at different points in time so as to enable tracking of movement of the irradiation target. In some implementations, fiducials associated the patient and proximate to an irradiation target may be used to detect motion of the patient and/or irradiation target. The location of the fiducials relative to the target may be known, and movement of the fiducials may be detected and correlated to movement of the irradiation target. In some implementations, the irradiation target may be imaged directly at two different points in time.

Figure 43:
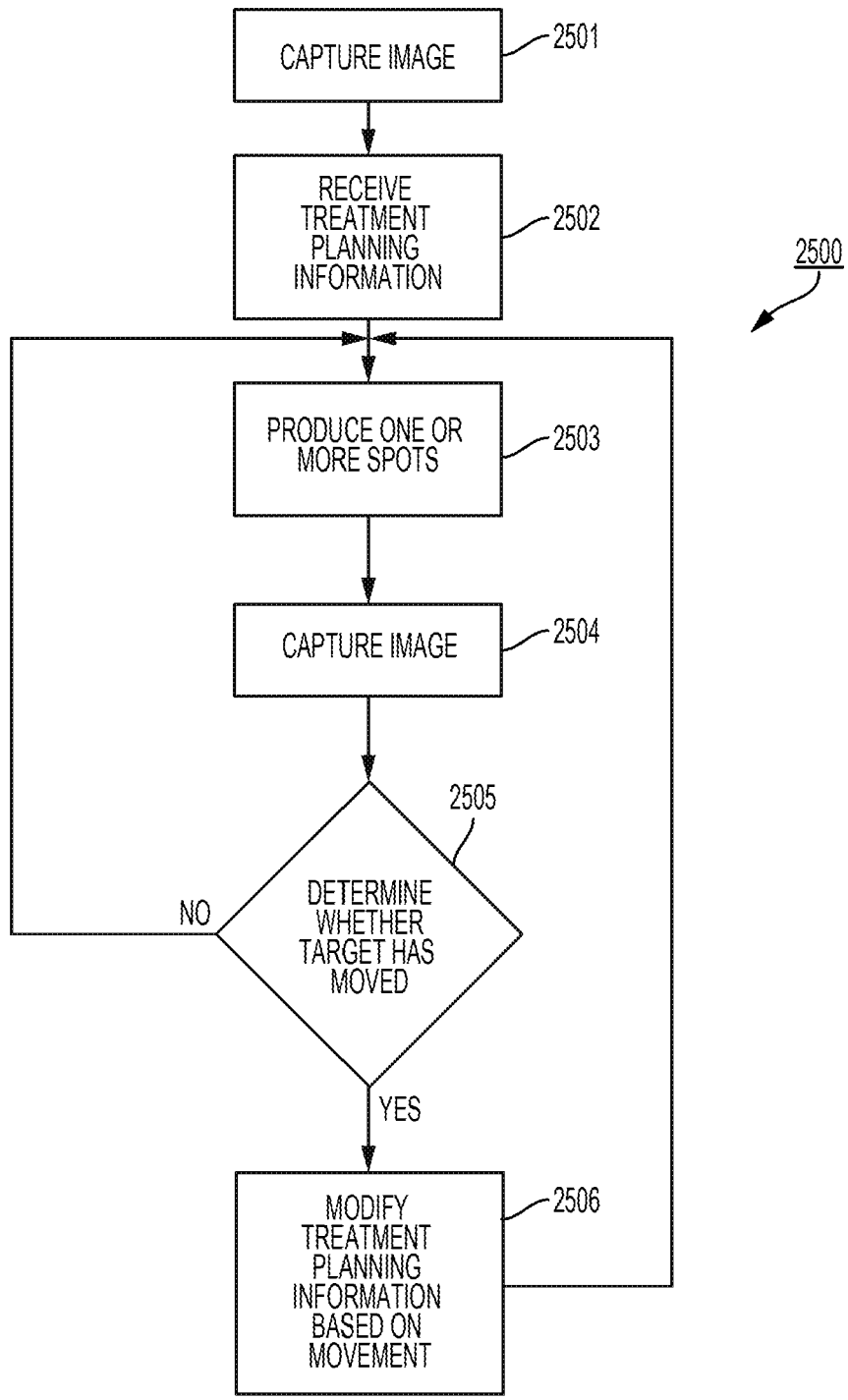
FIG. 43 is a flowchart showing an example process for configuring an adaptive aperture in response to movement of an irradiation target.

In some implementations, movement may be tracked between application of individual spots on a single layer, between application of sets of spots (e.g., a predefined number of spots) on a single layer, between layers, or between some appropriate combination of the foregoing. Referring to example process 2500 of FIG. 43, an image of an irradiation target or patient is captured (2501) in order to determine the location of the irradiation target. The particle therapy system receives (2502) information from a TPP/TPS that is used to produce (2503) a spot or set of spots on the irradiation target at appropriate locations based on the information. Thereafter, an image of an irradiation target or patient is captured (2504) in order to determine (2505) whether the irradiation target has moved since a prior image was captured. In some implementations, an X-ray system may be used to capture the image; however, any appropriate imaging system including, but not limited to, those described herein may be used. An irradiation target is deemed to have moved if the irradiation target is not in the same location, e.g., relative to some reference point, such as a fiducial, between images. If the irradiation target has not moved, one or more spots are produced (2503) using the most current treatment planning information. For example, the most current treatment planning information may be the information received (2502) from the TPP/TPS, or the most current treatment planning information may be the information as modified (2506) to account for prior movement. If the irradiation target has moved, the treatment planning information is modified (2506) to produce updated treatment planning information based on the movement of the irradiation target. Thereafter, spots are produced using the updated treatment planning information. The process may proceed as shown in FIG. 43 until the entire target is treated.

Thus, in some implementations, the TPP need not be re-run using new information, such as the newly-determined location of the irradiation target. Instead, in some implementations, the information from the TPP/TPS used to produce the spots is modified or changed (2506), e.g., in real-time, to account for the movement of the irradiation target. For example, the information may be changed while a particle accelerator, such as a synchrocyclotron, used to provide the treatment is online. Any appropriate information may be changed including, but not limited to, spot location, spot size, spot shape, spot weight, or spot orientation. For example, the locations of spots may be changed to account for movement of the irradiation target. In another example, the direction of application of particles to the irradiation target may be changed to account for movement of the irradiation target.

The processes described herein may be used with a single particle accelerator, and any two or more of the features thereof described herein may be used with the single particle accelerator. The particle accelerator may be used in any type of medical or non-medical application. Examples of particle therapy systems that may be used are provided below. Notably, the concepts described herein may be used in other systems not specifically described.

Figure 19:
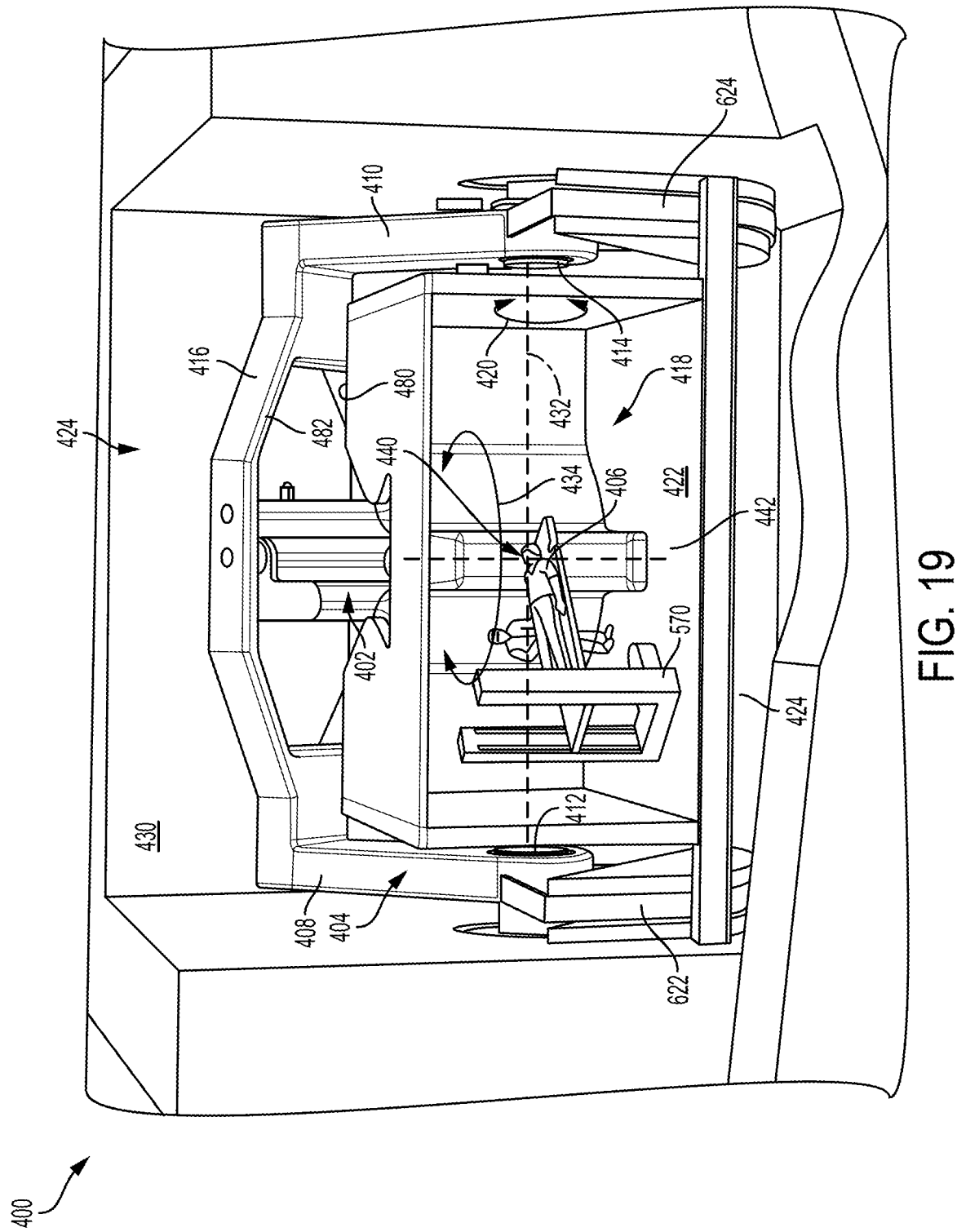
FIG. 19 is a perspective view of an example therapy system.
Figure 20:
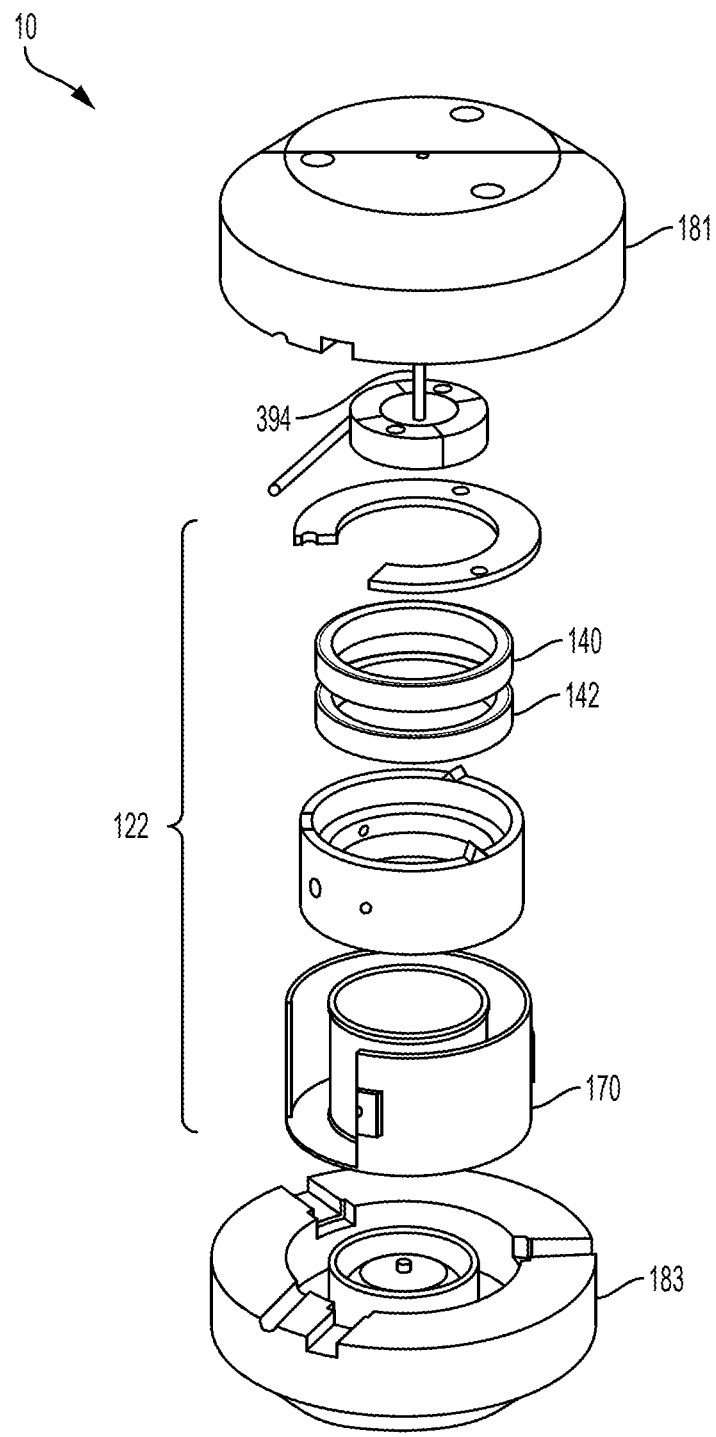
FIG. 20 is an exploded perspective view of components of an example synchrocyclotron for use in the particle therapy system.

Referring to FIG. 19, an example implementation of a charged particle radiation therapy system 400 includes a beam-producing particle accelerator 402 (e.g., the particle accelerator of FIGS. 8 and 9) having a weight and size small enough to permit it to be mounted on a rotating gantry 404 with its output directed straight (that is, essentially directly) from the accelerator housing toward a patient 406. Particle accelerator 402 also includes a scanning system of a type described herein (e.g., in FIGS. 10 to 18).

In some implementations, the steel gantry has two legs 408, 410 mounted for rotation on two respective bearings 412, 414 that lie on opposite sides of the patient. The accelerator is supported by a steel truss 416 that is long enough to span a treatment area 418 in which the patient lies (e.g., twice as long as a tall person, to permit the person to be rotated fully within the space with any desired target area of the patient remaining in the line of the beam) and is attached stably at both ends to the rotating legs of the gantry.

In some examples, the rotation of the gantry is limited to a range 420 of less than 360 degrees, e.g., about 180 degrees, to permit a floor 422 to extend from a wall of a vault 424 that houses the therapy system into the patient treatment area. The limited rotation range of the gantry also reduces the required thickness of some of the walls (which are not directly aligned with the beam, e.g., wall 430), which provide radiation shielding of people outside the treatment area. A range of 180 degrees of gantry rotation is enough to cover all treatment approach angles, but providing a larger range of travel can be useful. For example the range of rotation may be between 180 and 330 degrees and still provide clearance for the therapy floor space. In other implementations, rotation is not limited as described above.

The horizontal rotational axis 432 of the gantry is located nominally one meter above the floor where the patient and therapist interact with the therapy system. This floor is positioned about 3 meters above the bottom floor of the therapy system shielded vault. The accelerator can swing under the raised floor for delivery of treatment beams from below the rotational axis. The patient couch moves and rotates in a substantially horizontal plane parallel to the rotational axis of the gantry. The couch can rotate through a range 434 of about 270 degrees in the horizontal plane with this configuration. This combination of gantry and patient rotational ranges and degrees of freedom allows the therapist to select virtually any approach angle for the beam. If needed, the patient can be placed on the couch in the opposite orientation and then all possible angles can be used.

In some implementations, the accelerator uses a synchrocyclotron configuration having a high magnetic field superconducting electromagnetic structure. Because the bend radius of a charged particle of a given kinetic energy is reduced in direct proportion to an increase in the magnetic field applied to it, the high magnetic field superconducting magnetic structure permits the accelerator to be made smaller and lighter. The synchrocyclotron uses a magnetic field that is uniform in rotation angle and falls off in strength with increasing radius. Such a field shape can be achieved regardless of the magnitude of the magnetic field, so in theory there is no upper limit to the magnetic field strength (and therefore the resulting particle energy at a fixed radius) that can be used in a synchrocyclotron.

The synchrocyclotron is supported on the gantry so that the beam is generated directly in line with the patient. The gantry permits rotation of the synchrocyclotron about a horizontal rotational axis that contains a point (isocenter 440) within, or near, the patient. The split truss that is parallel to the rotational axis, supports the synchrocyclotron on both sides.

Because the rotational range of the gantry is limited in some example implementations, a patient support area can be accommodated in a wide area around the isocenter.

Because the floor can be extended broadly around the isocenter, a patient support table can be positioned to move relative to and to rotate about a vertical axis 442 through the isocenter so that, by a combination of gantry rotation and table motion and rotation, any angle of beam direction into any part of the patient can be achieved. In some implementations, the two gantry arms are separated by more than twice the height of a tall patient, allowing the couch with patient to rotate and translate in a horizontal plane above the raised floor.

Limiting the gantry rotation angle allows for a reduction in the thickness of at least one of the walls surrounding the treatment room. Thick walls, typically constructed of concrete, provide radiation protection to individuals outside the treatment room. A wall downstream of a stopping proton beam may be about twice as thick as a wall at the opposite end of the room to provide an equivalent level of protection. Limiting the range of gantry rotation enables the treatment room to be sited below earth grade on three sides, while allowing an occupied area adjacent to the thinnest wall reducing the cost of constructing the treatment room.

In the example implementation shown in FIG. 19, the superconducting synchrocyclotron 402 operates with a peak magnetic field in a pole gap of the synchrocyclotron of 8.8 Tesla. The synchrocyclotron produces a beam of protons having an energy of 250 MeV. In some implementations, the synchrocyclotron is a variable-energy machine, and is capable of outputting proton beams having different energies. In some implementations, the synchrocyclotron may produce a beam having a fixed energy. In some implementations the field strength could be in the range of 4 T to 20 T and the proton energy could be in the range of 100 to 300 MeV.

The radiation therapy system described in this example is used for proton radiation therapy, but the same principles and details can be applied in analogous systems for use in heavy ion (ion) treatment systems.

As shown in FIGS. 8, 9, 20, 21, and 22, an example synchrocyclotron 10 (e.g., 402 in FIG. 19) includes a magnet system 122 that contains a particle source 190, a radiofrequency drive system 191, and a beam extraction system. In this example, the magnetic field established by the magnet system has a shape appropriate to maintain focus of a contained proton beam using a combination of a split pair of annular superconducting coils 140, 142 and a pair of shaped ferromagnetic (e.g., low carbon steel) pole faces 144, 146.

The two superconducting magnet coils are centered on a common axis and are spaced apart along the axis. The coils may be formed by of $Nb_3Sn$-based superconducting strands (that initially comprise a niobium-tin core surrounded by a copper sheath) deployed in a twisted cable-in-channel conductor geometry. After individual strands are cabled together, they are heated to cause a reaction that forms the final (brittle) superconducting material of the wire. After the material has been reacted, the wires are soldered into the copper channel and covered with insulation. The copper channel containing the wires is then wound in a coil having a rectangular cross-section. The wound coil is then vacuum impregnated with an epoxy compound. The finished coils are mounted on an annular stainless steel reverse bobbin. Heater blankets may be placed at intervals in the layers of the windings to protect the assembly in the event of a magnet quench.

The entire coil can then be covered with copper sheets to provide thermal conductivity and mechanical stability and then contained in an additional layer of epoxy. The precompression of the coil can be provided by heating the stainless steel reverse bobbin and fitting the coils within the reverse bobbin. The reverse bobbin inner diameter is chosen so that when the entire mass is cooled to 4 K, the reverse bobbin stays in contact with the coil and provides some compression. Heating the stainless steel reverse bobbin to approximately 50 degrees C. and fitting coils at a temperature of 100 degrees Kelvin can achieve this.

Figure 21:
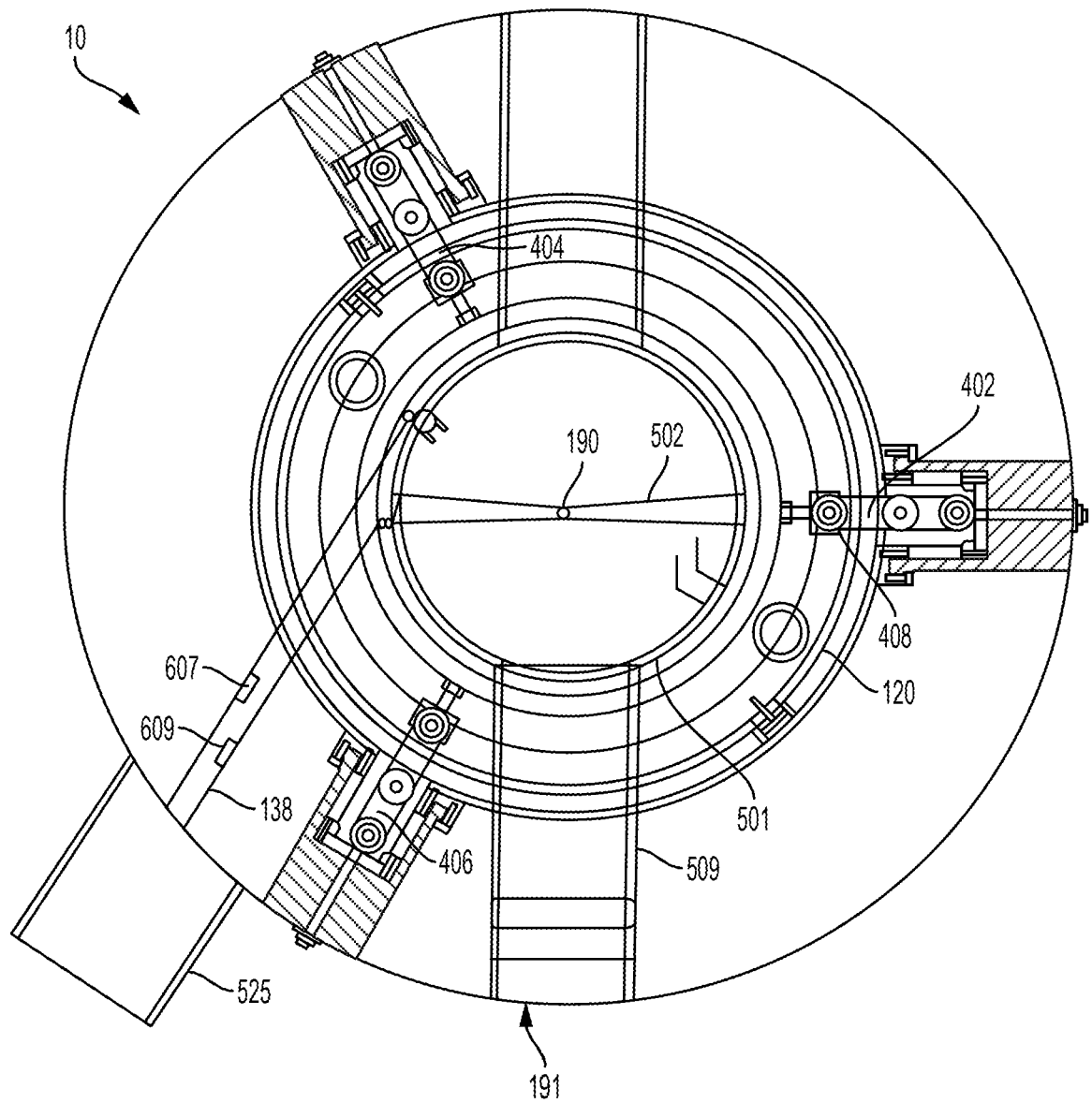
FIG. 21 is a cross-sectional, top view of the example synchrocyclotron.
Figure 22:
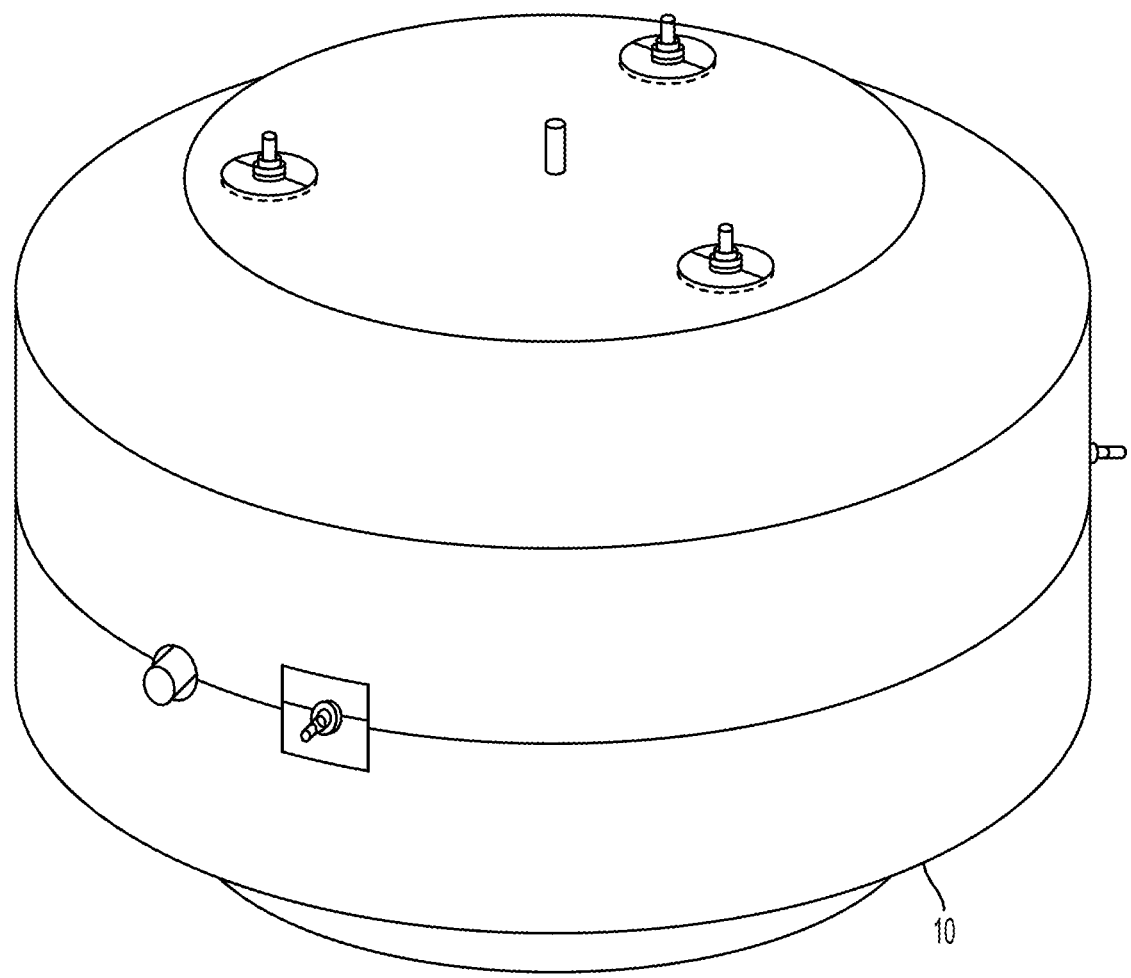
FIG. 22 is a perspective view of the example synchrocyclotron.

The geometry of the coil is maintained by mounting the coils in a "reverse" rectangular bobbin to exert a restorative force that works against the distorting force produced when the coils are energized. As shown in FIG. 21, in some implementations, coil position is maintained relative to corresponding magnet pole pieces and the cryostat using a set of warm-to-cold support straps 402, 404, 406. Supporting the cold mass with thin straps reduces the heat leakage imparted to the cold mass by the rigid support system. The straps are arranged to withstand the varying gravitational force on the coil as the magnet rotates on board the gantry. They withstand the combined effects of gravity and the large de-centering force realized by the coil when it is perturbed from a perfectly symmetric position relative to the magnet yoke. Additionally, the links act to reduce dynamic forces imparted on the coil as the gantry accelerates and decelerates when its position is changed. Each warm-to-cold support may include one S2 fiberglass link and one carbon fiber link. The carbon fiber link is supported across pins between the warm yoke and an intermediate temperature (50-70 K), and the S2 fiberglass link 408 is supported across the intermediate temperature pin and a pin attached to the cold mass. Each pin may be made of high strength stainless steel.

Referring to FIG. 8, the field strength profile as a function of radius is determined largely by choice of coil geometry and pole face shape. The pole faces 144, 146 of the permeable yoke material can be contoured to fine tune the shape of the magnetic field to ensure that the particle beam remains focused during acceleration.

The superconducting coils are maintained at temperatures near absolute zero (e.g., about 4 degrees Kelvin) by enclosing the coil assembly (the coils and the bobbin) inside an evacuated annular aluminum or stainless steel cryostatic chamber 170 (the cryostat) that provides a free space around the coil structure, except at a limited set of support points 171, 173. In an alternate version (e.g., FIG. 9) the outer wall of the cryostat may be made of low carbon steel to provide an additional return flux path for the magnetic field.

In some implementations, the temperature near absolute zero is achieved and maintained using one single-stage Gifford-McMahon cryo-cooler and three two-stage Gifford McMahon cryo-coolers. Each two stage cryo-cooler has a second stage cold end attached to a condenser that recondenses Helium vapor into liquid Helium. In some implementations, the temperature near absolute zero is achieved and maintained using a cooling channel (not shown) containing liquid helium, which is formed inside a superconducting coil support structure (e.g., the reverse bobbin 156), and which contains a thermal connection between the liquid helium in the channel and the corresponding superconducting coil.

In some implementations, the coil assembly and cryostatic chambers are mounted within and fully enclosed by two halves 181, 183 of a pillbox-shaped magnet yoke 100. The yoke 100 provides a path for the return magnetic field flux 184 and magnetically shields the volume 186 between the pole faces 144, 146 to prevent external magnetic influences from perturbing the shape of the magnetic field within that volume. The yoke also serves to decrease the stray magnetic field in the vicinity of the accelerator. In other implementations, the coil assembly and cryostatic chambers are mounted within and fully enclosed by a non-magnetic enclosure, and the path for return magnetic field flux is implemented using an active return system, an example of which is described above.

Figure 23:
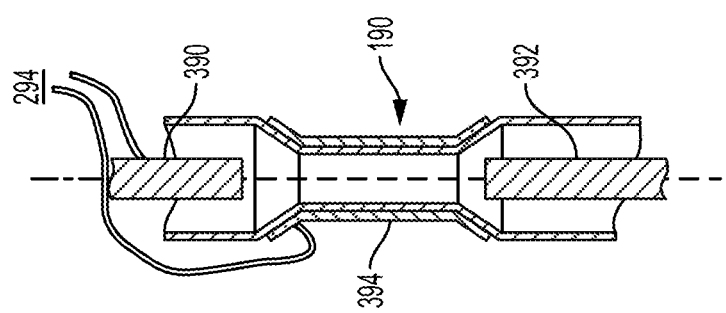
FIG. 23 is a cross-sectional view of an example ion source for use in the synchrocyclotron.

As shown in FIGS. 8 and 23, the synchrocyclotron includes a particle source 190 of a Penning ion gauge geometry located near the geometric center 192 of the magnet structure. The particle source may be as described below.

Particle source 190 is fed from a supply 399 of hydrogen through a gas line 393 and tube 394 that delivers gaseous hydrogen. Electric cables 294 carry an electric current from a current source to stimulate electron discharge from cathodes 392, 390 that are aligned with the magnetic field. Particle source may be interrupted at the acceleration plane, e.g., the entirety of the particle source may be removed, thereby exposing the plasma column.

In this example, the discharged electrons ionize the gas exiting through a small hole from tube 394 to create a supply of positive ions (protons) for acceleration by one semicircular (dee-shaped) radio-frequency plate that spans half of the space enclosed by the magnet structure and one dummy dee plate. In the case of an interrupted particle source, all (or a substantial part, e.g., a majority) of the tube containing plasma is removed at the acceleration region.

Figure 24:
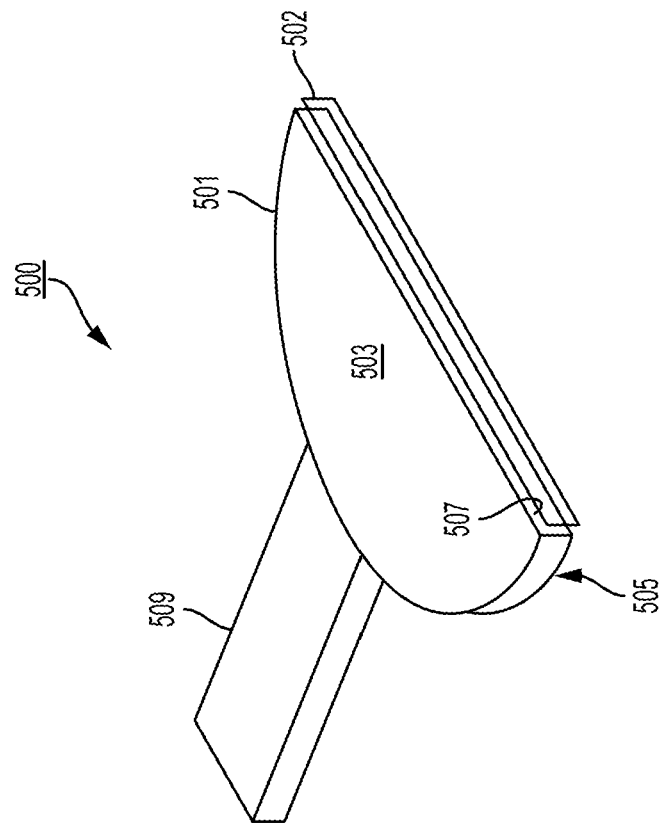
FIG. 24 is a perspective view of an example dee leaf and an example dummy dee for use in the synchrocyclotron.

As shown in FIG. 24, the dee plate 500 is a hollow metal structure that has two semicircular surfaces 503, 505 that enclose a space 507 in which the protons are accelerated during half of their rotation around the space enclosed by the magnet structure. A duct 509 opening into the space 507 extends through the enclosure (e.g., the yoke or pole piece (s)) to an external location from which a vacuum pump can be attached to evacuate the space 507 and the rest of the space within a vacuum chamber in which the acceleration takes place. The dummy dee 502 comprises a rectangular metal ring that is spaced near to the exposed rim of the dee plate. The dummy dee is grounded to the vacuum chamber and magnet yoke. The dee plate 500 is driven by a radio-frequency signal that is applied at the end of a radio-frequency transmission line to impart an electric field in the space 507. The radio frequency electric field is made to vary in time as the accelerated particle beam increases in distance from the geometric center.

For the beam emerging from the centrally located particle source to clear the particle source structure as it begins to spiral outward, a large voltage difference may be applied across the radio frequency plates. 20,000 Volts is applied across the radio frequency plates. In some versions from 8,000 to 20,000 Volts may be applied across the radio frequency plates. To reduce the power required to drive this large voltage, the magnet structure is arranged to reduce the capacitance between the radio frequency plates and ground. This may be done by forming holes with sufficient clearance from the radio frequency structures through the outer yoke and the cryostat housing and making sufficient space between the magnet pole faces.

The high voltage alternating potential that drives the dee plate has a frequency that is swept downward during the accelerating cycle to account for the increasing relativistic mass of the protons and the decreasing magnetic field. The dummy dee does not require a hollow semi-cylindrical structure as it is at ground potential along with the vacuum chamber walls. Other plate arrangements could be used such as more than one pair of accelerating electrodes driven with different electrical phases or multiples of the fundamental frequency. The RF structure can be tuned to keep the Q high during the required frequency sweep by using, for example, a rotating capacitor having intermeshing rotating and stationary blades. During each meshing of the blades, the capacitance increases, thus lowering the resonant frequency of the RF structure. The blades can be shaped to create a precise frequency sweep required. A drive motor for the rotating condenser can be phase locked to the RF generator for precise control. One bunch of particles may be accelerated during each meshing of the blades of the rotating condenser.

The vacuum chamber in which the acceleration occurs is a generally cylindrical container that is thinner in the center and thicker at the rim. The vacuum chamber encloses the RF plates and the particle source and is evacuated by a vacuum pump. Maintaining a high vacuum reduces the chances that accelerating ions are not lost to collisions with gas molecules and enables the RF voltage to be kept at a higher level without arcing to ground.

Protons (or other ions) traverse a generally spiral orbital path beginning at the particle source. In half of each loop of the spiral path, the protons gain energy as they pass through the RF electric field. As the protons gain energy, the radius of the central orbit of each successive loop of their spiral path is larger than the prior loop until the loop radius reaches the maximum radius of the pole face. At that location a magnetic and electric field perturbation directs protons into an area where the magnetic field rapidly decreases, and the protons depart the area of the high magnetic field and are directed through an evacuated tube, referred to herein as the extraction channel, to exit the synchrocyclotron. A magnetic regenerator may be used to change the magnetic field perturbation to direct the protons. The protons exiting will tend to disperse as they enter an area of markedly decreased magnetic field that exists in the room around the synchrocyclotron. Beam shaping elements 607, 609 in the extraction channel 138 (FIG. 21) redirect the protons so that they stay in a straight beam of limited spatial extent.

As the beam exits the extraction channel it is passed through a beam formation system 525 (FIG. 21), which may include a scanning system of the type described herein. Beam formation system 525 may be used in conjunction with an inner gantry that controls application of the beam.

Stray magnetic fields exiting from the synchrocyclotron may be limited by both a magnet yoke (which also serves as a shield) and a separate magnetic shield 514 (e.g., FIG. 8). The separate magnetic shield includes of a layer 517 of ferromagnetic material (e.g., steel or iron) that encloses the pillbox yoke, separated by a space 516. This configuration that includes a sandwich of a yoke, a space, and a shield achieves adequate shielding for a given leakage magnetic field at lower weight. As described above, in some implementations, an active return system may be used in place of, or to augment, the operation of the magnetic yoke and shield.

Referring to FIG. 19, the gantry allows the synchrocyclotron to be rotated about a horizontal rotational axis 432. The truss structure 416 has two generally parallel spans 480, 482. The synchrocyclotron is cradled between the spans about midway between the legs. The gantry is balanced for rotation about the bearings using counterweights 622, 624 mounted on ends of the legs opposite the truss.

The gantry is driven to rotate by an electric motor mounted to one or both of the gantry legs and connected to the bearing housings by drive gears. The rotational position of the gantry is derived from signals provided by shaft angle encoders incorporated into the gantry drive motors and the drive gears.

At the location at which the ion beam exits the synchrocyclotron, the beam formation system 525 acts on the ion beam to give it properties suitable for patient treatment. For example, the beam may be spread and its depth of penetration varied to provide uniform radiation across a given target volume. The beam formation system may include active scanning elements as described herein.

All of the active systems of the synchrocyclotron (the current driven superconducting coils, the RF-driven plates, the vacuum pumps for the vacuum acceleration chamber and for the superconducting coil cooling chamber, the current driven particle source, the hydrogen gas source, and the RF plate coolers, for example), may be controlled by appropriate synchrocyclotron control electronics (not shown), which may include, e.g., one or more processing devices executing instructions from non-transitory memory to effect control.

Figure 25:
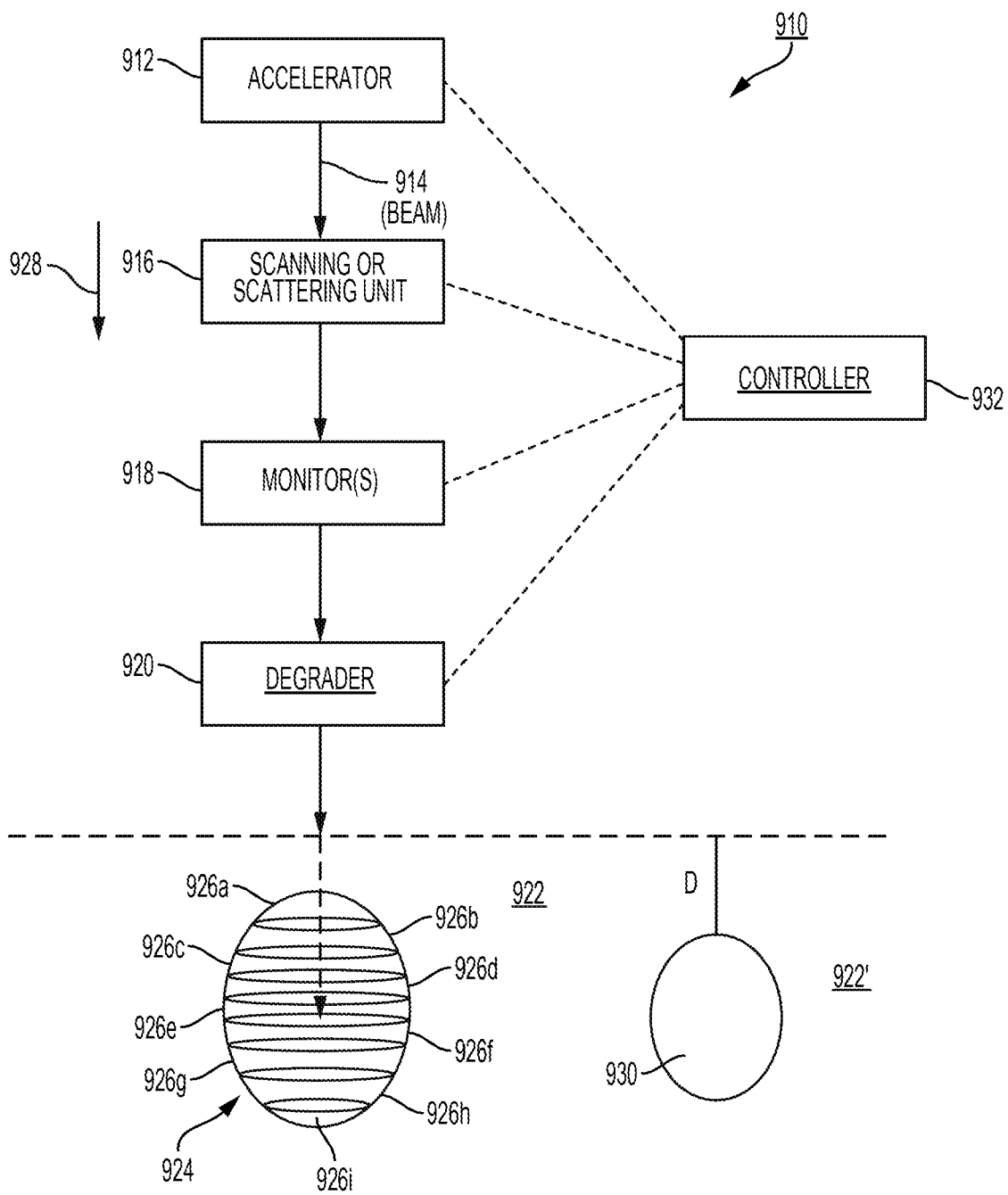
FIG. 25 is a conceptual view of an example particle therapy system that may use a variable-energy particle accelerator.

The particle accelerator used in the example particle therapy systems and example scanning systems described herein may be a variable-energy particle accelerator, an example of which is described below The energy of an extracted particle beam (the particle beam output from the accelerator) can affect the use of the particle beam during treatment. In some machines, the energy of the particle beam (or particles in the particle beam) does not increase after extraction. However, the energy may be reduced based on treatment needs after the extraction and before the treatment. Referring to FIG. 25, an example treatment system 910 includes an accelerator 912, e.g., a synchrocyclotron, from which a particle (e.g., proton) beam 914 having a variable energy is extracted to irradiate a target volume 924 of a body 922. Optionally, one or more additional devices, such as a scanning unit 916 or a scattering unit 916, one or more monitoring units 918, and an energy degrader 920, are placed along the irradiation direction 928. The devices intercept the cross-section of the extracted beam 914 and alter one or more properties of the extracted beam for the treatment. The adaptive aperture may be located down-beam of the energy degrader, between the energy degrader and the patient.

A target volume to be irradiated (an irradiation target) by a particle beam for treatment typically has a three-dimensional configuration. In some examples, to carry-out the treatment, the target volume is divided into layers along the irradiation direction of the particle beam so that the irradiation can be done on a layer-by-layer basis. For certain types of particles, such as protons, the penetration depth (or which layer the beam reaches) within the target volume is largely determined by the energy of the particle beam. A particle beam of a given energy does not reach substantially beyond a corresponding penetration depth for that energy. To move the beam irradiation from one layer to another layer of the target volume, the energy of the particle beam is changed.

In the example shown in FIG. 25, the target volume 924 is divided into nine layers 926a-926i along the irradiation direction 928. In an example process, the irradiation starts from the deepest layer 926i, one layer at a time, gradually to the shallower layers and finishes with the shallowest layer 926a. Before application to the body 922, the energy of the particle beam 914 is controlled to be at a level to allow the particle beam to stop at a desired layer, e.g., the layer 926d, without substantially penetrating further into the body or the target volume, e.g., the layers 926e-926i or deeper into the body. In some examples, the desired energy of the particle beam 914 decreases as the treatment layer becomes shallower relative to the particle acceleration. In some examples, the beam energy difference for treating adjacent layers of the target volume 924 is about 3 MeV to about 100 MeV, e.g., about 10 MeV to about 80 MeV, although other differences may also be possible, depending on, e.g., the thickness of the layers and the properties of the beam.

The energy variation for treating different layers of the target volume 924 can be performed at the accelerator 912 (e.g., the accelerator can vary the energy) so that, in some implementations, no additional energy variation is required after the particle beam is extracted from the accelerator 912. So, the optional energy degrader 920 in the treatment system 10 may be eliminated from the system. In some implementations, the accelerator 912 can output particle beams having an energy that varies between about 100 MeV and about 300 MeV, e.g., between about 115 MeV and about 250 MeV. The variation can be continuous or non-continuous, e.g., one step at a time. In some implementations, the variation, continuous or non-continuous, can take place at a relatively high rate, e.g., up to about 50 MeV per second or up to about 20 MeV per second. Non-continuous variation can take place one step at a time with a step size of about 10 MeV to about 90 MeV.

When irradiation is complete in one layer, the accelerator 912 can vary the energy of the particle beam for irradiating a next layer, e.g., within several seconds or within less than one second. In some implementations, the treatment of the target volume 924 can be continued without substantial interruption or even without any interruption. In some situations, the step size of the non-continuous energy variation is selected to correspond to the energy difference needed for irradiating two adjacent layers of the target volume 924. For example, the step size can be the same as, or a fraction of, the energy difference.

In some implementations, the accelerator 912 and the degrader 920 collectively vary the energy of the beam 914. For example, the accelerator 912 provides a coarse adjustment and the degrader 920 provides a fine adjustment or vice versa. In this example, the accelerator 912 can output the particle beam that varies energy with a variation step of about 10-80 MeV, and the degrader 920 adjusts (e.g., reduces) the energy of the beam at a variation step of about 2-10 MeV.

The reduced use (or absence) of the energy degrader, such as a range modulator, may help to maintain properties and quality of the output beam from the accelerator, e.g., beam intensity. The control of the particle beam can be performed at the accelerator. Side effects, e.g., from neutrons generated when the particle beam passes the degrader 920 can be reduced or eliminated.

The energy of the particle beam 914 may be adjusted to treat another target volume 930 in another body or body part 922' after completing treatment in target volume 924. The target volumes 924, 930 may be in the same body (or patient), or in different patients. It is possible that the depth D of the target volume 930 from a surface of body 922' is different from that of the target volume 924. Although some energy adjustment may be performed by the degrader 920, the degrader 912 may only reduce the beam energy and not increase the beam energy.

In this regard, in some cases, the beam energy required for treating target volume 930 is greater than the beam energy required to treat target volume 924. In such cases, the accelerator 912 may increase the output beam energy after treating the target volume 924 and before treating the target volume 930. In other cases, the beam energy required for treating target volume 930 is less than the beam energy required to treat target volume 924. Although the degrader 920 can reduce the energy, the accelerator 912 can be adjusted to output a lower beam energy to reduce or eliminate the use of the degrader 920. The division of the target volumes 924, 930 into layers can be different or the same. The target volume 930 can be treated similarly on a layer by layer basis to the treatment of the target volume 924.

The treatment of the different target volumes 924, 930 on the same patient may be substantially continuous, e.g., with the stop time between the two volumes being no longer than about 30 minutes or less, e.g., 25 minutes or less, 20 minutes or less, 15 minutes or less, 10 minutes or less, 5 minutes or less, or 1 minute or less. As explained herein, the accelerator 912 can be mounted on a movable gantry and the movement of the gantry can move the accelerator to aim at different target volumes. In some situations, the accelerator 912 can complete the energy adjustment of the output beam 914 during the time the treatment system makes adjustment (such as moving the gantry) after completing the treatment of the target volume 924 and before starting treating the target volume 930. After the alignment of the accelerator and the target volume 930, the treatment can begin with the adjusted, desired beam energy. Beam energy adjustment for different patients can also be completed relatively efficiently. In some examples, all adjustments, including increasing/reducing beam energy and/or moving the gantry are done within about 30 minutes, e.g., within about 25 minutes, within about 20 minutes, within about 15 minutes, within about 10 minutes or within about 5 minutes.

In the same layer of a target volume, an irradiation dose may be applied by moving the beam across the two-dimensional surface of the layer (which is sometimes called scanning beam) using a scanning unit 916. Alternatively, the layer can be irradiated by passing the extracted beam through one or more scatterers of the scattering unit 16 (which is sometimes called scattering beam).

Beam properties, such as energy and intensity, can be selected before a treatment or can be adjusted during the treatment by controlling the accelerator 912 and/or other devices, such as the scanning unit/scatterer(s) 916, the degrader 920, and others not shown in the figures. In example implementations, system 910 includes a controller 932, such as a computer, in communication with one or more devices in the system. Control can be based on results of the monitoring performed by the one or more monitors 918, e.g., monitoring of the beam intensity, dose, beam location in the target volume, etc. Although the monitors 918 are shown to be between the device 916 and the degrader 920, one or more monitors can be placed at other appropriate locations along the beam irradiation path. Controller 932 can also store a treatment plan for one or more target volumes (for the same patient and/or different patients). The treatment plan can be determined before the treatment starts and can include parameters, such as the shape of the target volume, the number of irradiation layers, the irradiation dose for each layer, the number of times each layer is irradiated, etc. The adjustment of a beam property within the system 910 can be performed based on the treatment plan. Additional adjustment can be made during the treatment, e.g., when deviation from the treatment plan is detected.

In some implementations, the accelerator 912 is configured to vary the energy of the output particle beam by varying the magnetic field in which the particle beam is accelerated. In an example implementation, one or more sets of coils receives variable electrical current to produce a variable magnetic field in the cavity. In some examples, one set of coils receives a fixed electrical current, while one or more other sets of coils receives a variable current so that the total current received by the coil sets varies. In some implementations, all sets of coils are superconducting. In other implementations, some sets of coils, such as the set for the fixed electrical current, are superconducting, while other sets of coils, such as the one or more sets for the variable current, are non-superconducting. In some examples, all sets of coils are non-superconducting.

Generally, the magnitude of the magnetic field is scalable with the magnitude of the electrical current. Adjusting the total electric current of the coils in a predetermined range can generate a magnetic field that varies in a corresponding, predetermined range. In some examples, a continuous adjustment of the electrical current can lead to a continuous variation of the magnetic field and a continuous variation of the output beam energy. Alternatively, when the electrical current applied to the coils is adjusted in a non-continuous, step-wise manner, the magnetic field and the output beam energy also varies accordingly in a non-continuous (step-wise) manner. The scaling of the magnetic field to the current can allow the variation of the beam energy to be carried out relatively precisely, although sometimes minor adjustment other than the input current may be performed.

In some implementations, to output particle beams having a variable energy, the accelerator 912 is configured to apply RF voltages that sweep over different ranges of frequencies, with each range corresponding to a different output beam energy. For example, if the accelerator 912 is configured to produce three different output beam energies, the RF voltage is capable of sweeping over three different ranges of frequencies. In another example, corresponding to continuous beam energy variations, the RF voltage sweeps over frequency ranges that continuously change. The different frequency ranges may have different lower frequency and/or upper frequency boundaries.

The extraction channel may be configured to accommodate the range of different energies produced by the variable-energy particle accelerator. For example the extraction channel may be large enough to support the highest and lowest energies produced by the particle accelerator. That is, the extraction channel may be sized or otherwise configured to receive and to transmit particles within that range of energies. Particle beams having different energies can be extracted from the accelerator 912 without altering the features of the regenerator that is used for extracting particle beams having a single energy. In other implementations, to accommodate the variable particle energy, the regenerator can be moved to disturb (e.g., change) different particle orbits in the manner described above and/or iron rods (magnetic shims) can be added or removed to change the magnetic field bump provided by the regenerator. More specifically, different particle energies will typically be at different particle orbits within the cavity. By moving the regenerator, it is possible to intercept a particle orbit at a specified energy and thereby provide the correct perturbation of that orbit so that particles at the specified energy reach the extraction channel. In some implementations, movement of the regenerator (and/or addition/removal of magnetic shims) is performed in real-time to match real-time changes in the particle beam energy output by the accelerator. In other implementations, particle energy is adjusted on a per-treatment basis, and movement of the regenerator (and/or addition/removal of magnetic shims) is performed in advance of the treatment. In either case, movement of the regenerator (and/or addition/removal of magnetic shims) may be computer controlled. For example, a computer may control one or more motors that effect movement of the regenerator and/or magnetic shims.

In some implementations, the regenerator is implemented using one or more magnetic shims that are controllable to move to the appropriate location(s).

As an example, table 1 shows three example energy levels at which example accelerator 912 can output particle beams. The corresponding parameters for producing the three energy levels are also listed. In this regard, the magnet current refers to the total electrical current applied to the one or more coil sets in the accelerator 912; the maximum and minimum frequencies define the ranges in which the RF voltage sweeps; and "r" is the radial distance of a location to a center of the cavity in which the particles are accelerated.

TABLE 1

Examples of beam energies and respective parameters.

| Beam Energy (MeV) | Magnet Current (Amps) | Maximum Frequency (MHz) | Minimum Frequency (MHz) | Magnetic Field at r = 0 mm (Tesla) | Magnetic Field at r = 298 mm (Tesla) |
|---|---|---|---|---|---|
| 250 | 1990 | 132 | 99 | 8.7 | 8.2 |
| 235 | 1920 | 128 | 97 | 8.4 | 8.0 |
| 211 | 1760 | 120 | 93 | 7.9 | 7.5 |

The accelerator may be a synchrocyclotron and the particles may be protons. The particles may be output as pulsed beams. The energy of the beam output from the particle accelerator can be varied during the treatment of one target volume in a patient, or between treatments of different target volumes of the same patient or different patients. In some implementations, settings of the accelerator are changed to vary the beam energy when no beam (or particles) is output from the accelerator. The energy variation can be continuous or non-continuous over a desired range.

Referring to the example shown in FIG. 8, the particle accelerator, which may be a variable-energy particle accelerator like accelerator 912 described above, may be configured to output particle beams that have a variable energy. The range of the variable energy can have an upper boundary that is about 200 MeV to about 300 MeV or higher, e.g., 200 MeV, about 205 MeV, about 210 MeV, about 215 MeV, about 220 MeV, about 225 MeV, about 230 MeV, about 235 MeV, about 240 MeV, about 245 MeV, about 250 MeV, about 255 MeV, about 260 MeV, about 265 MeV, about 270 MeV, about 275 MeV, about 280 MeV, about 285 MeV, about 290 MeV, about 295 MeV, or about 300 MeV or higher. The range can also have a lower boundary that is about 100 MeV or lower to about 200 MeV, e.g., about 100 MeV or lower, about 105 MeV, about 110 MeV, about 115 MeV, about 120 MeV, about 125 MeV, about 130 MeV, about 135 MeV, about 140 MeV, about 145 MeV, about 150 MeV, about 155 MeV, about 160 MeV, about 165 MeV, about 170 MeV, about 175 MeV, about 180 MeV, about 185 MeV, about 190 MeV, about 195 MeV, about 200 MeV.

In some examples, the variation is non-continuous and the variation step can have a size of about 10 MeV or lower, about 15 MeV, about 20 MeV, about 25 MeV, about 30 MeV, about 35 MeV, about 40 MeV, about 45 MeV, about 50 MeV, about 55 MeV, about 60 MeV, about 65 MeV, about 70 MeV, about 75 MeV, or about 80 MeV or higher. Varying the energy by one step size can take no more than 30 minutes, e.g., about 25 minutes or less, about 20 minutes or less, about 15 minutes or less, about 10 minutes or less, about 5 minutes or less, about 1 minute or less, or about 30 seconds or less. In other examples, the variation is continuous and the accelerator can adjust the energy of the particle beam at a relatively high rate, e.g., up to about 50 MeV per second, up to about 45 MeV per second, up to about 40 MeV per second, up to about 35 MeV per second, up to about 30 MeV per second, up to about 25 MeV per second, up to about 20 MeV per second, up to about 15 MeV per second, or up to about 10 MeV per second. The accelerator can be configured to adjust the particle energy both continuously and non-continuously. For example, a combination of the continuous and non-continuous variation can be used in a treatment of one target volume or in treatments of different target volumes. Flexible treatment planning and flexible treatment can be achieved.

A particle accelerator that outputs a particle beam having a variable energy can provide accuracy in irradiation treatment and reduce the number of additional devices (other than the accelerator) used for the treatment. For example, the use of degraders for changing the energy of an output particle beam may be reduced or eliminated for all or part of the treatment. The properties of the particle beam, such as intensity, focus, etc. can be controlled at the particle accelerator and the particle beam can reach the target volume without substantial disturbance from the additional devices. The relatively high variation rate of the beam energy can reduce treatment time and allow for efficient use of the treatment system.

Figure 26:
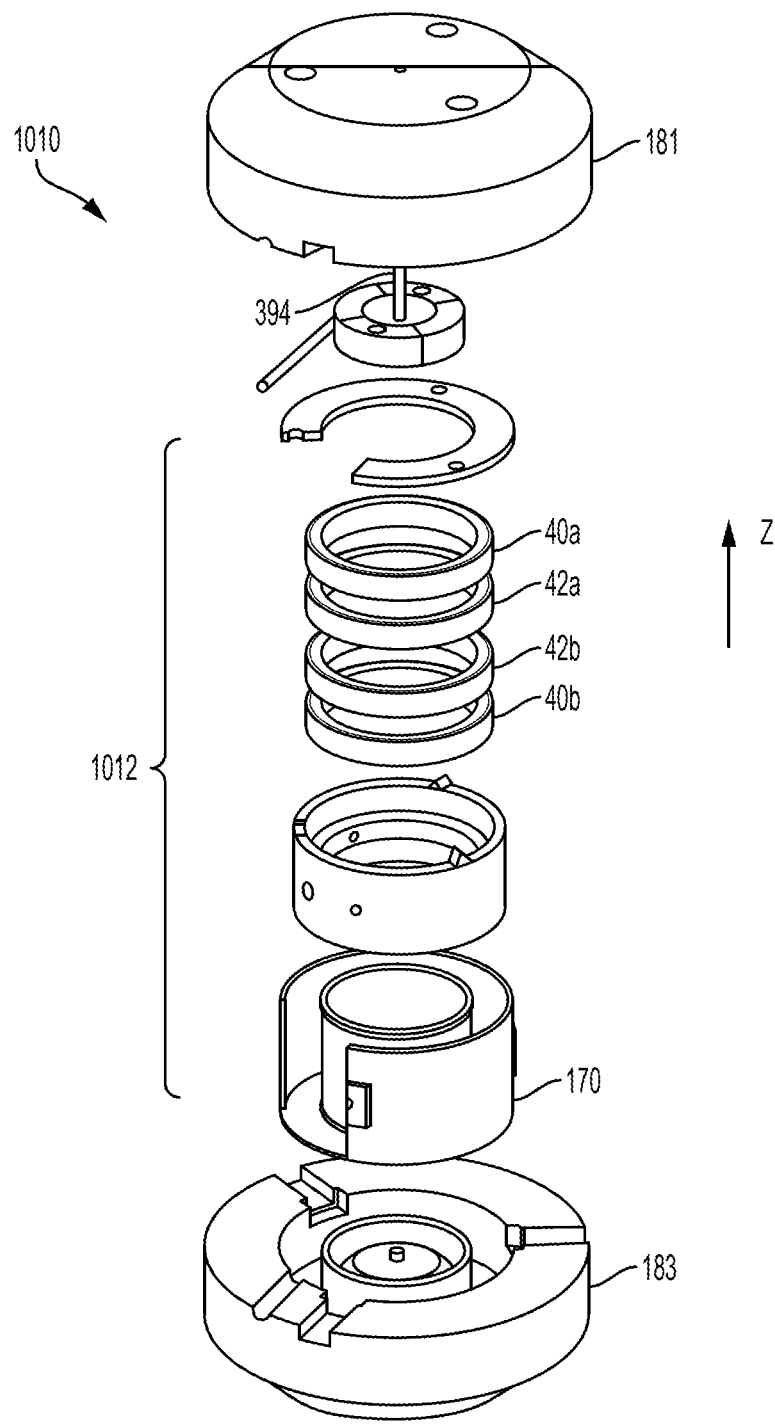
FIG. 26 is a perspective, exploded view of an example magnet system that may be used in a variable-energy particle accelerator.

In some implementations, the accelerator, such as the synchrocyclotron of FIG. 8, accelerates particles or particle beams to variable energy levels by varying the magnetic field in the accelerator, which can be achieved by varying the electrical current applied to coils for generating the magnetic field. As explained above, an example synchrocyclotron (e.g., the synchrocyclotron of FIG. 8) includes a magnet system that contains a particle source, a radiofrequency drive system, and a beam extraction system. FIG. 26 shows an example of a magnet system that may be used in a variable-energy accelerator. In this example implementation, the magnetic field established by the magnet system 1012 can vary by about 5% to about 35% of a maximum value of the magnetic field that two sets of coils 40a and 40b, and 42a and 42b are capable of generating. The magnetic field established by the magnet system has a shape appropriate to maintain focus of a contained proton beam using a combination of the two sets of coils and a pair of shaped ferromagnetic (e.g., low carbon steel) structures, examples of which are provided above.

Each set of coils may be a split pair of annular coils to receive electrical current. In some situations, both sets of coils are superconducting. In other situations, only one set of the coils is superconducting and the other set is non-superconducting or normal conducting (also discussed further below). It is also possible that both sets of coils are non-superconducting. Suitable superconducting materials for use in the coils include niobium-3 tin ($Nb_3Sn$) and/or niobium-titanium. Other example conducting materials can include copper. Examples of the coil set constructions are described further below.

The two sets of coils can be electrically connected serially or in parallel. In some implementations, the total electrical current received by the two sets of coils can include about 2 million ampere turns to about 10 million ampere turns, e.g., about 2.5 to about 7.5 million ampere turns or about 3.75 million ampere turns to about 5 million ampere turns. In some examples, one set of coils is configured to receive a fixed (or constant) portion of the total variable electrical current, while the other set of coils is configured to receive a variable portion of the total electrical current. The total electrical current of the two coil sets varies with the variation of the current in one coil set. In other situations, the electrical current applied to both sets of coils can vary. The variable total current in the two sets of coils can generate a magnetic field having a variable magnitude, which in turn varies the acceleration pathways of the particles and produces particles having variable energies.

Generally, the magnitude of the magnetic field generated by the coil(s) is scalable to the magnitude of the total electrical current applied to the coil(s). Based on the scalability, in some implementations, linear variation of the magnetic field strength can be achieved by linearly changing the total current of the coil sets. The total current can be adjusted at a relatively high rate that leads to a relatively high-rate adjustment of the magnetic field and the beam energy.

In the example reflected in Table 1 above, the ratio between values of the current and the magnetic field at the geometric center of the coil rings is: 1990:8.7 (approximately 228.7:1); 1920:8.4 (approximately 228.6:1); 1760:7.9 (approximately 222.8:1). Accordingly, adjusting the magnitude of the total current applied to a superconducting coil(s) can proportionally (based on the ratio) adjust the magnitude of the magnetic field.

Figure 27:
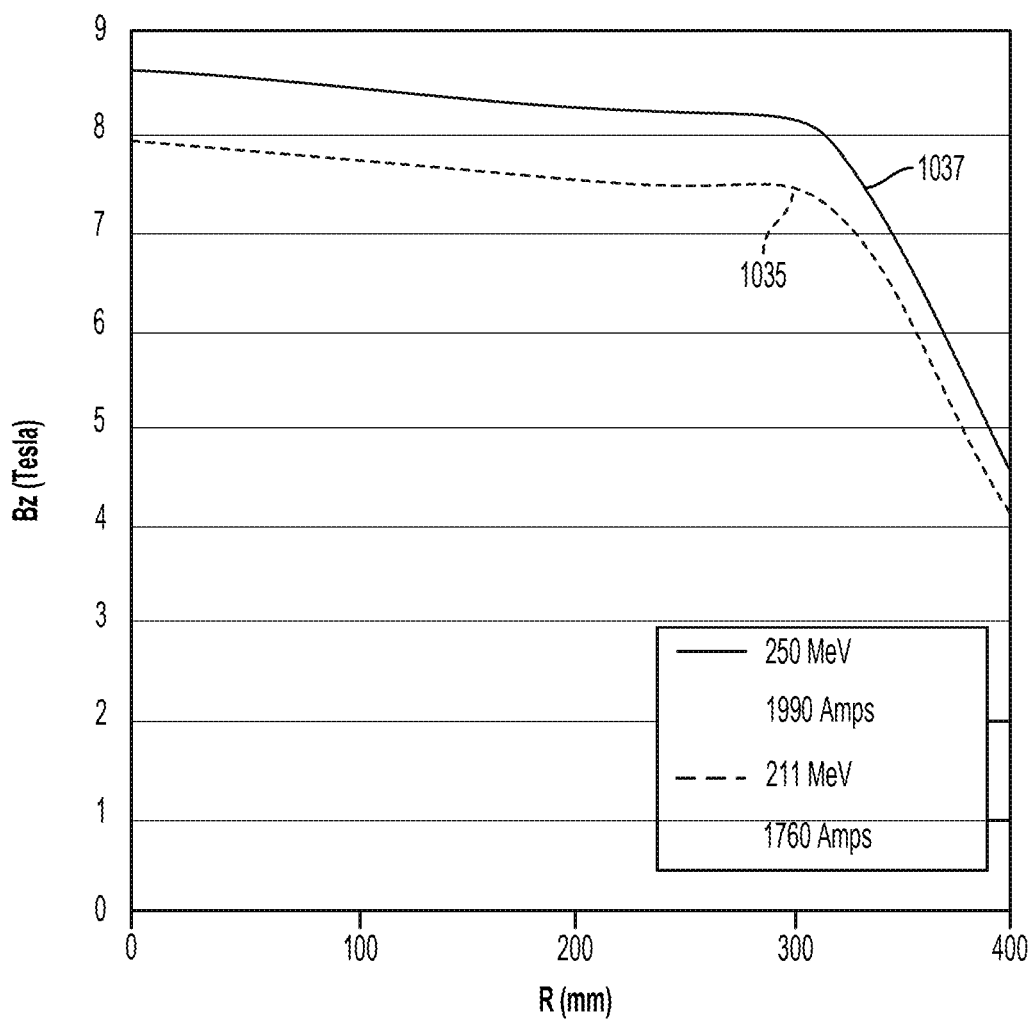
FIG. 27 is an example graph showing energy and current for variations in magnetic field and distance in a particle accelerator.

The scalability of the magnetic field to the total electrical current in the example of Table 1 is also shown in the plot of FIG. 27, where BZ is the magnetic field along the Z-dimension; and R is the radial distance measured from a geometric center of the coil rings along a direction perpendicular to the Z-dimension. The magnetic field has the highest value at the geometric center, and decreases as the distance R increases. The curves 1035, 1037 represent the magnetic field generated by the same coil sets receiving different total electrical current: 1760 Amperes and 1990 Amperes, respectively. The corresponding energies of the extracted particles are 211 MeV and 250 MeV, respectively. The two curves 1035, 1037 have substantially the same shape and the different parts of the curves 1035, 1037 are substantially parallel. As a result, either the curve 1035 or the curve 1037 can be linearly shifted to substantially match the other curve, indicating that the magnetic field is scalable to the total electrical current applied to the coil sets.

In some implementations, the scalability of the magnetic field to the total electrical current may not be perfect. For example, the ratio between the magnetic field and the current calculated based on the example shown in table 1 is not constant. Also, as shown in FIG. 27, the linear shift of one curve may not perfectly match the other curve. In some implementations, the total current is applied to the coil sets under the assumption of perfect scalability. The target magnetic field (under the assumption of perfect scalability) can be generated by additionally altering the features, e.g., geometry, of the coils to counteract the imperfection in the scalability. As one example, ferromagnetic (e.g., iron) rods (magnetic shims) can be inserted or removed from one or both of the magnetic structures (e.g., yokes, pole pieces, and the like). The features of the coils can be altered at a relatively high rate so that the rate of the magnetic field adjustment is not substantially affected as compared to the situation in which the scalability is perfect and only the electrical current needs to be adjusted. In the example of iron rods, the rods can be added or removed at the time scale of seconds or minutes, e.g., within 5 minutes, within 1 minute, less than 30 seconds, or less than 1 second.

In some implementations, settings of the accelerator, such as the current applied to the coil sets, can be chosen based on the substantial scalability of the magnetic field to the total electrical current in the coil sets.

Generally, to produce the total current that varies within a desired range, any appropriate combination of current applied to the two coil sets can be used. In an example, the coil set 42a, 42b can be configured to receive a fixed electrical current corresponding to a lower boundary of a desired range of the magnetic field. In the example shown in table 1, the fixed electrical current is 1760 Amperes. In addition, the coil set 40a, 40b can be configured to receive a variable electrical current having an upper boundary corresponding to a difference between an upper boundary and a lower boundary of the desired range of the magnetic field. In the example shown in table 1, the coil set 40a, 40b is configured to receive electrical current that varies between 0 Ampere and 230 Amperes.

In another example, the coil set 42a, 42b can be configured to receive a fixed electrical current corresponding to an upper boundary of a desired range of the magnetic field. In the example shown in table 1, the fixed current is 1990 Amperes. In addition, the coil set 40a, 40b can be configured to receive a variable electrical current having an upper boundary corresponding to a difference between a lower boundary and an upper boundary of the desired range of the magnetic field. In the example shown in table 1, the coil set 40a, 40b is configured to receive electrical current that varies between -230 Ampere and 0 Ampere.

The total variable magnetic field generated by the variable total current for accelerating the particles can have a maximum magnitude greater than 4 Tesla, e.g., greater than 5 Tesla, greater than 6 Tesla, greater than 7 Tesla, greater than 8 Tesla, greater than 9 Tesla, or greater than 10 Tesla, and up to about 20 Tesla or higher, e.g., up to about 18 Tesla, up to about 15 Tesla, or up to about 12 Tesla. In some implementations, variation of the total current in the coil sets can vary the magnetic field by about 0.2 Tesla to about 4.2 Tesla or more, e.g., about 0.2 Tesla to about 1.4 Tesla or about 0.6 Tesla to about 4.2 Tesla. In some situations, the amount of variation of the magnetic field can be proportional to the maximum magnitude.

Figure 28:
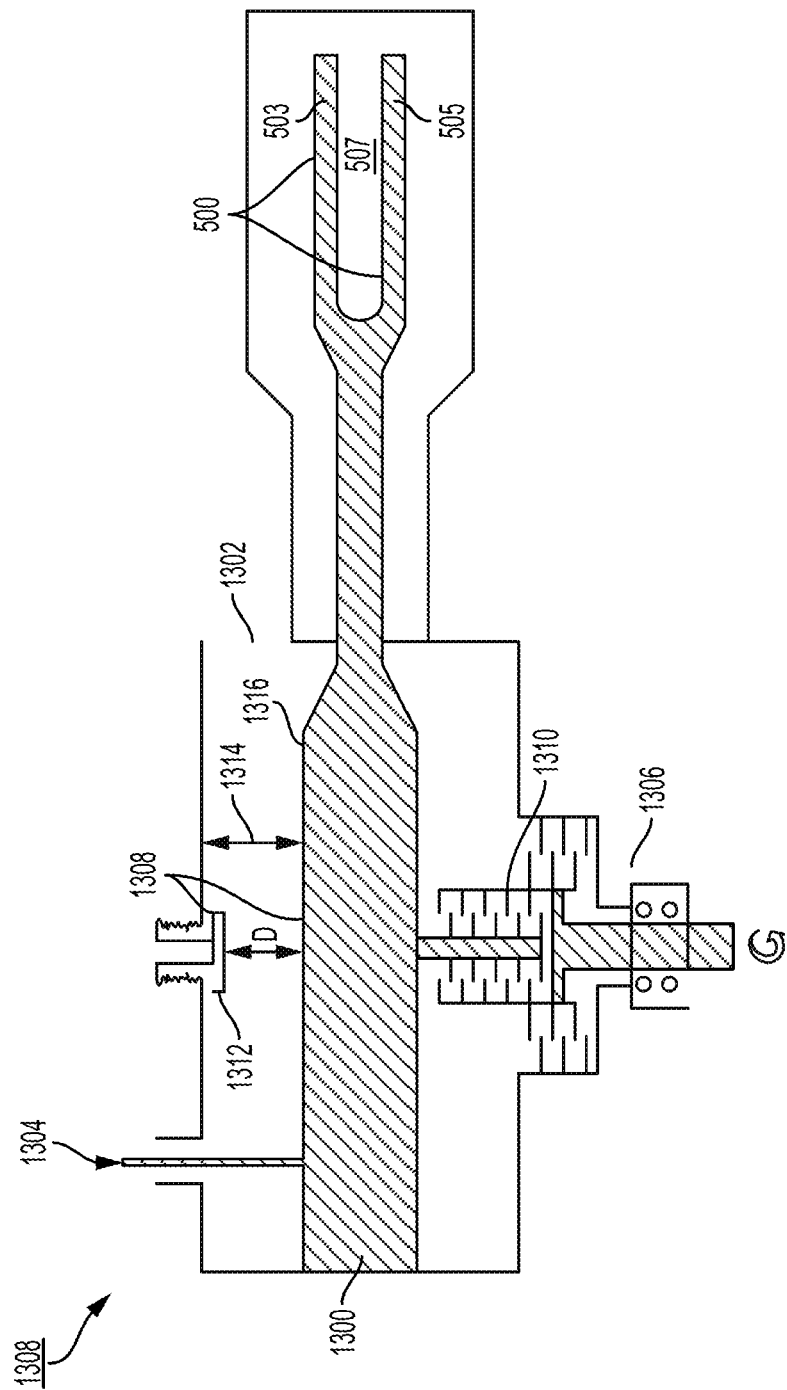
FIG. 28 is a side view of an example structure for sweeping voltage on a dee leaf over a frequency range for each energy level of a particle beam, and for varying the frequency range when the particle beam energy is varied.

FIG. 28 shows an example RF structure for sweeping the voltage on the dee plate 500 over an RF frequency range for each energy level of the particle beam, and for varying the frequency range when the particle beam energy is varied. The semicircular surfaces 503, 505 of the dee plate 500 are connected to an inner conductor 1300 and housed in an outer conductor 1302. The high voltage is applied to the dee plate 500 from a power source (not shown, e.g., an oscillating voltage input) through a power coupling device 1304 that couples the power source to the inner conductor. In some implementations, the coupling device 1304 is positioned on the inner conductor 1300 to provide power transfer from the power source to the dee plate 500. In addition, the dee plate 500 is coupled to variable reactive elements 1306, 1308 to perform the RF frequency sweep for each particle energy level, and to change the RF frequency range for different particle energy levels.

The variable reactive element 1306 can be a rotating capacitor that has multiple blades 1310 rotatable by a motor (not shown). By meshing or unmeshing the blades 1310 during each cycle of RF sweeping, the capacitance of the RF structure changes, which in turn changes the resonant frequency of the RF structure. In some implementations, during each quarter cycle of the motor, the blades 1310 mesh with the each other. The capacitance of the RF structure increases and the resonant frequency decreases. The process reverses as the blades 1310 unmesh. As a result, the power required to generate the high voltage applied to the dee plate 103 and necessary to accelerate the beam can be reduced by a large factor. In some implementations, the shape of the blades 1310 is machined to form the required dependence of resonant frequency on time.

The RF frequency generation is synchronized with the blade rotation by sensing the phase of the RF voltage in the resonator, keeping the alternating voltage on the dee plates close to the resonant frequency of the RF cavity. (The dummy dee is grounded and is not shown in FIG. 28).

The variable reactive element 1308 can be a capacitor formed by a plate 1312 and a surface 1316 of the inner conductor 1300. The plate 1312 is movable along a direction 1314 towards or away from the surface 1316. The capacitance of the capacitor changes as the distance D between the plate 1312 and the surface 1316 changes. For each frequency range to be swept for one particle energy, the distance D is at a set value, and to change the frequency range, the plate 1312 is moved corresponding to the change in the energy of the output beam.

In some implementations, the inner and outer conductors 1300, 1302 are formed of a metallic material, such as copper, aluminum, or silver. The blades 1310 and the plate 1312 can also be formed of the same or different metallic materials as the conductors 1300, 1302. The coupling device 1304 can be an electrical conductor. The variable reactive elements 1306, 1308 can have other forms and can couple to the dee plate 100 in other ways to perform the RF frequency sweep and the frequency range alteration. In some implementations, a single variable reactive element can be configured to perform the functions of both the variable reactive elements 1306, 1308. In other implementations, more than two variable reactive elements can be used.

The control of the gantry, the patient support, the active beam shaping elements, and the synchrocyclotron to perform a therapy session is achieved by appropriate therapy control electronics (not shown).

Control of the particle therapy system described herein and its various features may be implemented using hardware or a combination of hardware and software. For example, a system like the ones described herein may include various controllers and/or processing devices located at various points. A central computer may coordinate operation among the various controllers or processing devices. The central computer, controllers, and processing devices may execute various software routines to effect control and coordination of testing and calibration.

System operation can be controlled, at least in part, using one or more computer program products, e.g., one or more computer program tangibly embodied in one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the operations of the particle therapy system described herein can be performed by one or more programmable processors executing one or more computer programs to perform the functions described herein. All or part of the operations can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass PCBs for storing data, e.g., magnetic, magneto-optical disks, or optical disks. Non-transitory machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Any "electrical connection" as used herein may imply a direct physical connection or a wired or wireless connection that includes intervening components but that nevertheless allows electrical signals to flow between connected components. Any "connection" involving electrical circuitry mentioned herein, unless stated otherwise, may be an electrical connection and not necessarily a direct physical connection regardless of whether the word "electrical" is used to modify "connection".

Any two more of the foregoing implementations may be used in an appropriate combination in an appropriate particle accelerator (e.g., a synchrocyclotron). Likewise, individual features of any two more of the foregoing implementations may be used in an appropriate combination.

Elements of different implementations described herein may be combined to form other implementations not specifically set forth above. Elements may be left out of the processes, systems, apparatus, etc., described herein without adversely affecting their operation. Various separate elements may be combined into one or more individual elements to perform the functions described herein.

The example implementations described herein are not limited to use with a particle therapy system or to use with the example particle therapy systems described herein. Rather, the example implementations can be used in any appropriate system that directs accelerated particles to an output.

Other implementations not specifically described herein are also within the scope of the following claims.

What is claimed is:

1. A method comprising:
   storing, in computer memory, a library containing first information defining (a) positions of sets of parallel leaves of a configurable collimator that are extendible and retractable in a dimension to produce trimmed spots of a particle beam and (b) a configuration of carriages on the configurable collimator, the positions of the leaves being based on which of the leaves are extended and which of leaves are extracted;
   receiving, from a treatment planning process, second information comprising a dose distribution for an area of an irradiation target to be treated using the particle beam;

obtaining a coarse beam spot set based on a minimum dosage of the particle beam and a maximum dosage of the particle beam, the coarse beam spot set comprising representations of spots of the particle beam that approximate a target dose of the particle beam to be applied to the area of the irradiation target to be treated using the particle beam, the minimum dosage comprising a minimum dosage to be applied to the area, and the maximum dosage comprising a maximum dosage to be applied outside of the area;

changing the spots in the coarse beam spot set to more closely approximate the dose distribution of the particle beam;

retrieving at least some of the first information from the library based on the changed spots in the coarse spot beam set;

moving the configurable collimator to the area; and configuring the leaves and at least one of the carriages in the area based on the retrieved first information to trim the particle beam;

wherein the carriages comprise:

a primary carriage coupled to the leaves to move the leaves relative to the irradiation target in a first dimension relative to the irradiation target that is different from the dimension in which the leaves are extendible and retractable; and secondary carriages coupled to the primary carriage and to the leaves to move the leaves in a second dimension relative to the irradiation target, the second dimension being the dimension in which the leaves are extendible and retractable.

2. A particle therapy system comprising:

a particle accelerator to output a particle beam for application to an irradiation target;

a configurable collimator comprising (a) sets of parallel leaves that are extendible and retractable in a dimension and (b) carriages coupled to the sets of parallel leaves;

one or more non-transitory machine-readable storage media storing (i) a library containing (a) first information defining positions of the sets of the leaves and (b) a configuration of the carriages, the positions of the sets of leaves being based on which of the leaves are extended and which of leaves are extracted, and (ii) instructions that are executable by one or more processing devices; and a control system comprising one or more processing devices configured to execute the instructions to perform operations comprising:

receiving, from a treatment planning process, second information comprising a dose distribution for an area of the irradiation target to be treated using the particle beam;

obtaining a coarse beam spot set based on a minimum dosage of the particle beam and a maximum dosage of the particle beam, the coarse beam spot set comprising representations of spots of the particle beam that approximate a target dose of the particle beam to be applied to the area of an irradiation target to be treated using the particle beam, the minimum dosage comprising a minimum dosage to be applied to the area, and the maximum dosage comprising a maximum dosage to be applied outside of the area;

causing the spots in the coarse beam spot set to change to more closely approximate the dose distribution of the particle beam;

retrieving at least some of the first information from the library based on the changed spots in the coarse beam spot set;

controlling the configurable collimator to move to the area; and controlling the leaves and the carriages to be configured in the area based on the retrieved first information to trim the particle beam;

wherein the carriages comprise:

a primary carriage to move the leaves relative to the irradiation target in a first dimension relative to the irradiation target that is different from the dimension in which the leaves are extendible and retractable; and secondary carriages coupled to the primary carriage to move the leaves in a second dimension relative to the irradiation target, the second dimension being the dimension in which the leaves are extendible and retractable.

3. The particle therapy system of claim 2, wherein the configurable collimator comprises two sets of the leaves that face each other.

4. The particle therapy system of claim 2, wherein spots in the coarse beam spot set are defined by geometric features.

5. The particle therapy system of claim 2, wherein the first information corresponds to spots of the particle beam that are to be formed on the irradiation target.

6. The particle therapy system of claim 2, wherein the leaves are configurable on a spot-by-spot of the particle beam basis.

7. The particle therapy system of claim 6, wherein at least two successive spots of the particle beam on the irradiation target have at least one of a different size or a different shape.

8. The particle therapy system of claim 2, wherein the second dimension comprises movement into, and out of, the area of the irradiation target.

9. The particle therapy system of claim 2, wherein moving the configurable collimator comprises rotating at least one secondary carriage.

10. The particle therapy system of claim 9, wherein the leaves comprise two sets of parallel leaves that face each other.

11. The particle therapy system of claim 2, wherein the control system is configured to control rotation of all or part of the configurable collimator.

12. The method of claim 1, wherein at least two successive spots produced by the particle beam on the irradiation target have at least one of a different size or a different shape.

13. One or more non-transitory machine-readable storage media storing: a library containing first information defining (a) positions of sets of parallel leaves of a configurable collimator that are extendible and retractable in a dimension to produce trimmed spots of a particle beam and (b) a configuration of carriages on the configurable collimator, the positions of the leaves being based on which of the leaves are extended and which of leaves are extracted;

receiving, from a treatment planning process, second information comprising a dose distribution for an area of an irradiation target to be treated using the particle beam;

obtaining a coarse beam spot set based on a minimum dosage of the particle beam and a maximum dosage of the particle beam, the coarse beam spot set comprising representations of spots of the particle beam that approximate a target dose of the particle beam to be applied to the area of the irradiation target to be treated using the particle beam, the minimum dosage comprising a minimum dosage to be applied to the area, and the maximum dosage comprising a maximum dosage to be applied outside of the area;

causing the spots in the coarse beam spot set to change to more closely approximate the dose distribution of the particle beam;

retrieving at least some of the first information from the library based on the changed spots in the coarse beam spot set;

controlling the configurable collimator to move to the area; and controlling the leaves and at least one of the carriages to be configured in the area based on the retrieved first information to trim the particle beam;

wherein the carriages comprise:
a primary carriage coupled to the leaves to move the leaves relative to the irradiation target in a first dimension relative to the irradiation target that is different from the dimension in which the leaves are extendible and retractable; and secondary carriages coupled to the primary carriage and to the leaves to move the leaves in a second dimension relative to the irradiation target, the second dimension being the dimension in which the leaves are extendible and retractable.

14. The one or more non-transitory machine-readable storage media of claim 13, wherein the leaves comprise two sets of leaves that face each other.

15. The one or more non-transitory machine-readable storage media of claim 13, wherein the spots in the coarse set of spots are defined by geometric features.

16. The one or more non-transitory machine-readable storage media of claim 13, wherein the first information corresponds to where spots of the particle beam are to be formed on the irradiation target.

17. The one or more non-transitory machine-readable storage media of claim 13, wherein the leaves are configurable on a spot-by-spot of the particle beam basis.

18. The one or more non-transitory machine-readable storage media of claim 13, wherein at least two successive spots of the particle beam on the irradiation target have at least one of a different size or a different shape.

19. The one or more non-transitory machine-readable storage media of claim 13, wherein the second dimension comprises movement into, and out of, the area.

20. The one or more non-transitory machine-readable storage media of claim 13, wherein the configurable collimator comprises rotating at least one secondary carriage.

21. The one or more non-transitory machine-readable storage media of claim 13, wherein the operations comprise controlling the configurable collimator to rotate.

22. The method of claim 1, wherein the configurable collimator comprises two sets of the leaves that face each other.

23. The method of claim 1, wherein spots in the coarse beam spot set are defined by geometric features.

24. The method of claim 1, wherein the first information corresponds to spots of the particle beam are to be formed on the irradiation target.

25. The method of claim 1, wherein the leaves are configurable on a spot-by-spot of the particle beam basis.

26. The method of claim 25, wherein at least two successive spots of the particle beam on the irradiation target have at least one of a different size or a different shape.

27. The method of claim 1, wherein the second dimension comprises movement into, and out of, the area.

28. The method of claim 1, wherein moving the configurable collimator comprises rotating at least one secondary carriage.

29. The method of claim 28, wherein the leaves comprise two sets of parallel leaves that face each other.

30. The method of claim 1, wherein the control system is configured to control rotation of all or part of the configurable collimator.

* * * * *